(12) United States Patent
Cho et al.

(10) Patent No.: US 7,838,129 B2
(45) Date of Patent: *Nov. 23, 2010

(54) COMPOUND AND ORGANIC LIGHT EMITTING DEVICE USING THE SAME

(75) Inventors: Wook Dong Cho, Daejeon Metropolitan (KR); Ji Eun Kim, Daejeon Metropolitan (KR); Byung Sun Jeon, Seoul (KR); Seok Hee Yoon, Daejeon Metropolitan (KR); Jae Min Moon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 675 days.

This patent is subject to a terminal disclaimer.

(21) Appl. No.: 11/660,761

(22) PCT Filed: Sep. 23, 2005

(86) PCT No.: PCT/KR2005/003173

§ 371 (c)(1),
(2), (4) Date: Feb. 22, 2007

(87) PCT Pub. No.: WO2006/080640

PCT Pub. Date: Aug. 3, 2006

(65) Prior Publication Data

US 2007/0247059 A1    Oct. 25, 2007

(30) Foreign Application Priority Data

Sep. 24, 2004 (KR) .................. 10-2004-0077245

(51) Int. Cl.
*H01L 51/54* (2006.01)
*C09K 11/00* (2006.01)

(52) U.S. Cl. .............. 428/690; 428/917; 313/504; 313/506; 252/301.16; 257/40; 257/103; 257/E51.032; 546/15; 546/16; 546/18; 556/408

(58) Field of Classification Search .................. 556/408
See application file for complete search history.

(56) References Cited

U.S. PATENT DOCUMENTS

| 6,613,454 | B2 | 9/2003 | Ara et al. | |
|---|---|---|---|---|
| 2002/0086180 | A1 * | 7/2002 | Seo et al. | 428/690 |
| 2004/0219386 | A1 | 11/2004 | Thoms | |

FOREIGN PATENT DOCUMENTS

| JP | 2008-511157 | 4/2008 |
|---|---|---|
| JP | 2008-511158 | 4/2008 |
| JP | 2008-511159 | 4/2008 |
| JP | 2008-511160 | 4/2008 |
| WO | WO 93/09074 | 5/1993 |
| WO | WO 2006/080640 | 8/2006 |
| WO | WO 2006/080641 | 8/2006 |
| WO | WO 2006/080642 | 8/2006 |
| WO | WO 2006/080643 | 8/2006 |
| WO | WO 2006/080644 | 8/2006 |

OTHER PUBLICATIONS

Tritschler, Wolfgang et al., "Synthese und Konformation von Spiroacridanen", Chem. Ber. 117, 2703-2713 (1984).
Patrick Keller, "Photo-Cross-Linkable Liquid-Crystalline Side-Chain Polysiloxanes", Chemistry of Materials, vol. 2, pp. 3-4, 1990.
Geselowitz et al., "Quantitation of Triple-Helix Formation Using a Photo-Cross-Linkable Aryl Azide/Biotin/Oligonucleotide Conjugate", Bioconjugate Chem., vol. 6, pp. 502-506, 1995.

* cited by examiner

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is a novel compound which is capable of significantly improving a lifespan, efficiency, and electrochemical and thermal stabilities of an organic light emitting device, the production of the compound, and an organic light emitting device in which the compound is contained in an organic compound layer.

13 Claims, 1 Drawing Sheet

[Fig. 1]
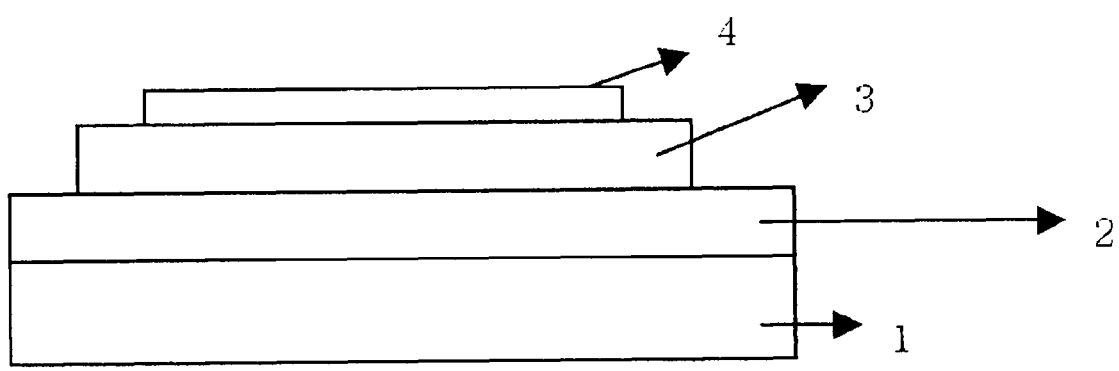
[Fig. 2]
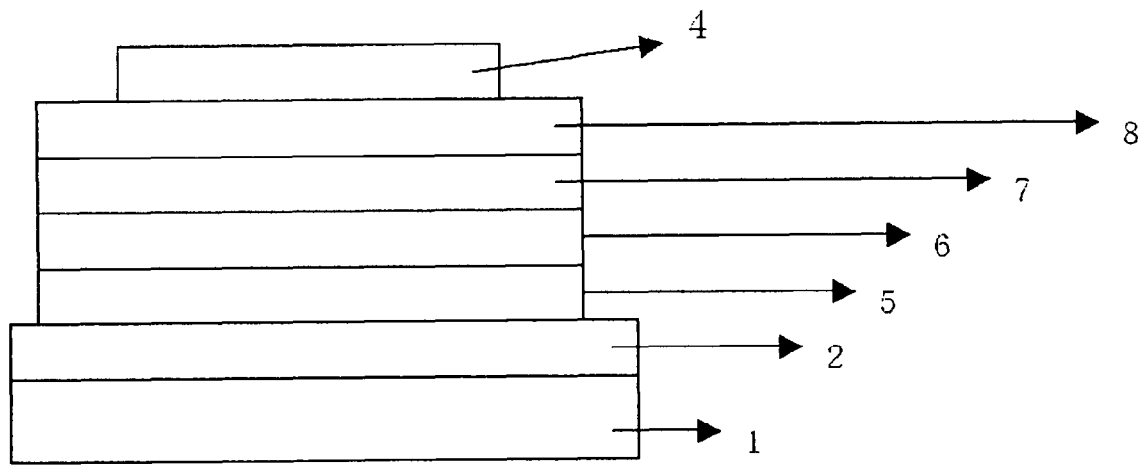

US 7,838,129 B2

COMPOUND AND ORGANIC LIGHT EMITTING DEVICE USING THE SAME

This application claims priority to International application No. PCT/KR2005/003173 filed on Sep. 23, 2005, and Korean Application No. 10-2004-0077245 filed on Sep. 24, 2004, both of which are incorporated by reference, as if fully set forth herein.

TECHNICAL FIELD

The present invention relates to a novel compound which is capable of significantly improving a lifespan, efficiency, and electrochemical and thermal stabilities of an organic light emitting device, the production of the compound, and an organic light emitting device in which the compound is contained in an organic compound layer.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

DISCLOSURE OF INVENTION

Technical Problem

Accordingly, there is a need to develop an organic material having the above-mentioned requirements in the art.

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Furthermore, the present invention aims to provide the production of a novel organic light emitting material found by the present inventors, and an organic light emitting device using the same.

Technical Solution

The present invention provides a compound of Formula 1.

The present invention provides a method of producing the compound of Formula 1.

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

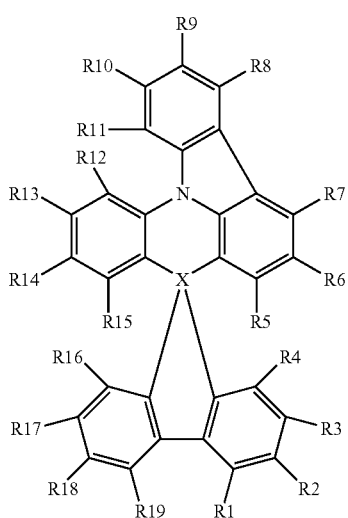

[Formula 1]

In Formula 1, X is C or Si.

$R_1$ to $R_{19}$ are each independently selected from the group consisting of hydrogen; an alkyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkoxy group, which is substituted or un-substituted with at least one substituent group selected from the group consisting of a halogen group, an alkyl group, an alkenyl group, an alkoxy group, a substituted or un-substituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkenyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an aryl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or un-substituted arylalkenyl group, a substituted or unsubstituted heterocyclic group, a substituted or unsubstituted heterocyclic group, a nitrile group, and an acetylene group; a hetero arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; a heterocyclic group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group and which includes O, N, or S as a heteroatom; an amino group, which is substituted with at least one substituent group selected from the group consisting of an alkyl group, an alkenyl group, a substituted or unsubstituted aryl group, a substituted or unsubstituted arylalkyl group, and a substituted or unsubstituted arylalkenyl group; a nitrile group; a nitro group; a halogen group; an amide group; and an ester group, and $R_1$ to $R_{19}$ may form aliphatic or hetero condensation rings along with adjacent groups.

$R_{11}$ and $R_{12}$ may be directly connected to each other, or may form a condensation ring along with a group selected from the group consisting of O, S, NR, PR, C=O, CRR', C=CRR', and SiRR', R and R' being independently or collectively selected from the group consisting of hydrogen, oxygen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group, and R and R' may form a condensation ring to form a spiro compound.

A detailed description will be given of the substituent groups of Formula 1.

The carbon number of the alkyl, alkoxy, and alkenyl groups of R1 to R19 of Formula 1 is preferably 1-20.

Illustrative, but non-limiting, examples of the aryl group of R1 to R19 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R19 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R19 of Formula 1 include a thiophene group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

According to a preferred embodiment of the present invention, X of Formula 1 is C, and R11 and R12 may be directly connected to each other, or may form a condensation ring along with a group selected from the group consisting of O, S, NR, PR, C=O, CRR', C=CRR', and SiRR' (R and R' are as defined in claim 1).

According to another preferred embodiment of the present invention, X of Formula 1 is Si, and R11 and R12 are directly connected to each other, or form a condensation ring along with a group selected from the group consisting of O, S, NR, PR, C=O, CRR', C=CRR', and SiRR' (R and R' are as defined in claim 1).

According to still another preferred embodiment of the present invention, any one of R1 to R4 and/or any one of R16 to R19 in Formula 1 is the arylamine group, which is substituted or unsubstituted with at least one substituent group selected from the group consisting of the halogen group, the alkyl group, the alkenyl group, the alkoxy group, the substituted or unsubstituted arylamine group, the substituted or un-substituted aryl group, the substituted or unsubstituted arylalkyl group, the substituted or unsubstituted arylalkenyl group, the substituted or unsubstituted heterocyclic group, the nitrile group, and the acetylene group.

Illustrative, but non-limiting, examples of the substituent groups of Formula 1 are as follows.

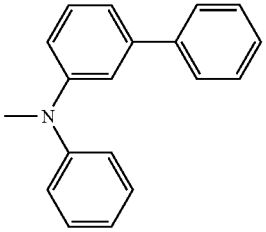

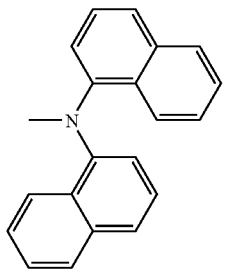

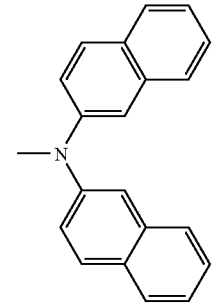

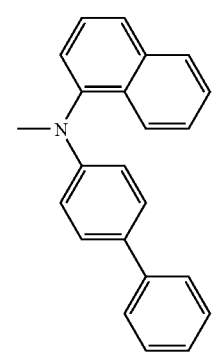

-continued

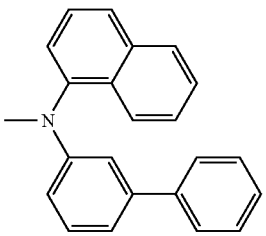

-continued
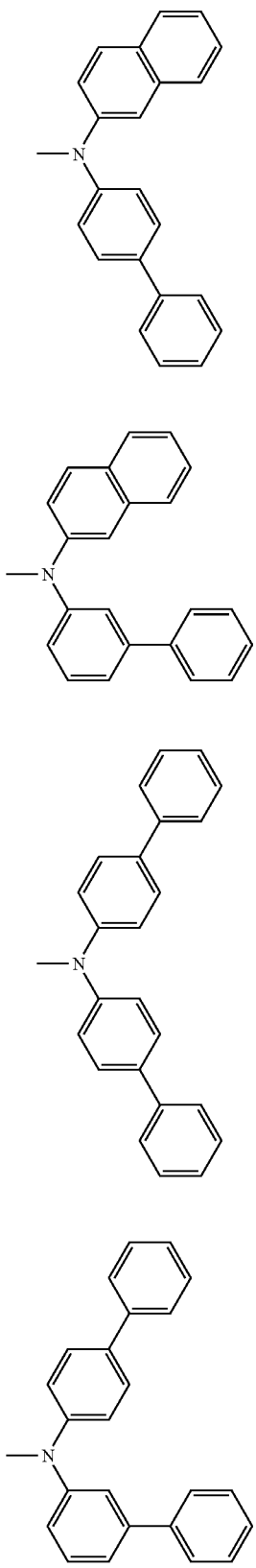
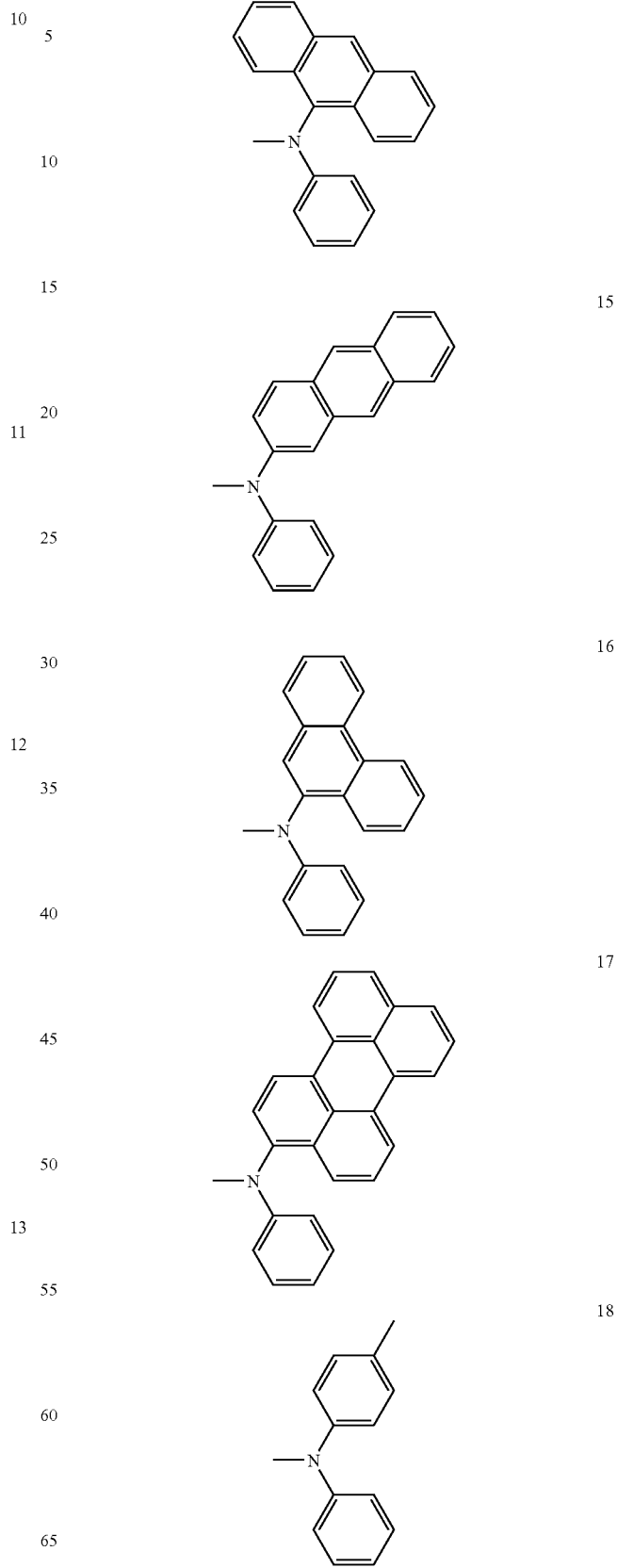

-continued
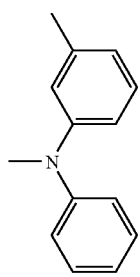
19
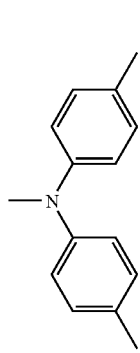
20
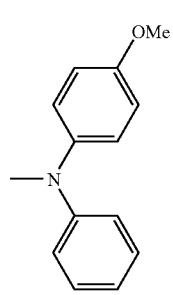
21
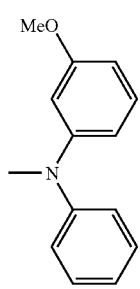
22
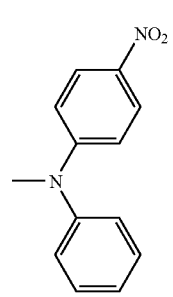
23
-continued
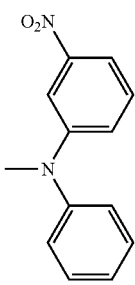
24
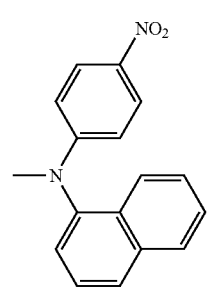
25
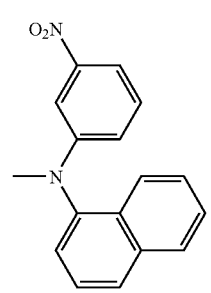
26
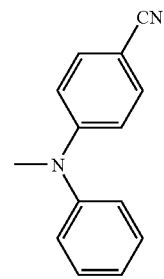
27
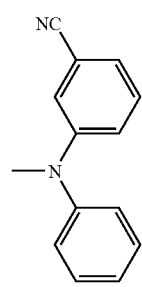
28

-continued
29
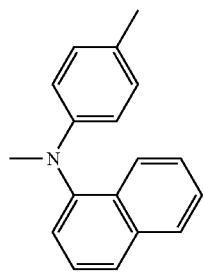
30
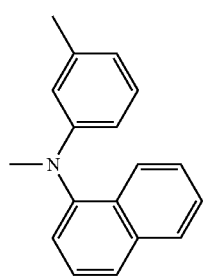
31
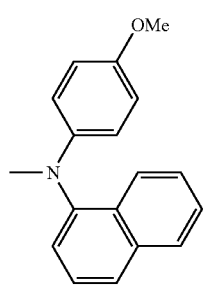
32
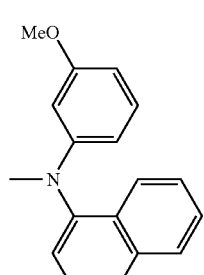
33
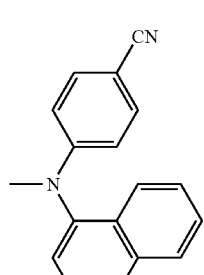
-continued
34
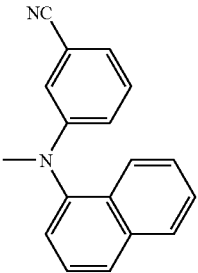
35
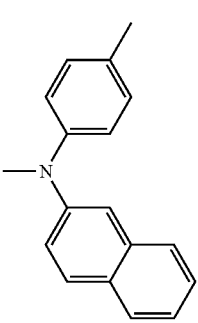
36
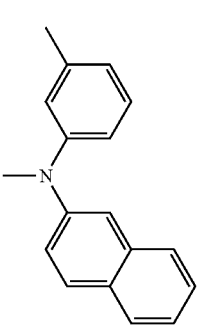
37
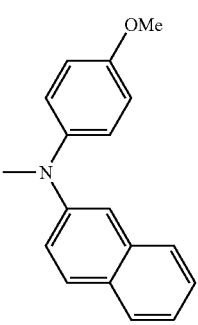
38
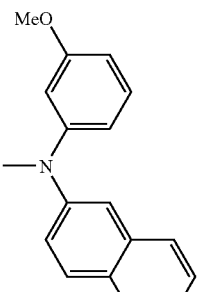

-continued

48
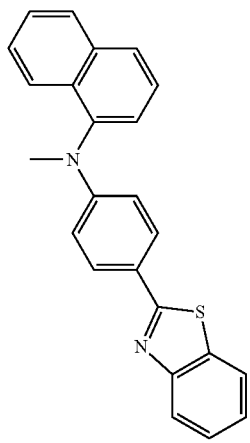
49
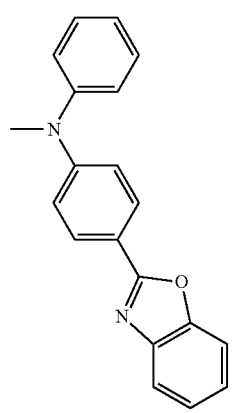
50
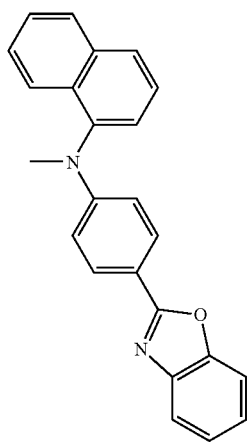
51
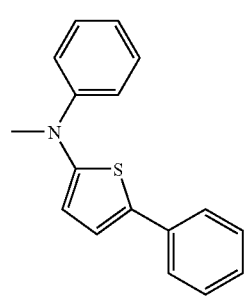
52
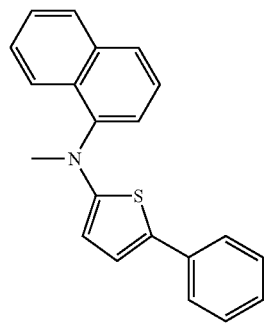
53
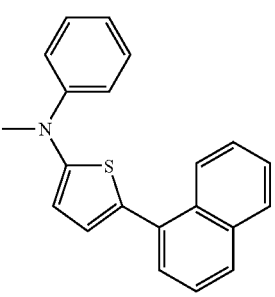
54
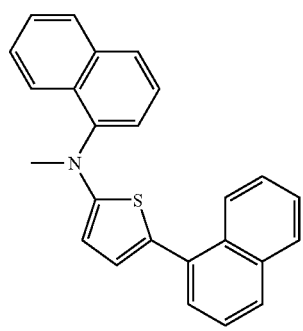
55
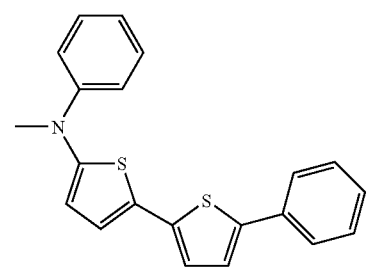
56
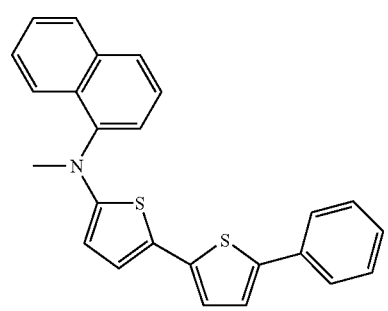

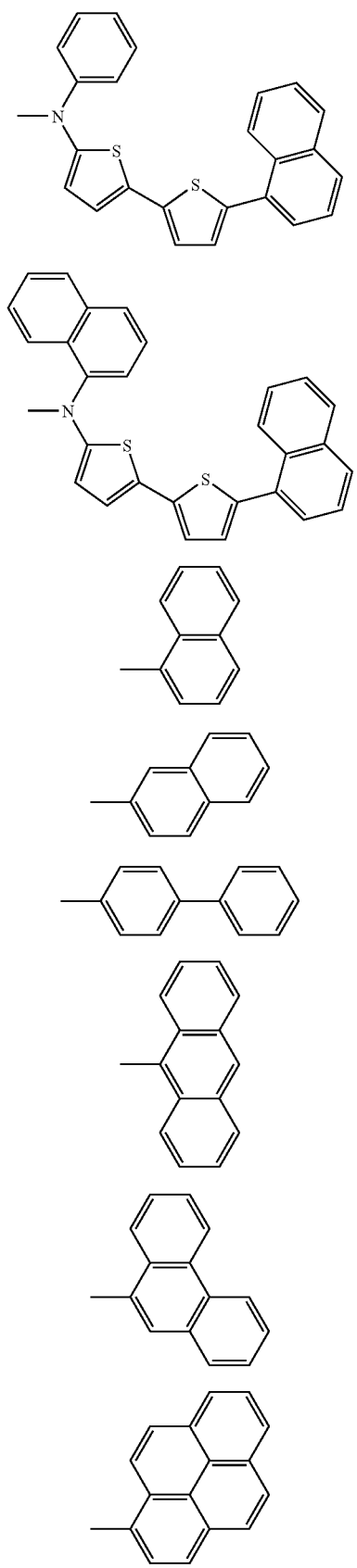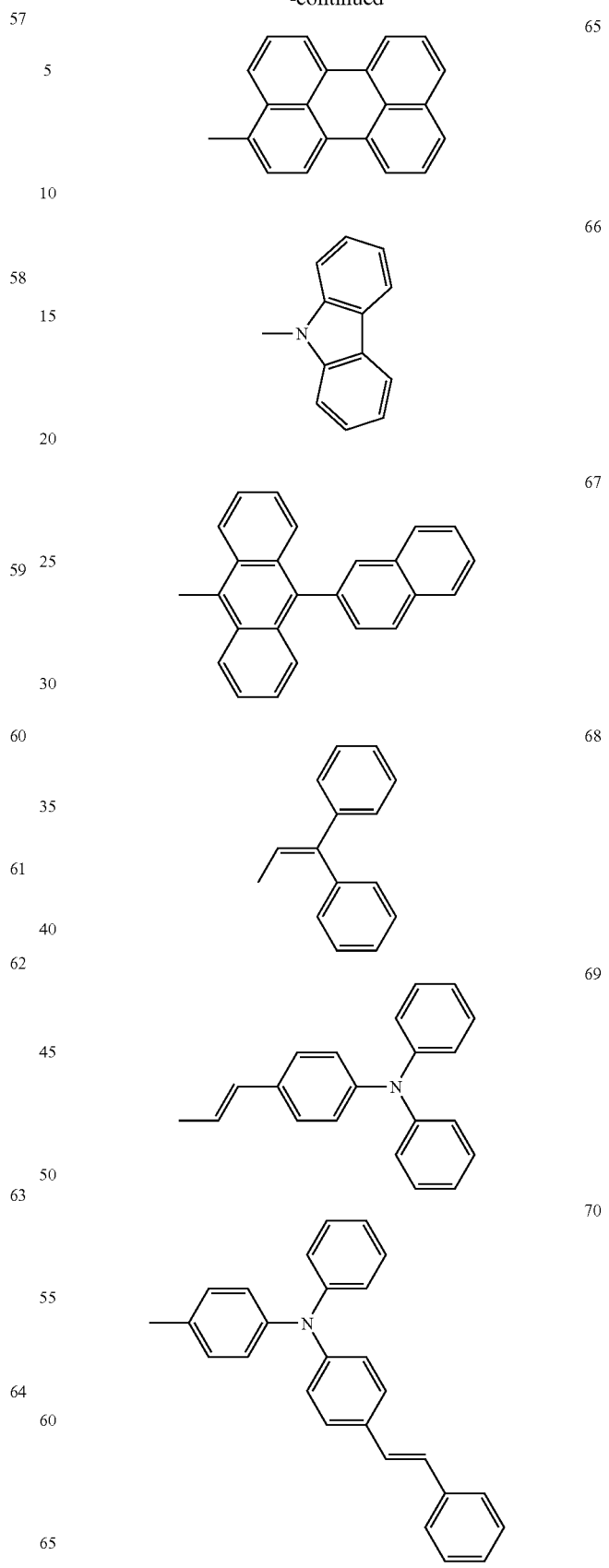

71 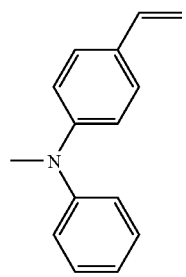
72 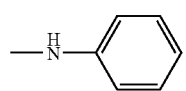
73 
74 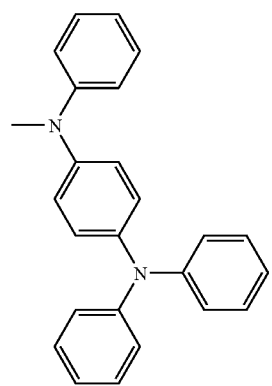
75 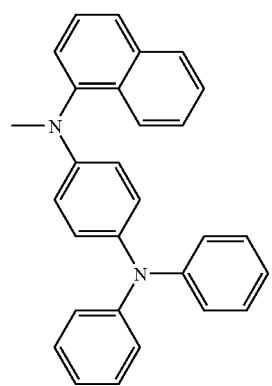
76 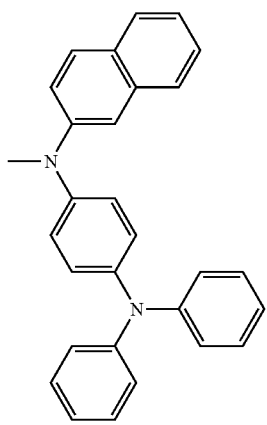
77 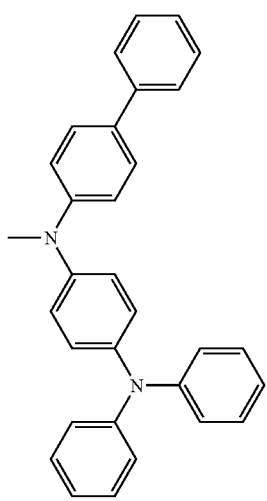
78 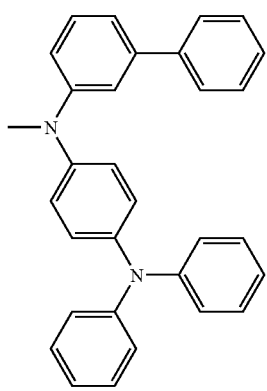

79
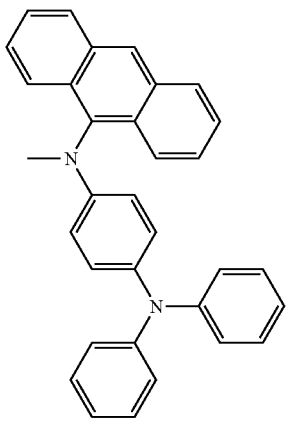
80
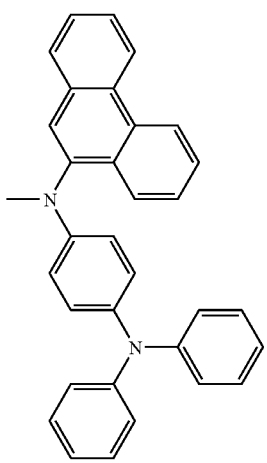
81
82
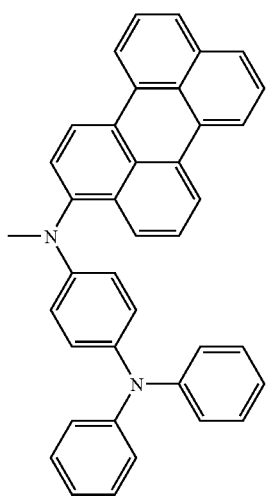
83
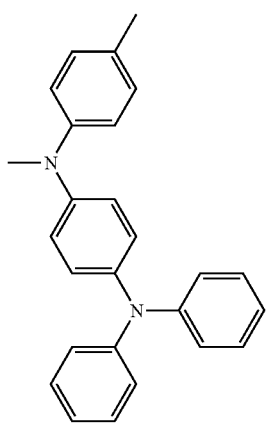
84
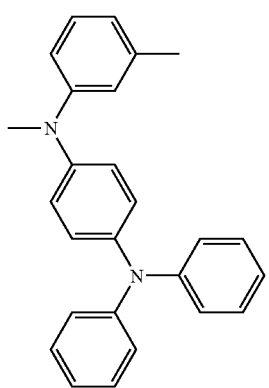

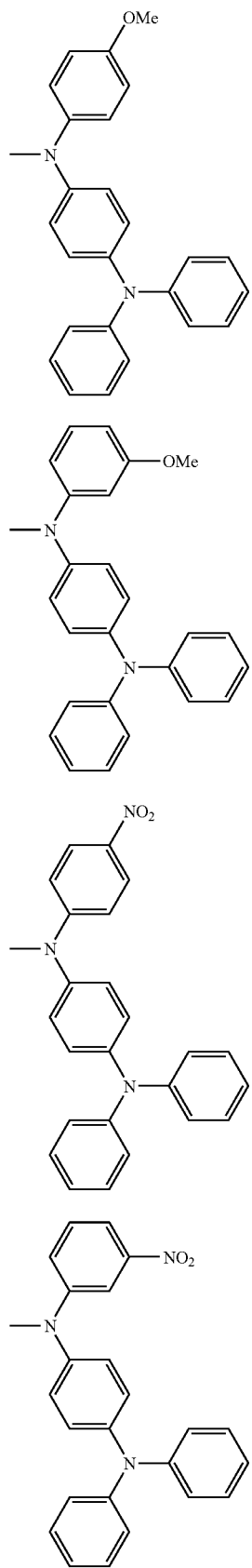
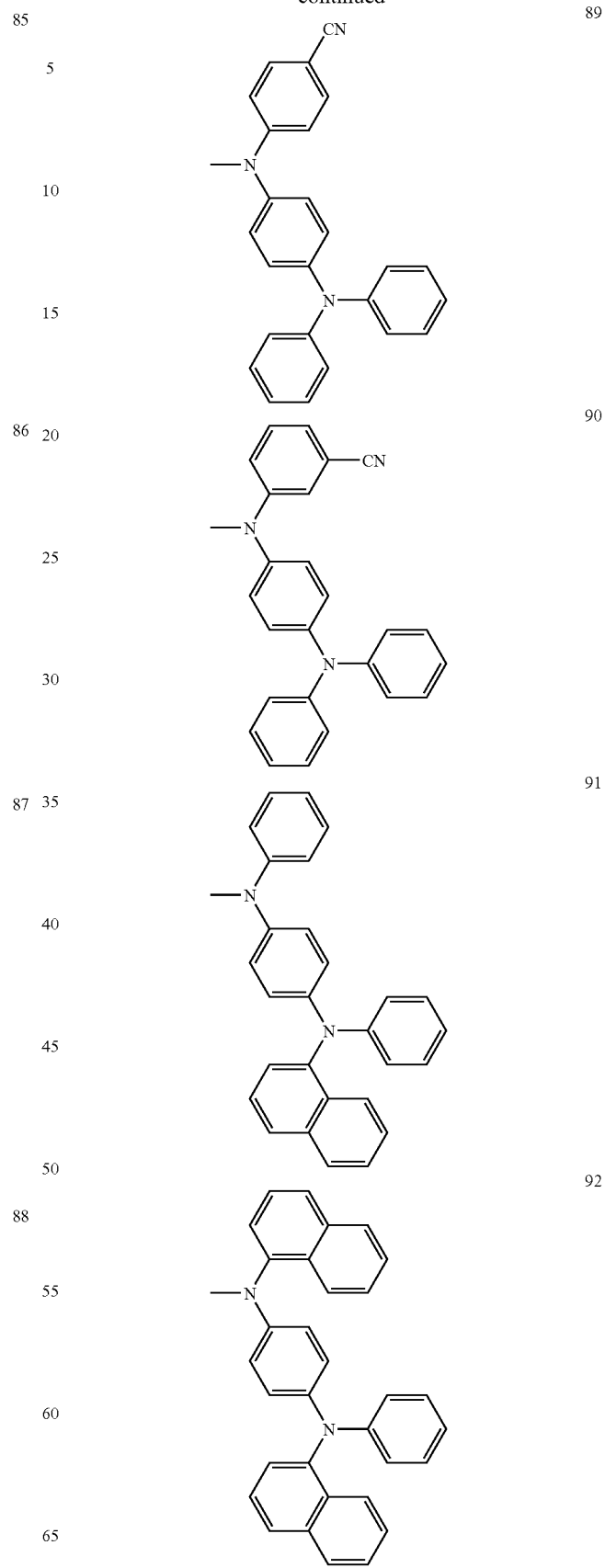

93
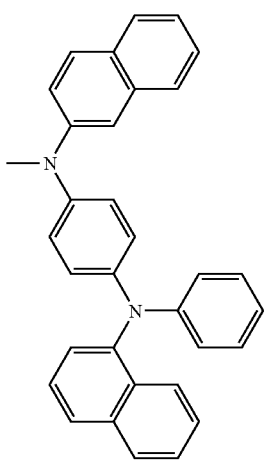
96
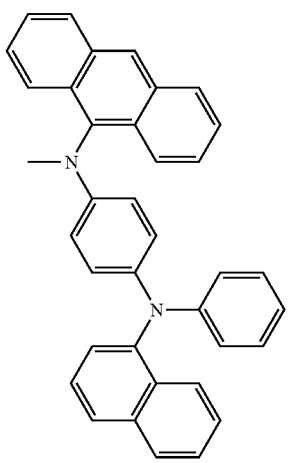
94
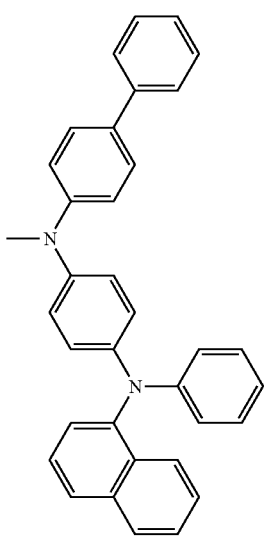
97
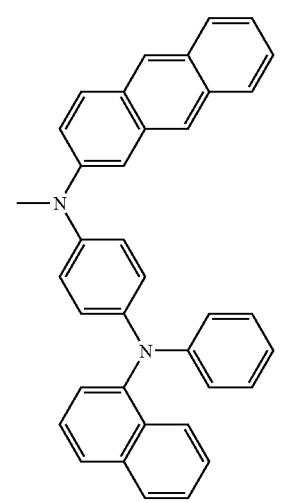
95
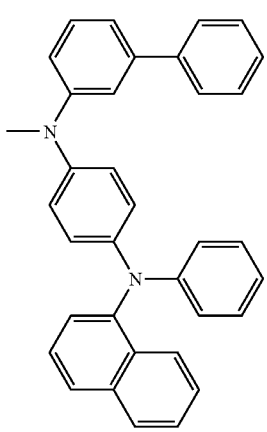
98
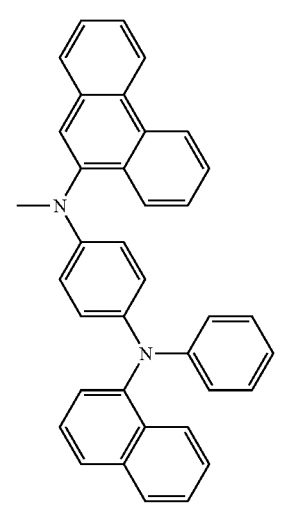

-continued
98
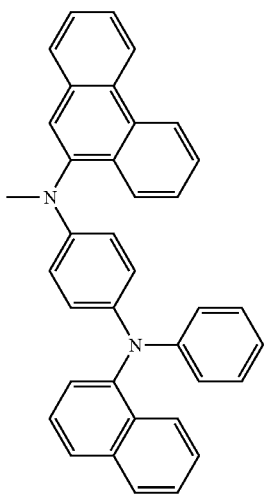
99
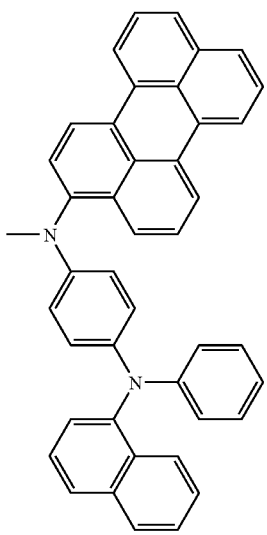
100
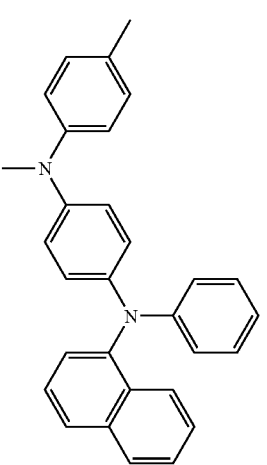
-continued
101
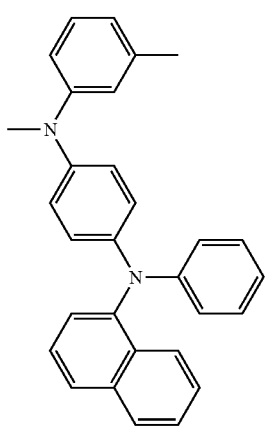
102
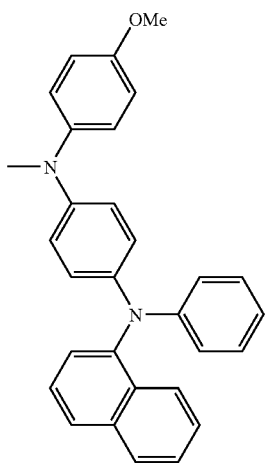
103
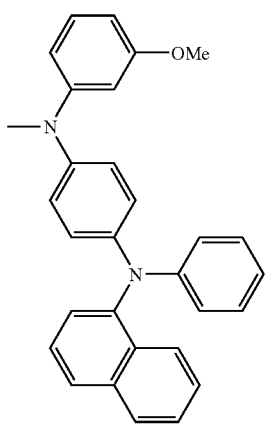

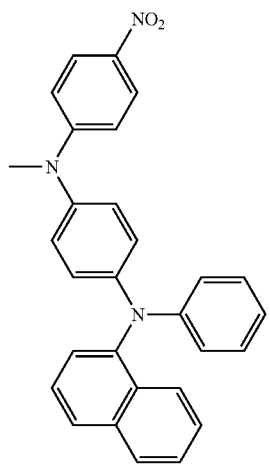
104
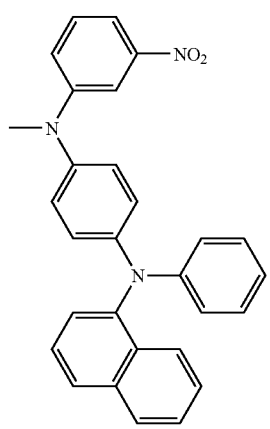
105
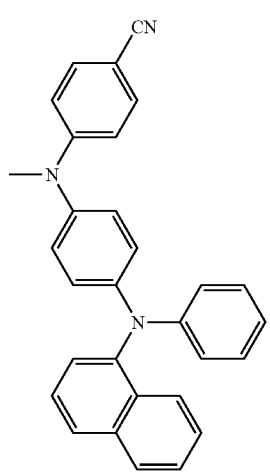
106
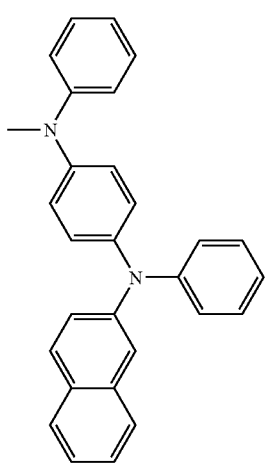
107
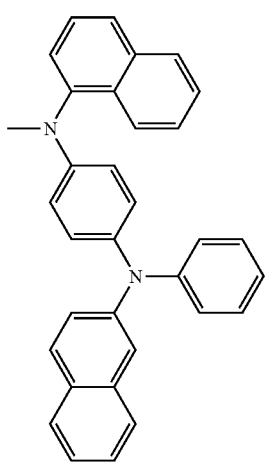
108
109

-continued
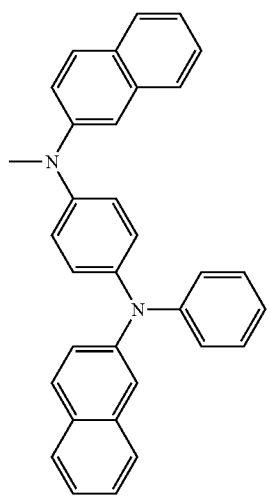
110
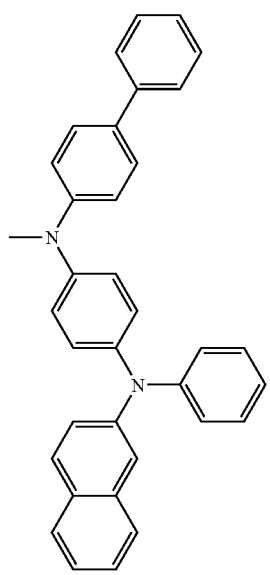
111
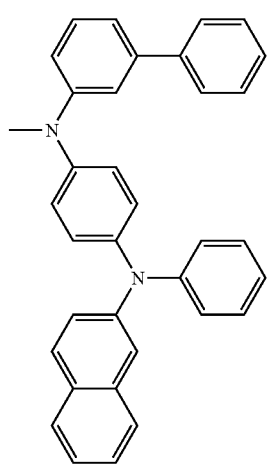
112
-continued
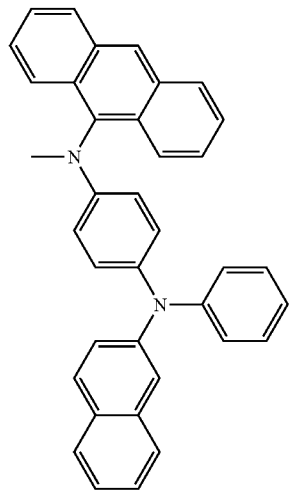
113
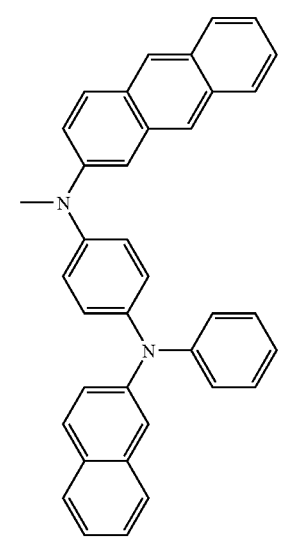
114
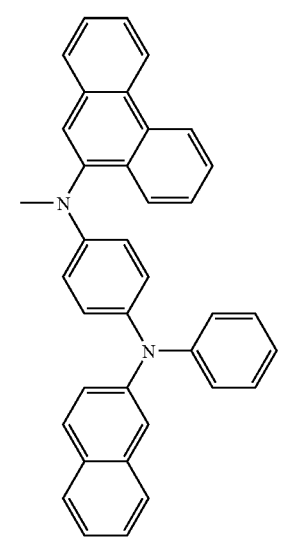
115

-continued
116
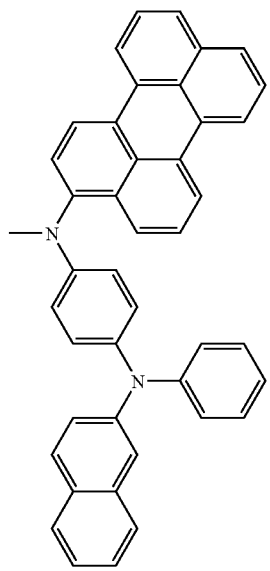
117
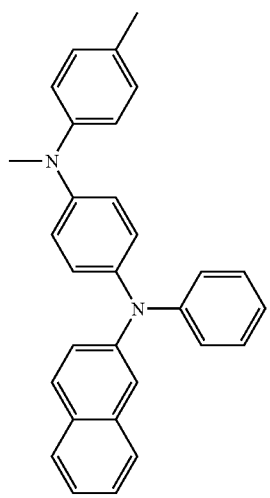
118
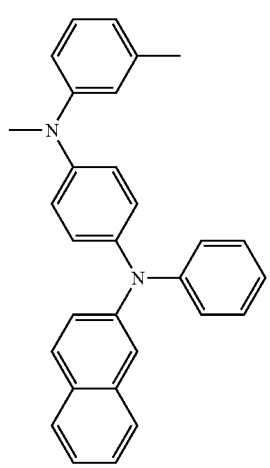
-continued
119
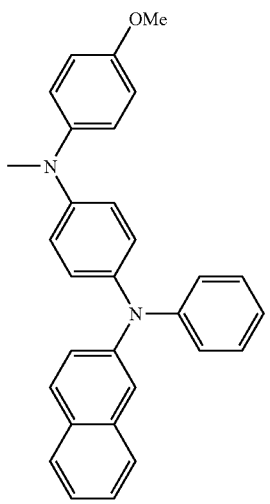
120
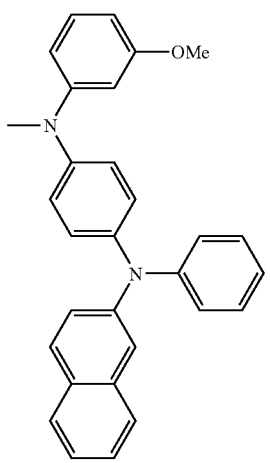
121
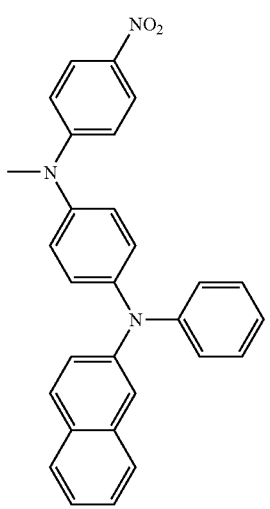

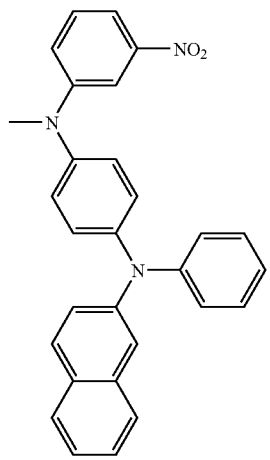
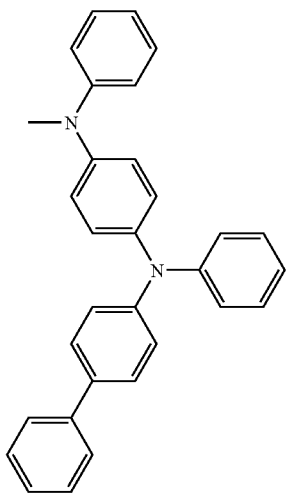
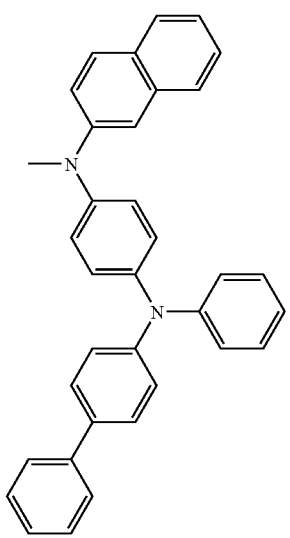

-continued
128
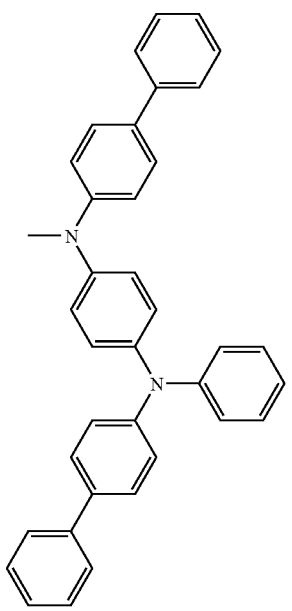
129
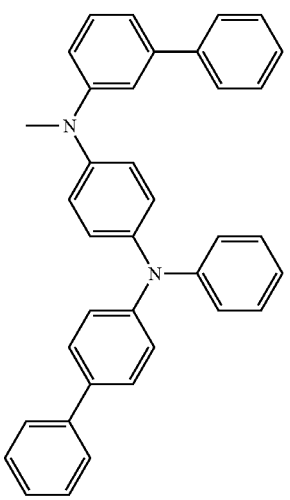
130
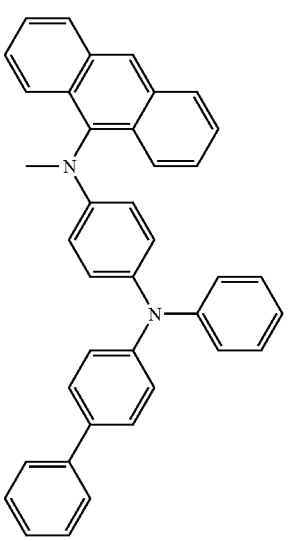
-continued
131
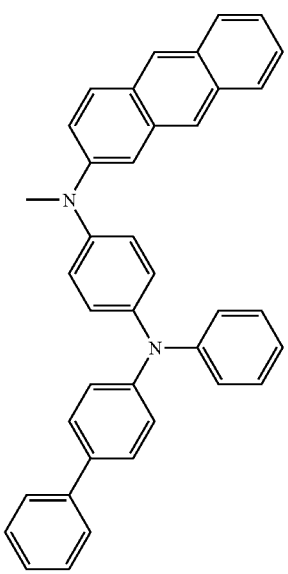
132
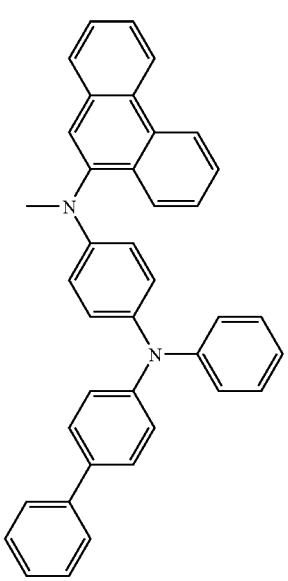

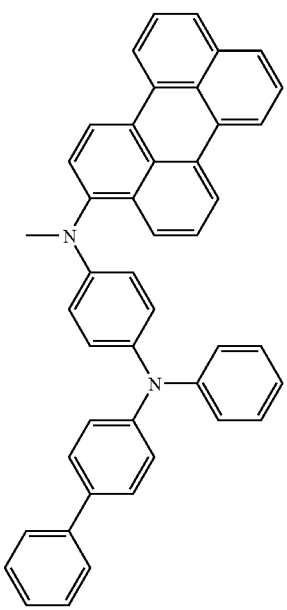
133
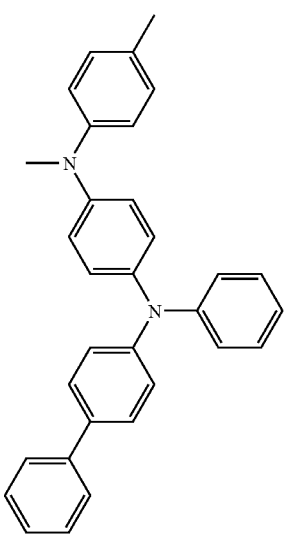
134
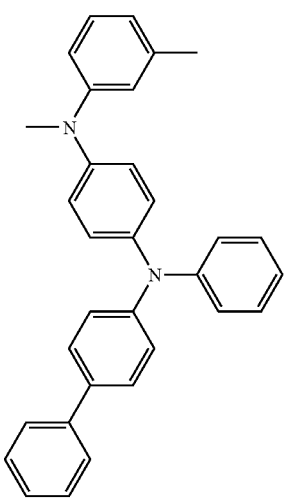
135
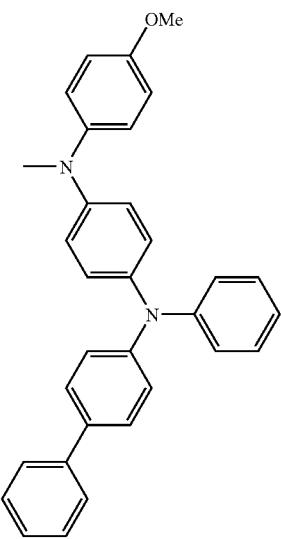
136
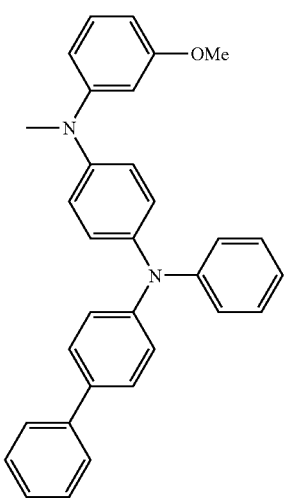
137
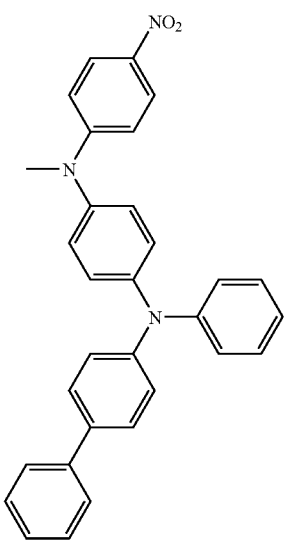
138

-continued
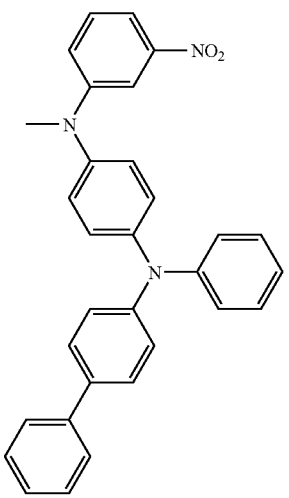
139
140
141
-continued
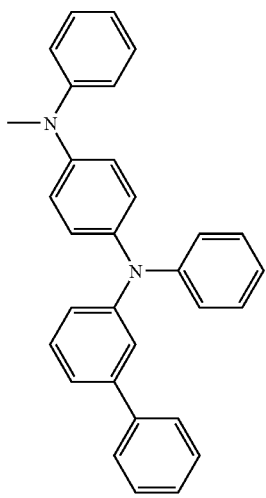
142
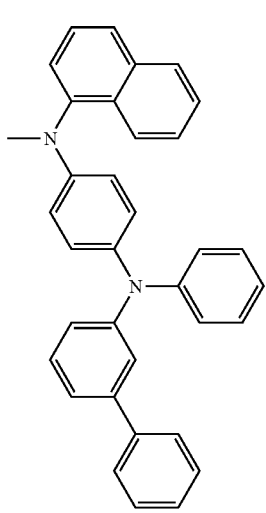
143
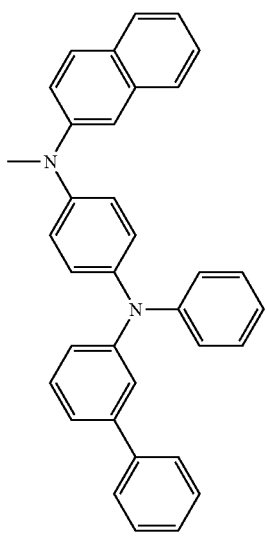
144

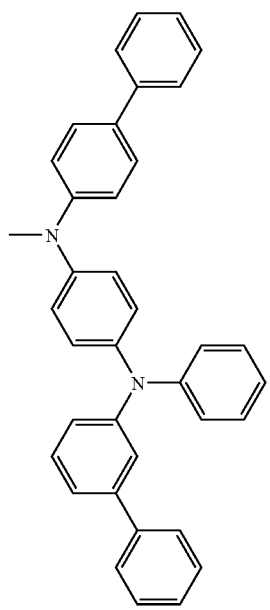
145
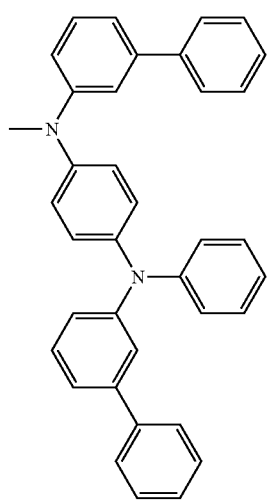
146
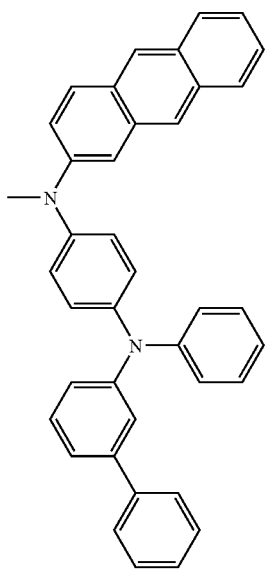
148
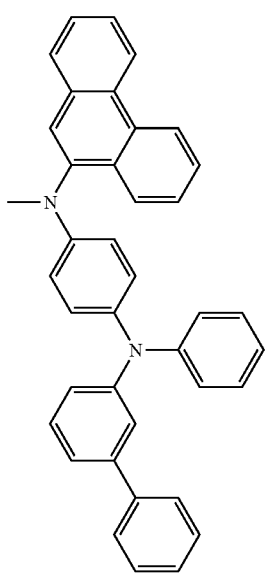
149

-continued
150
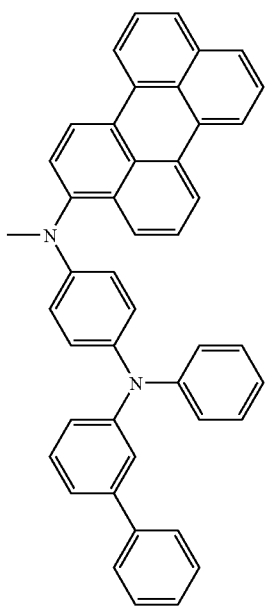
151
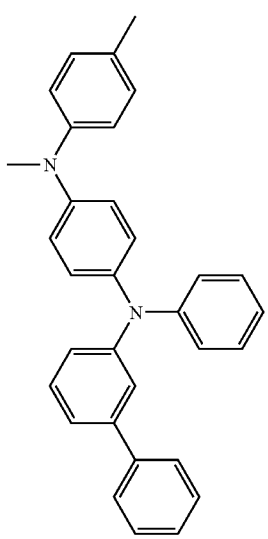
152
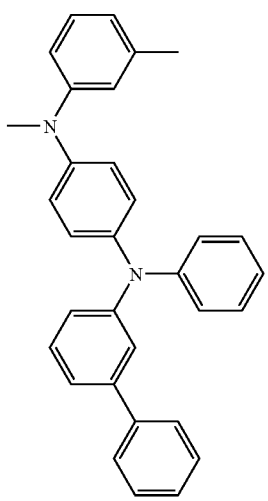
-continued
153
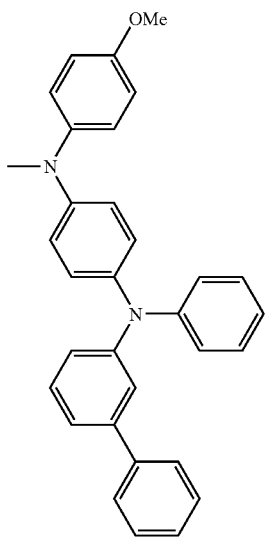
154
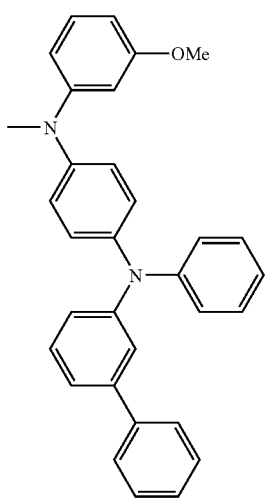
155
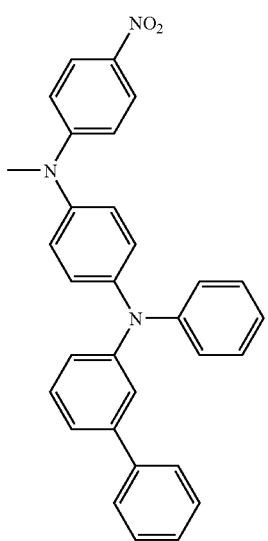

-continued
156
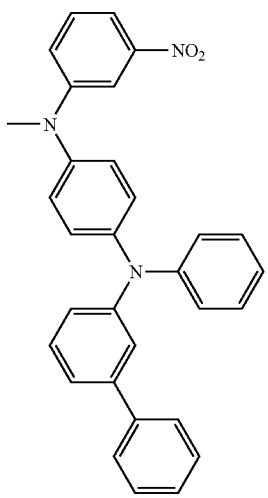
157
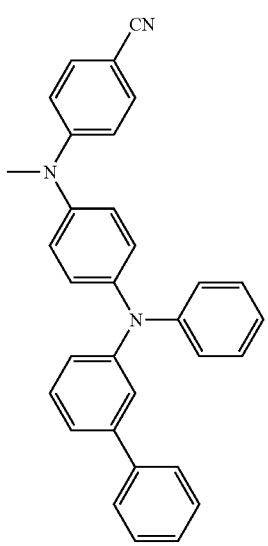
158
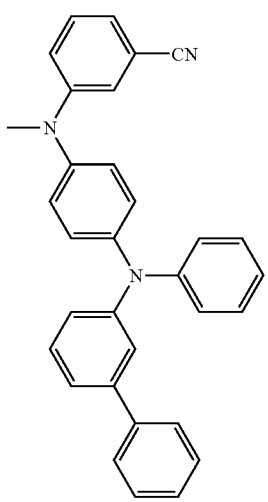
-continued
159
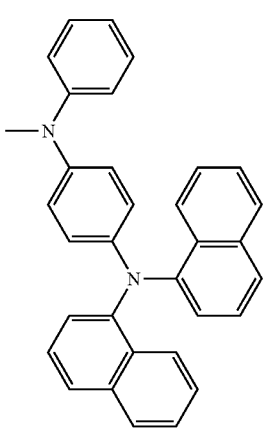
160
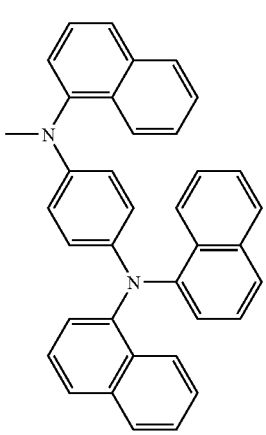
161
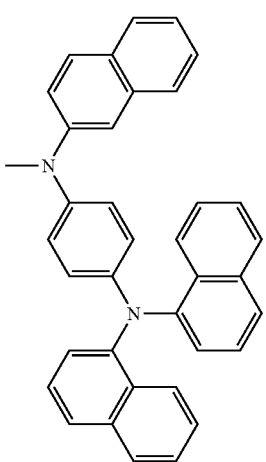

-continued
162
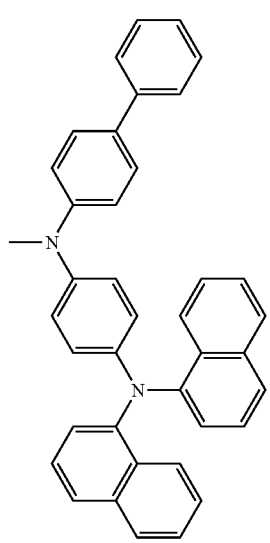
163
165
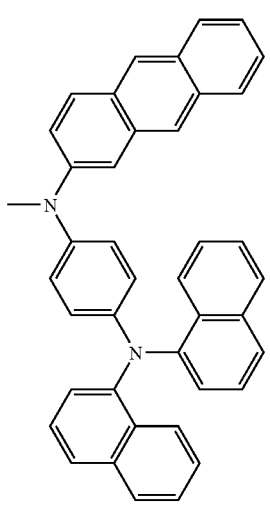
166
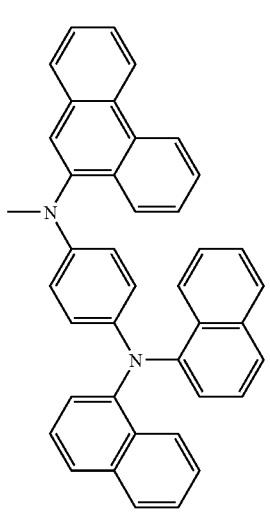
164
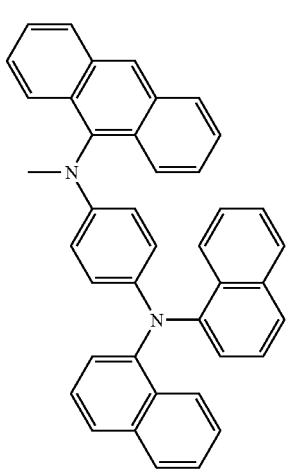
167

-continued
168
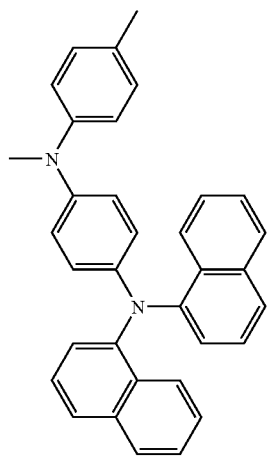
169
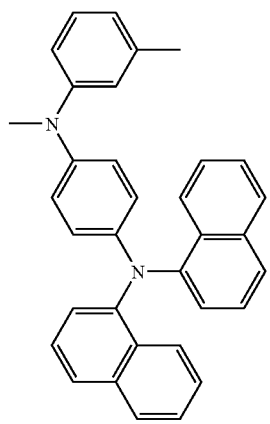
170
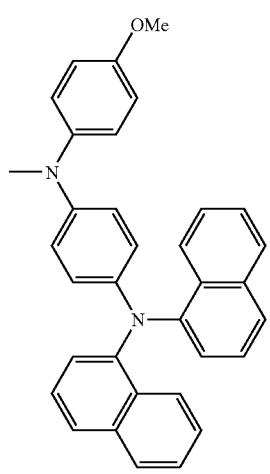
-continued
171
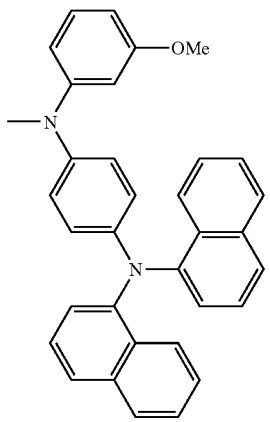
172
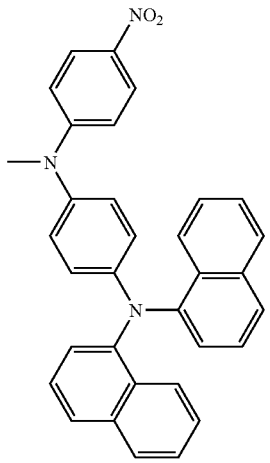
173
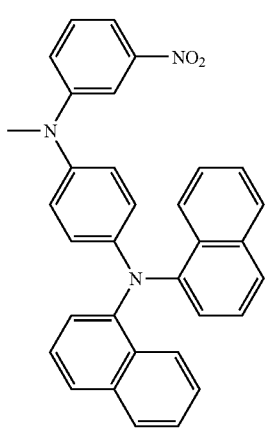

-continued
174
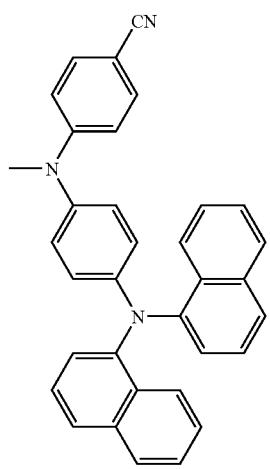
175
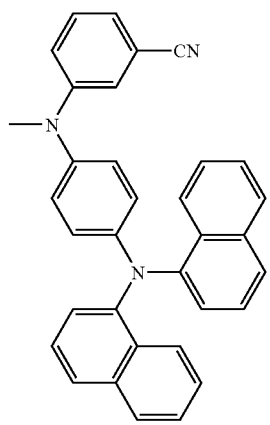
176
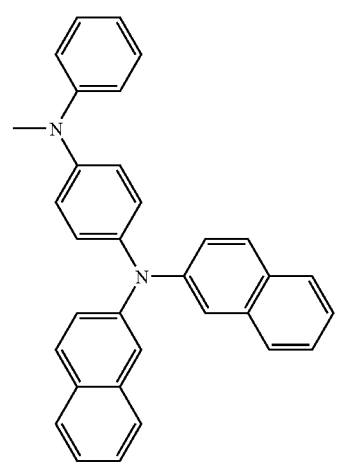
-continued
177
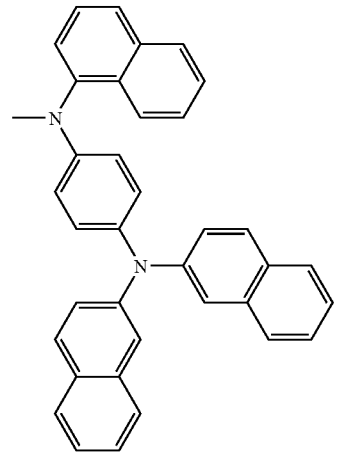
178
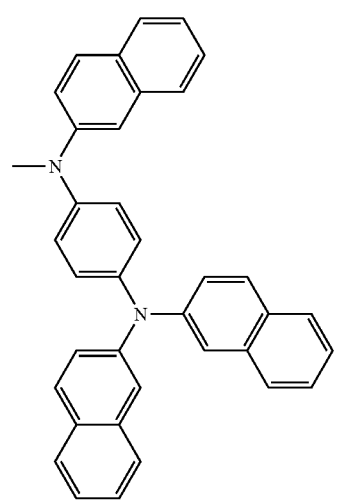
179
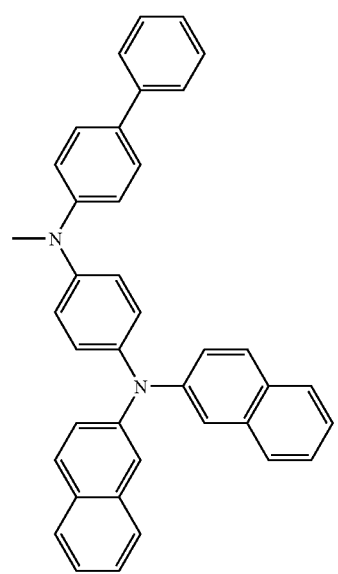

180
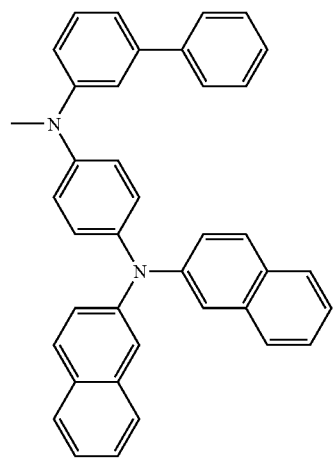
181
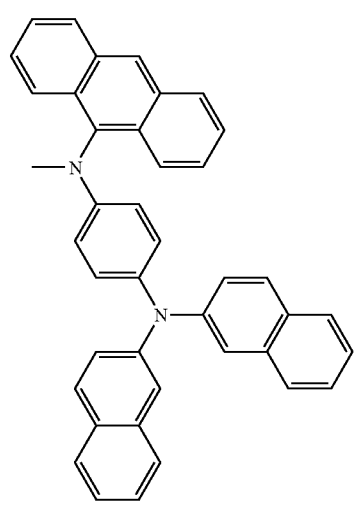
182
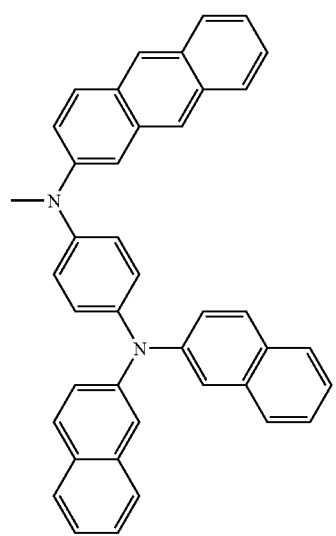
183
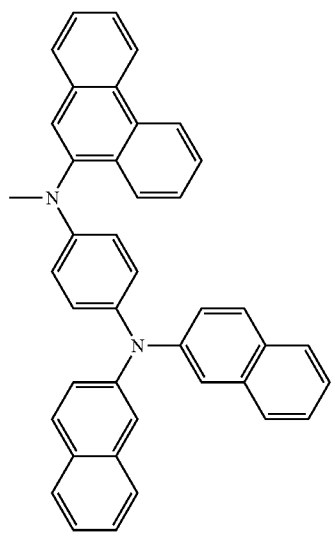
184
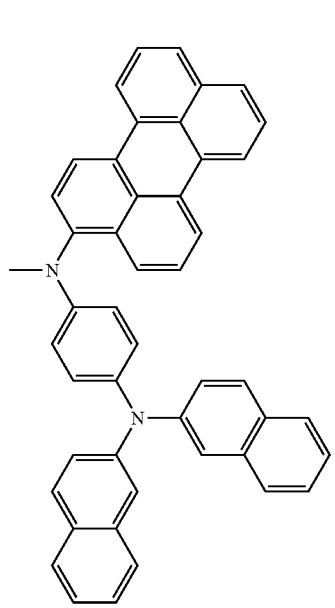
185
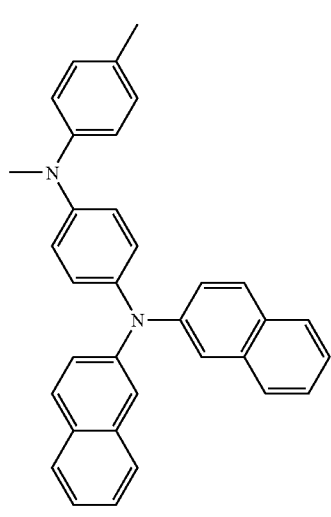

-continued
186
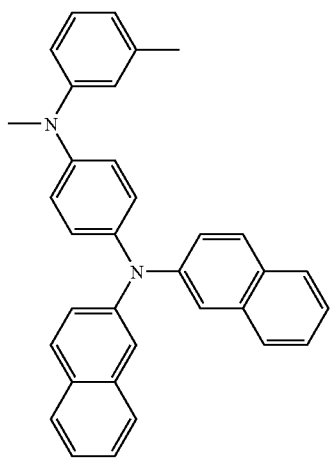
189
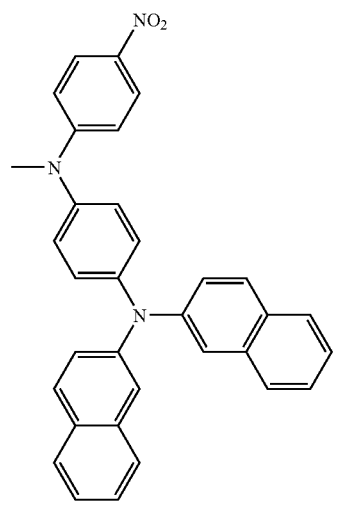
187
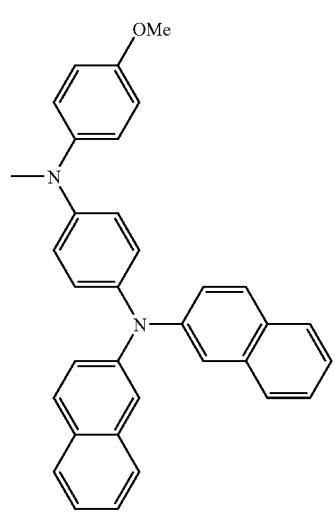
190
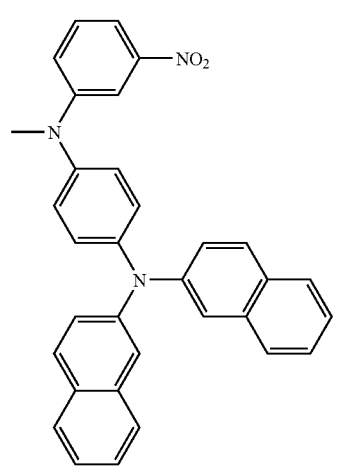
188
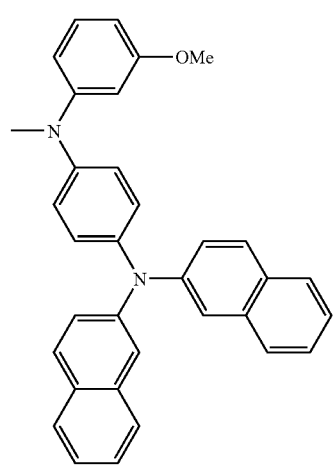
191
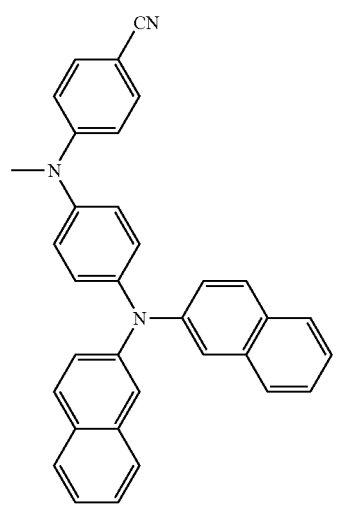

192
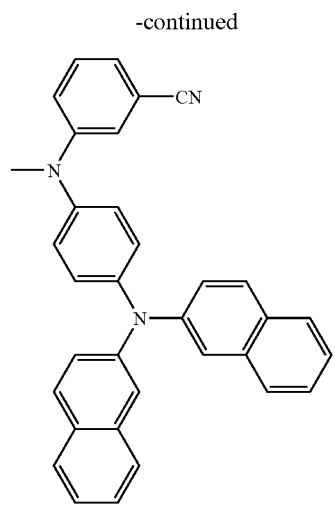
195
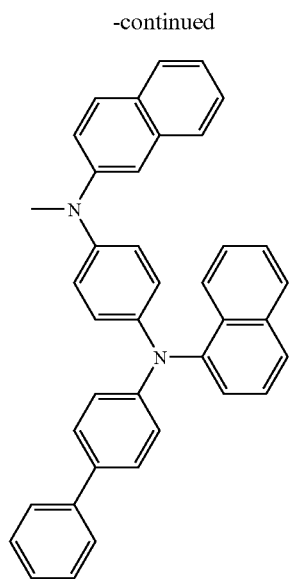
193
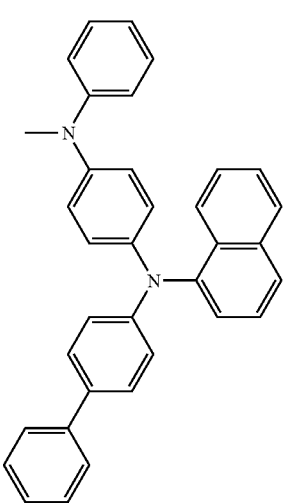
196
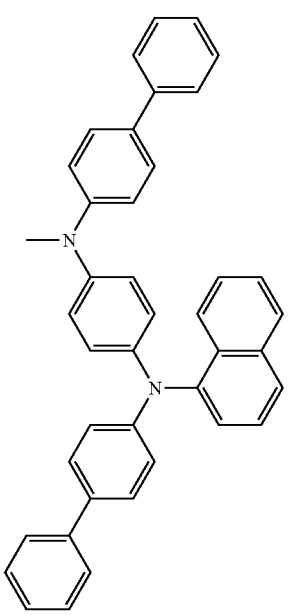
194
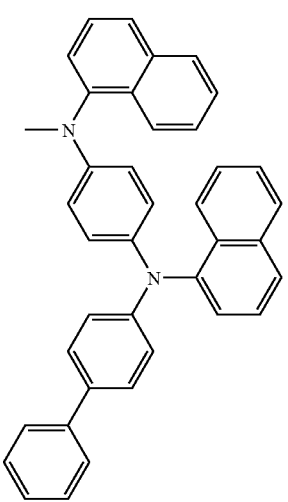
197
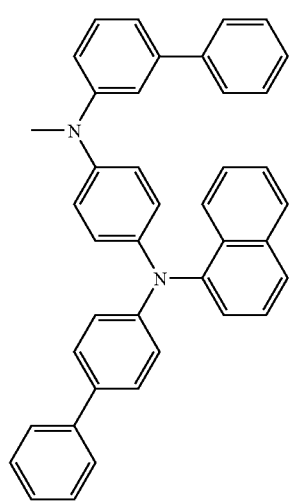

-continued
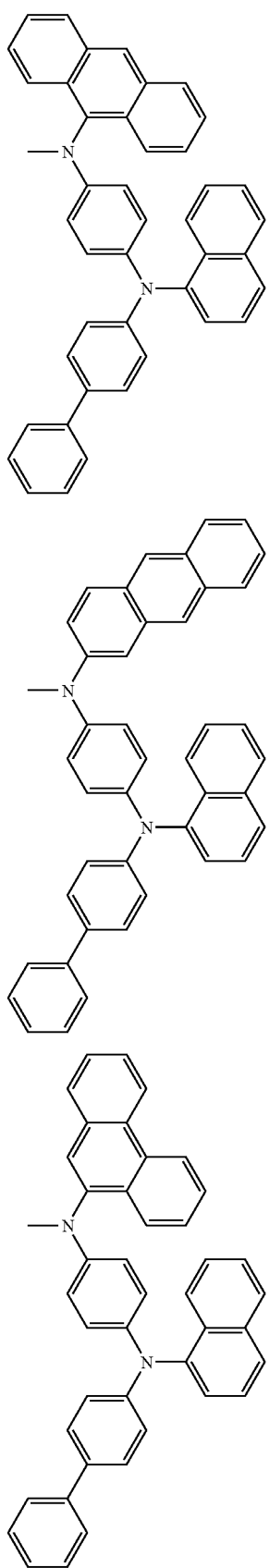
198
199
200
-continued
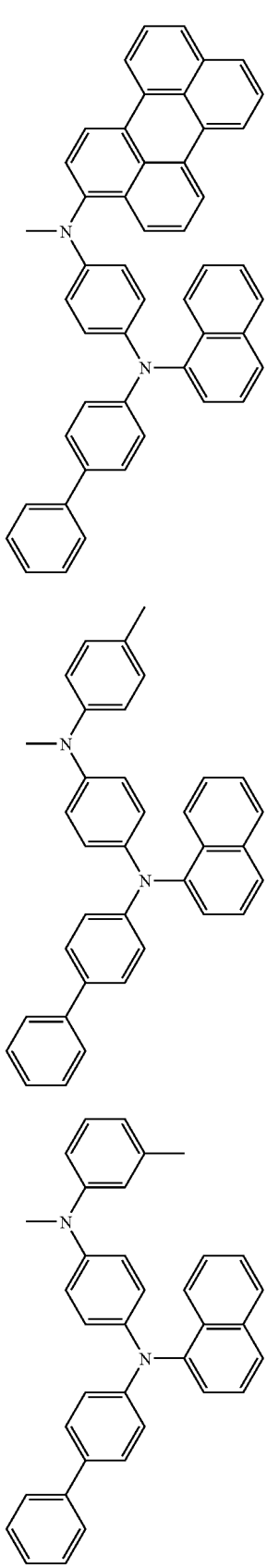
201
202
203

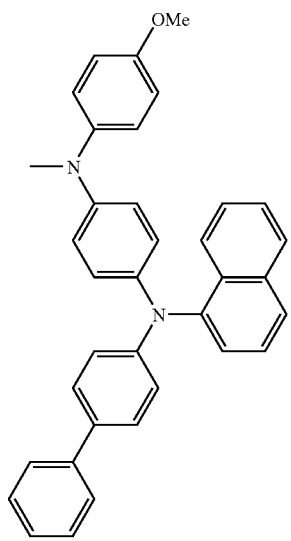
204
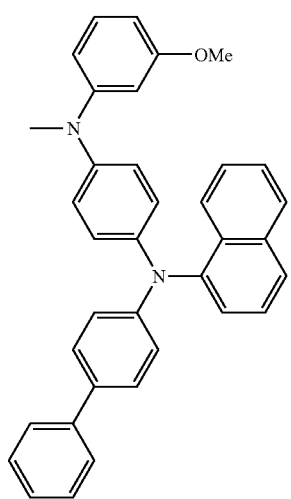
205
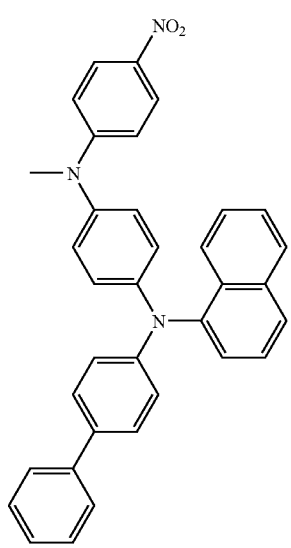
206
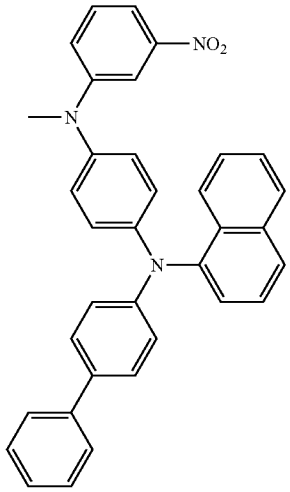
207
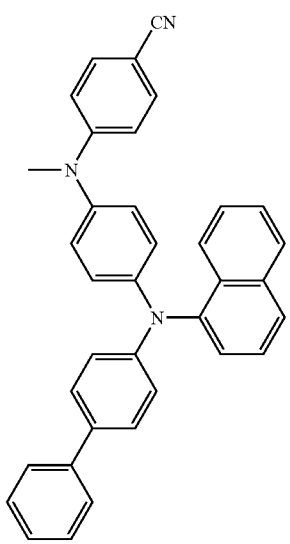
208
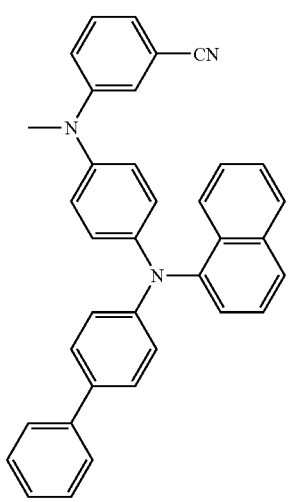
209

-continued
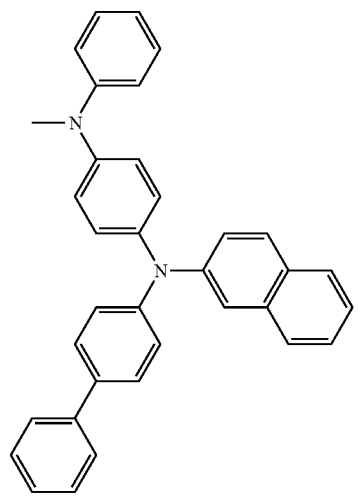
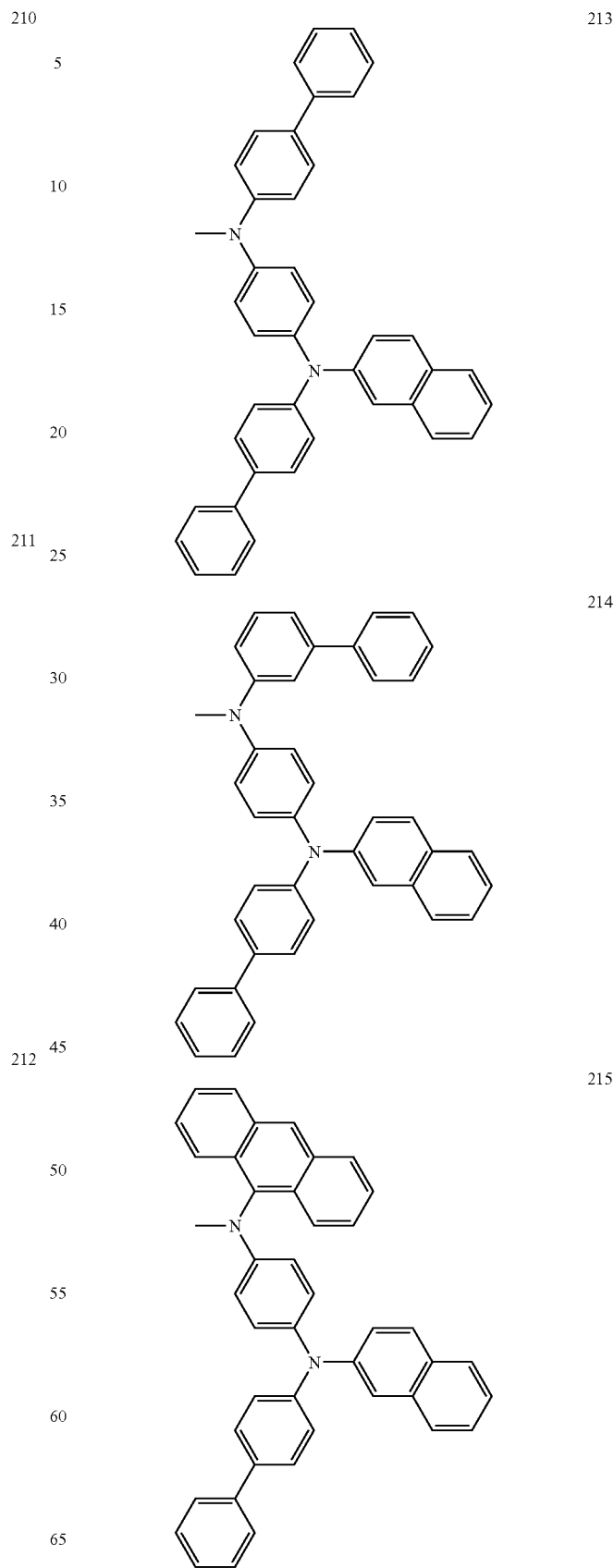

216
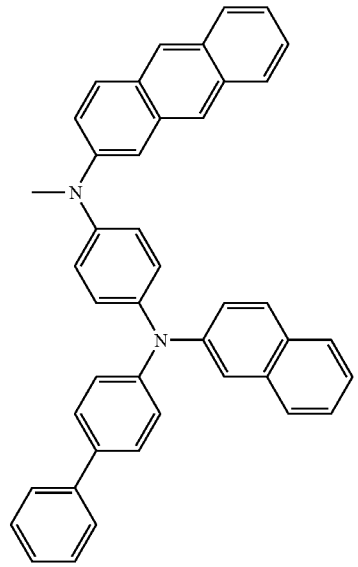
217
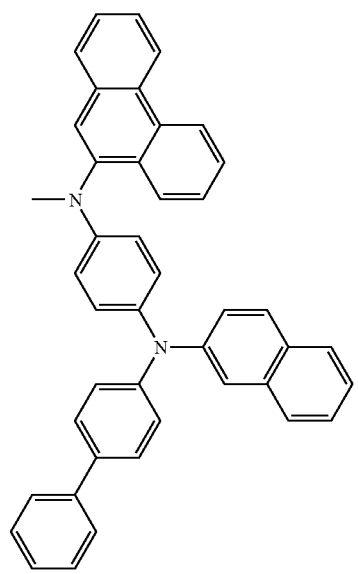
218
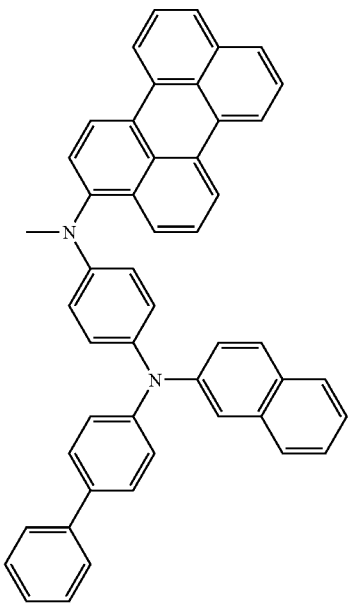
219
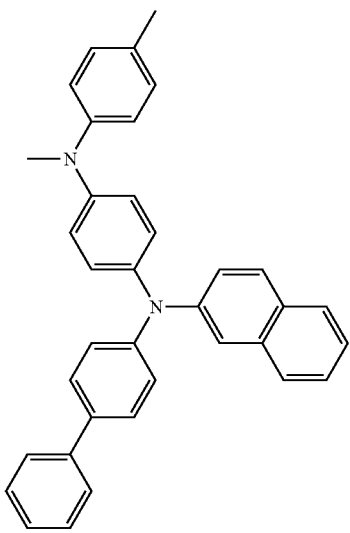
220
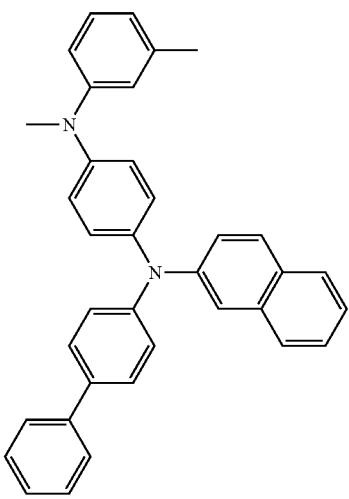

221 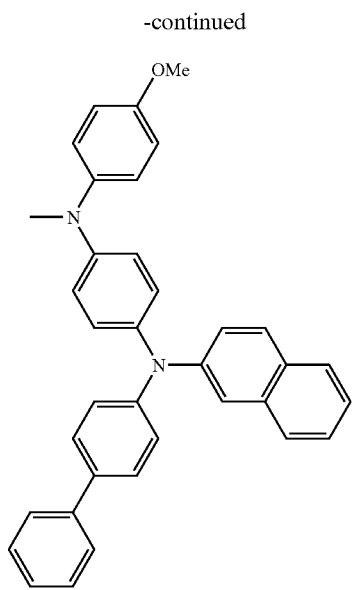
222 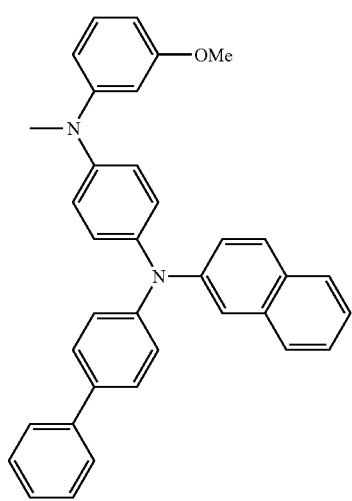
223 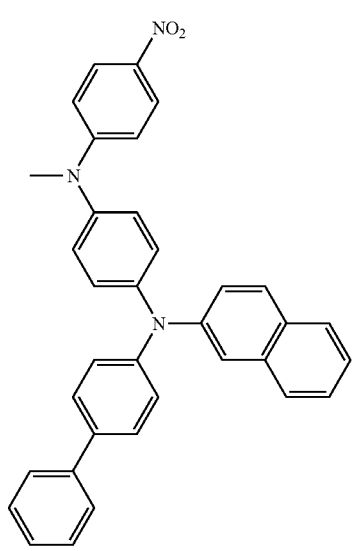
224 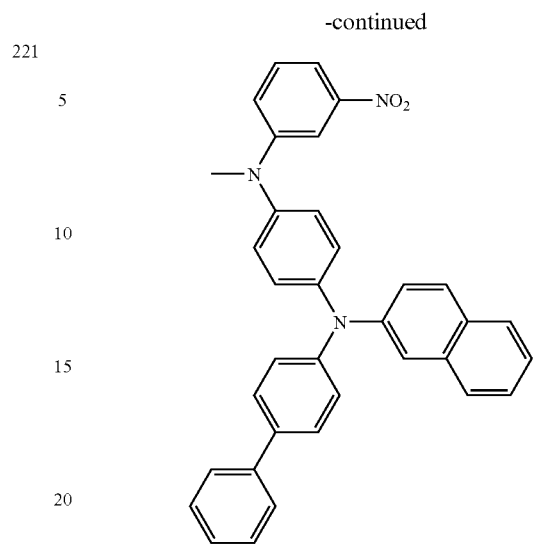
225 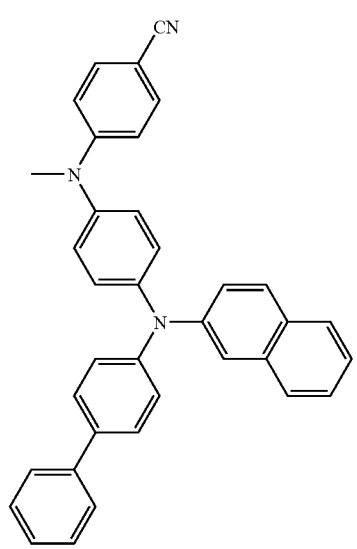
226 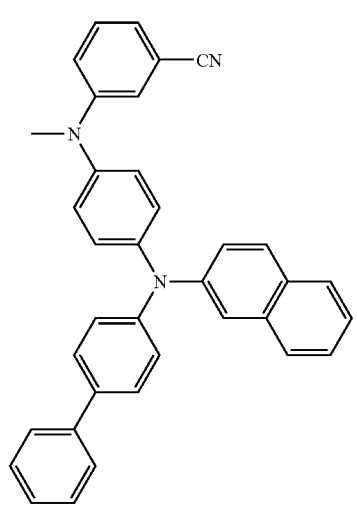

227
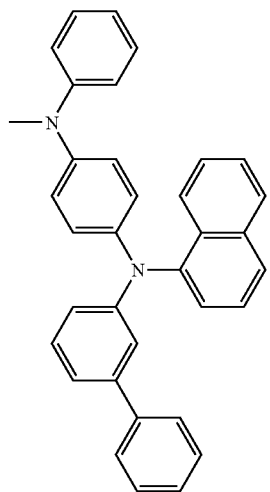
228
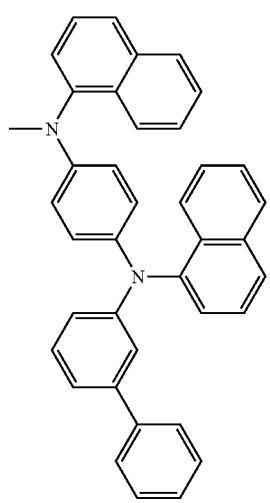
229
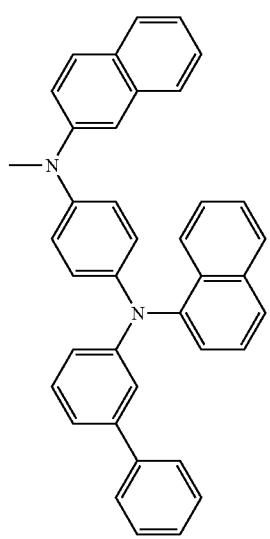
230
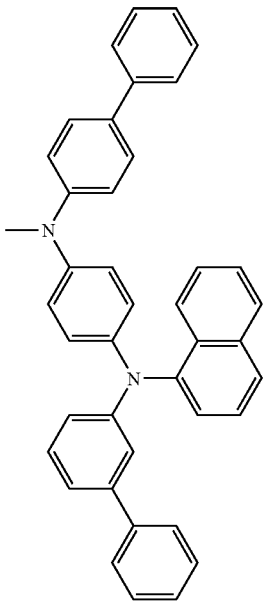
231
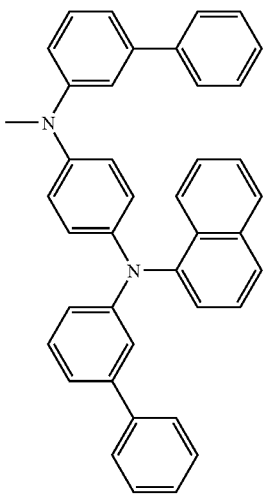
232
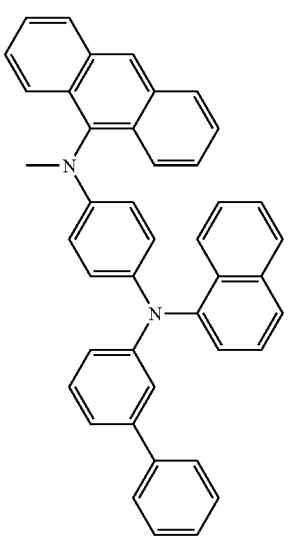

233
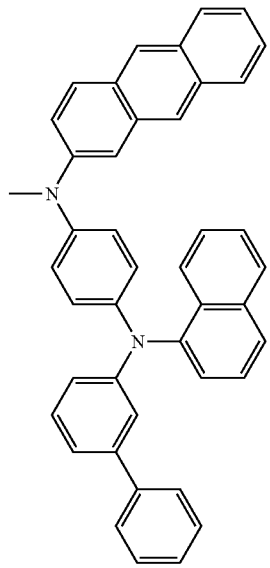
234
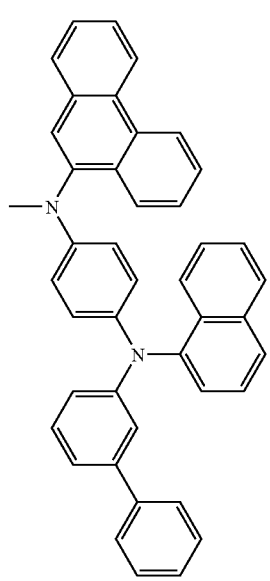
235
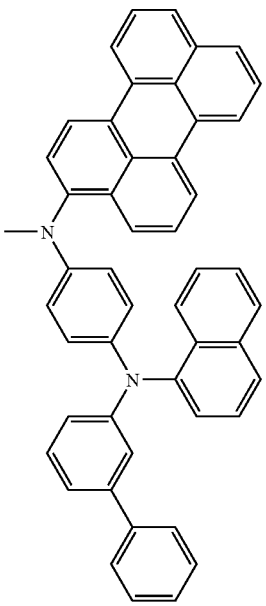
236
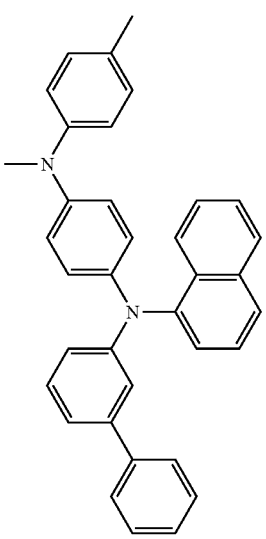
237
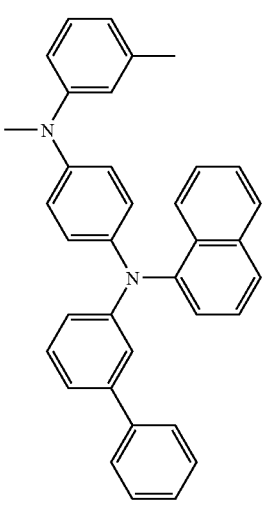

238
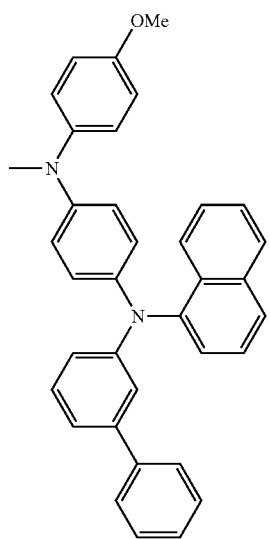
239
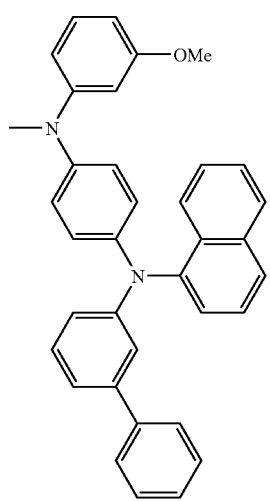
240
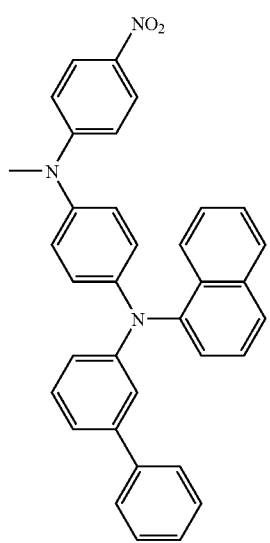
241
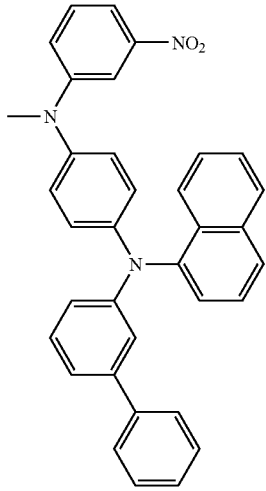
242
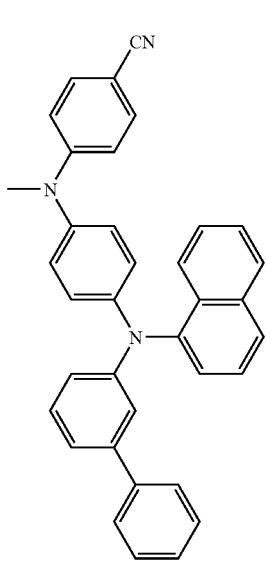
243
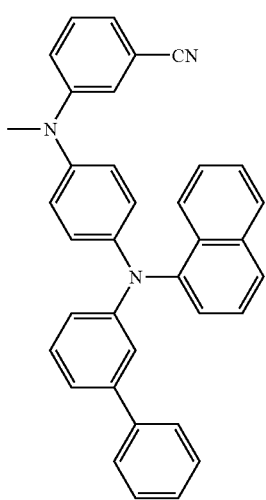

-continued
244
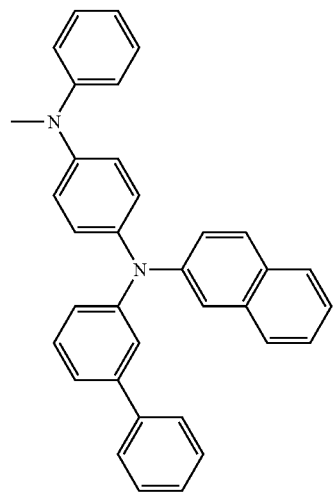
245
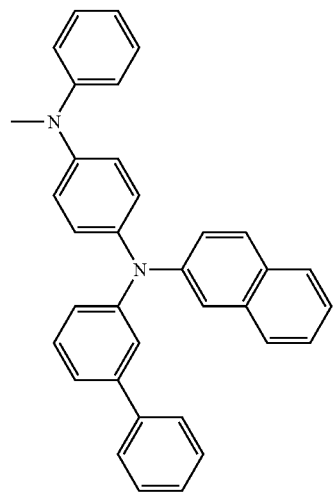
246
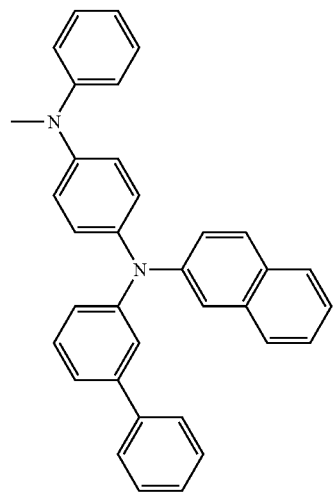
-continued
247
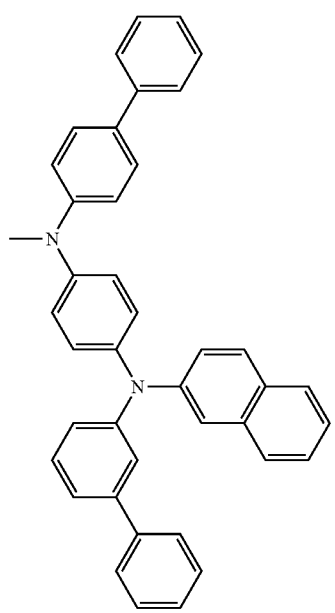
248
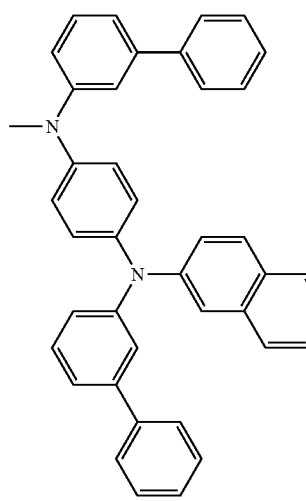
249
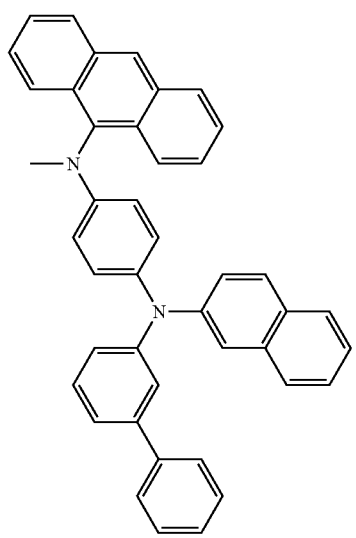

-continued
250
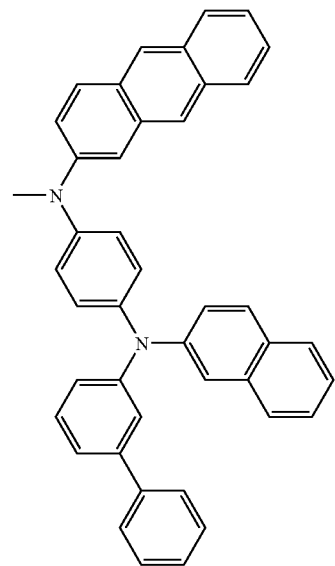
251
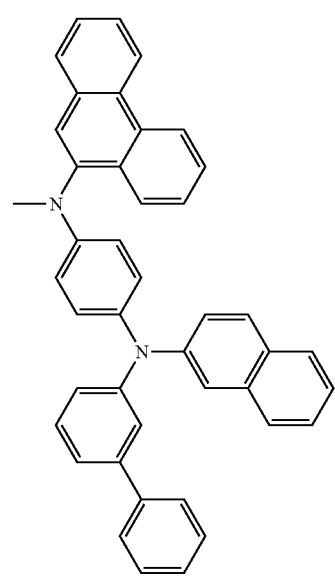
252
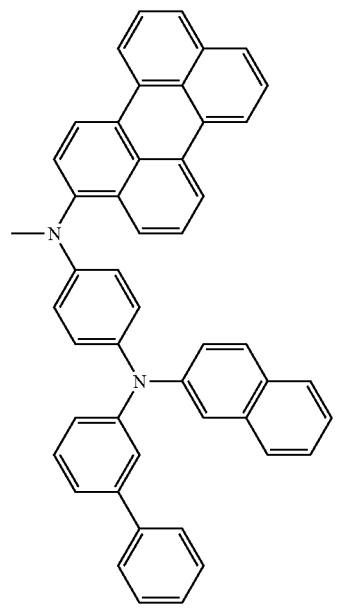
253
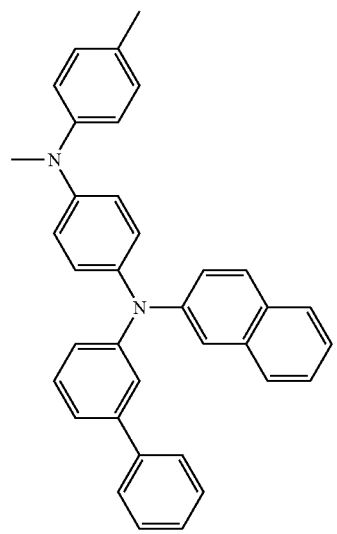
254
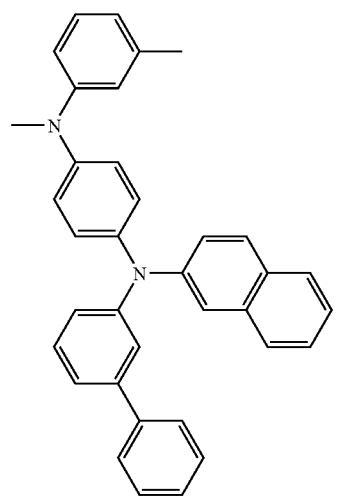

-continued
255 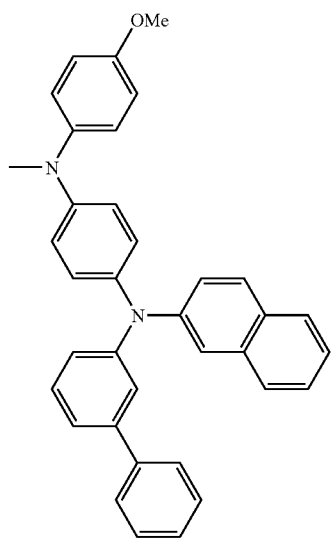
256 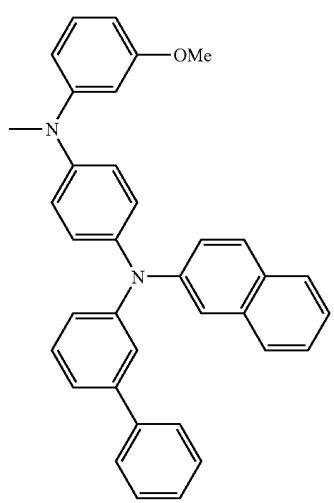
257 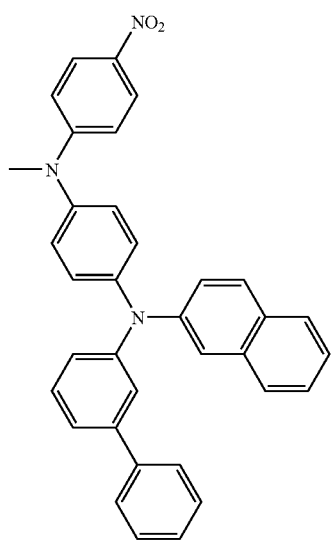
-continued
258 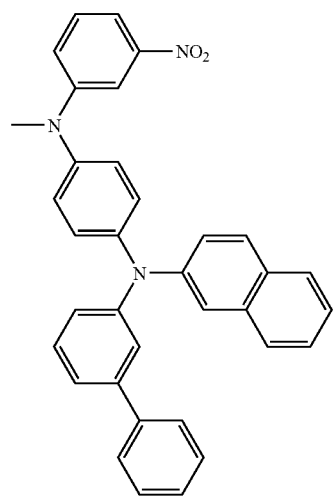
259 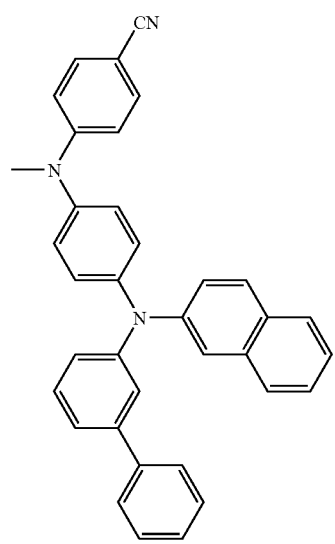
260 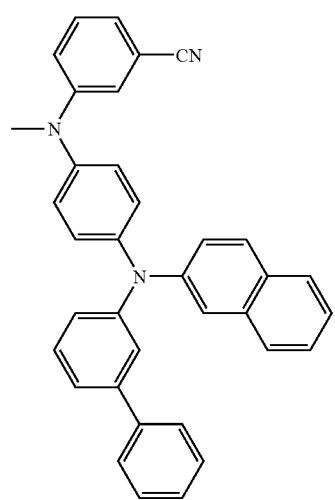

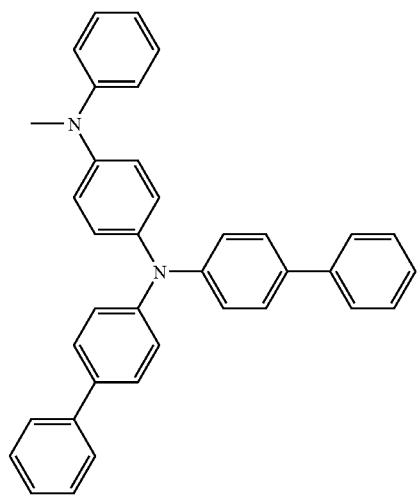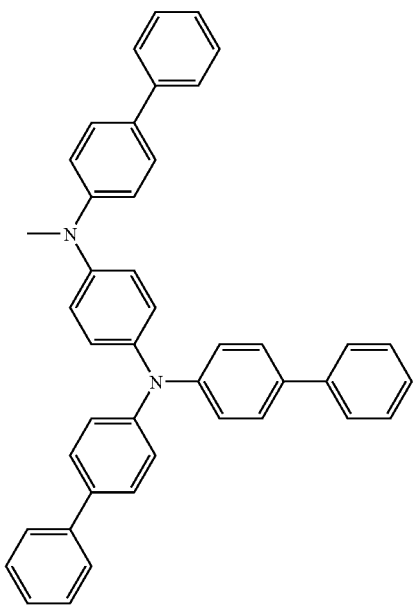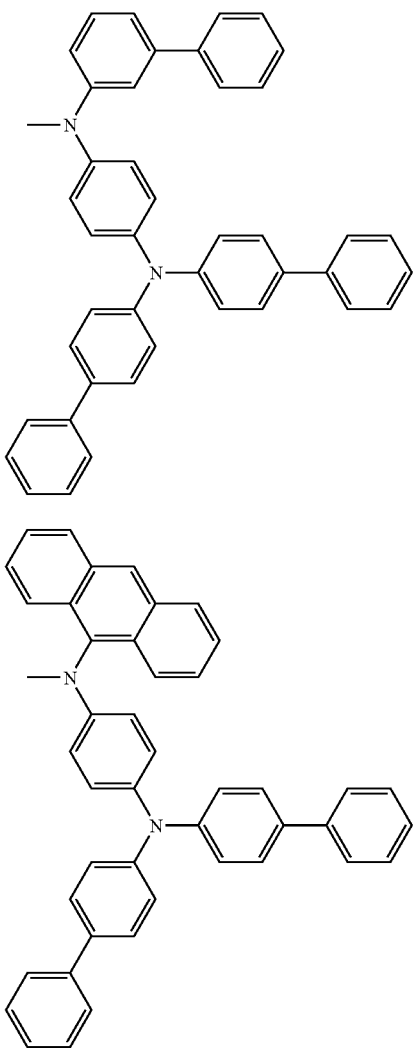

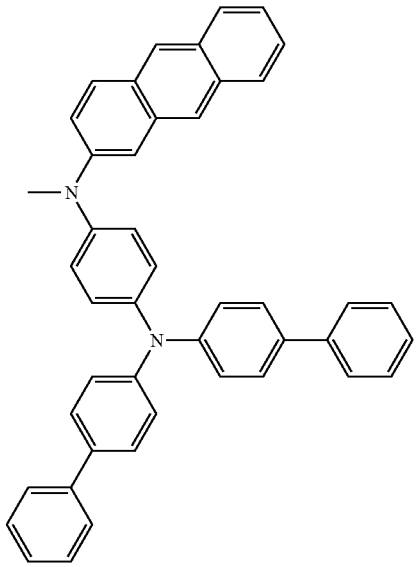
267
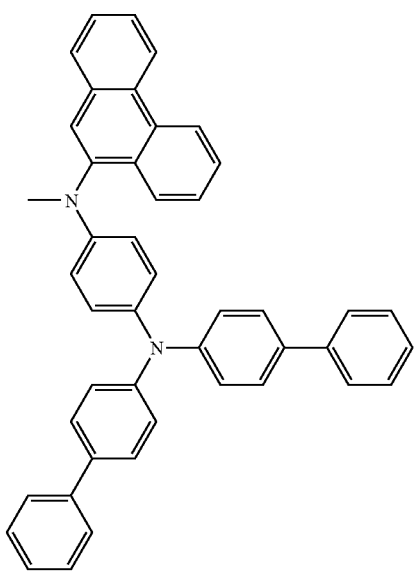
268
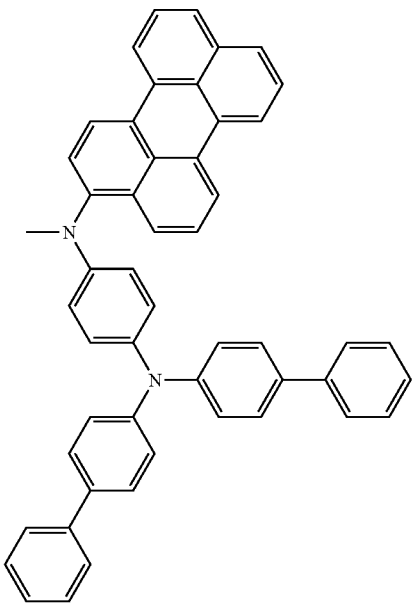
269
270
271

-continued
272
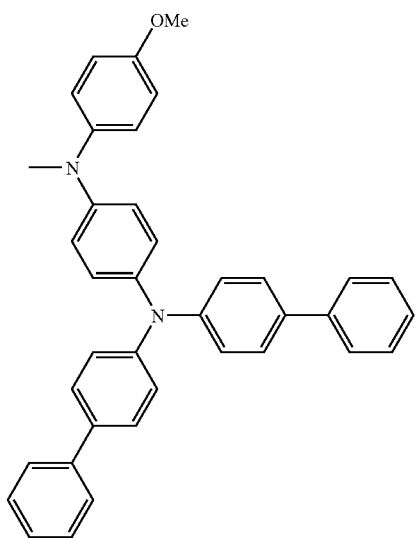
273
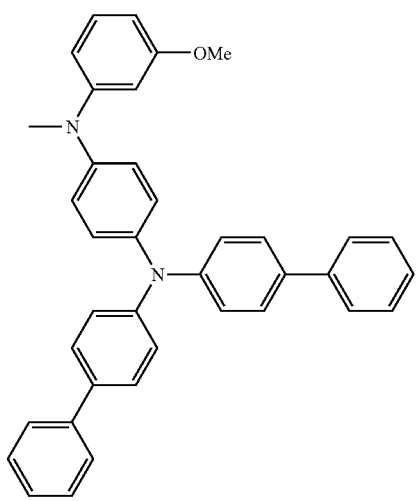
274
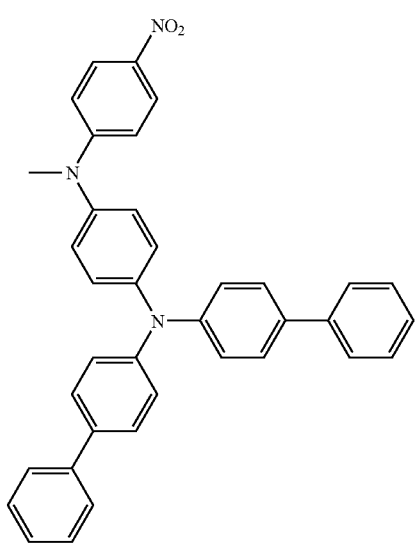
-continued
275
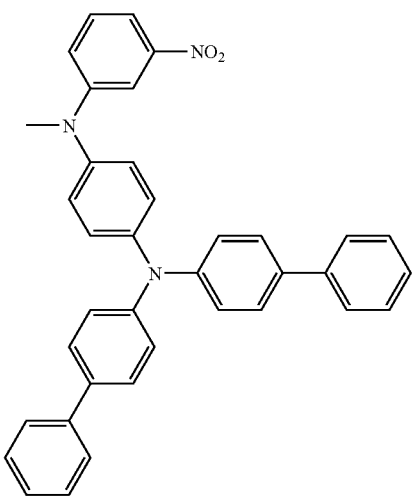
276
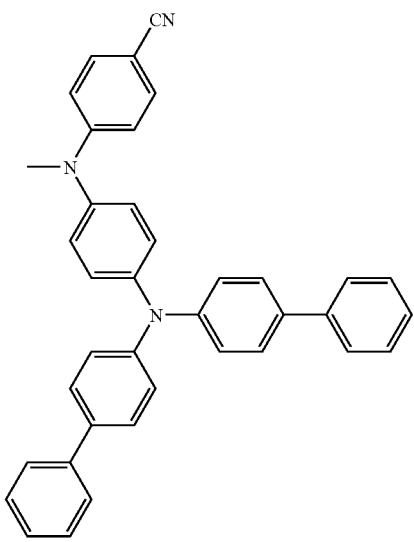
277
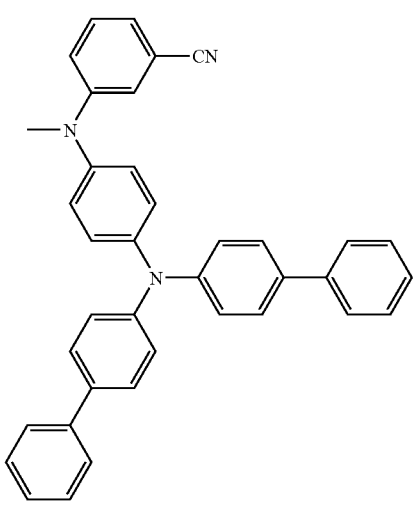

278
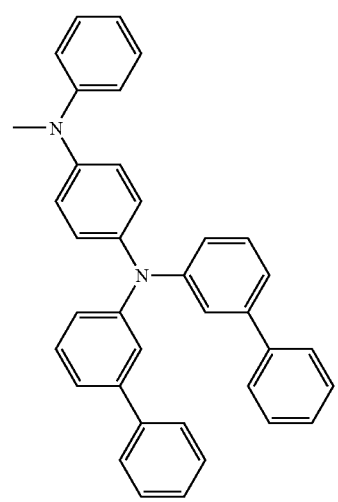
279
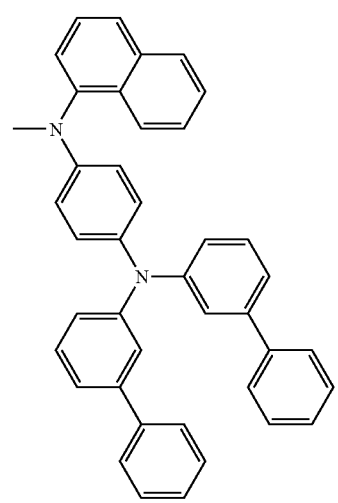
280
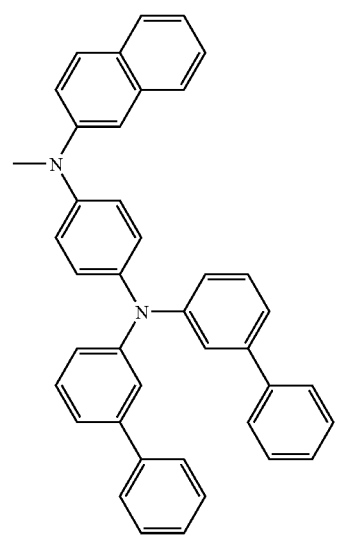
281
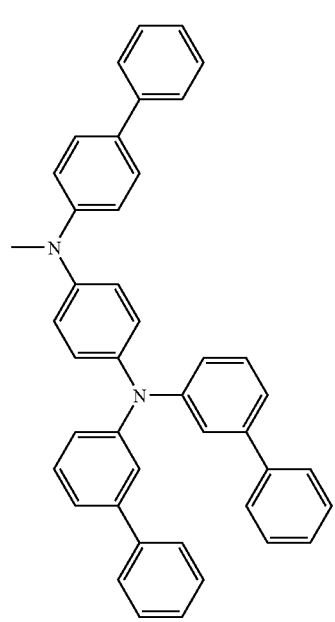
282
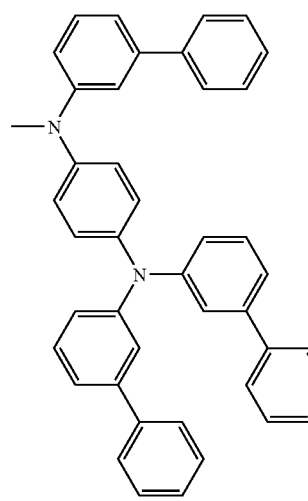
283
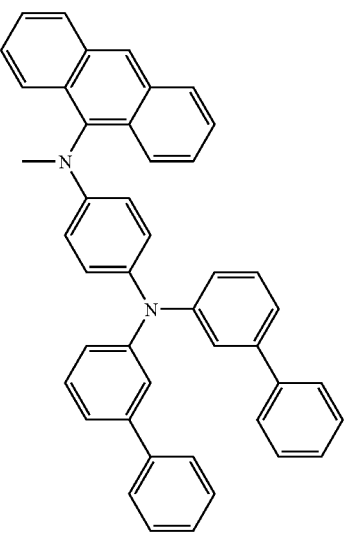

91
-continued
284
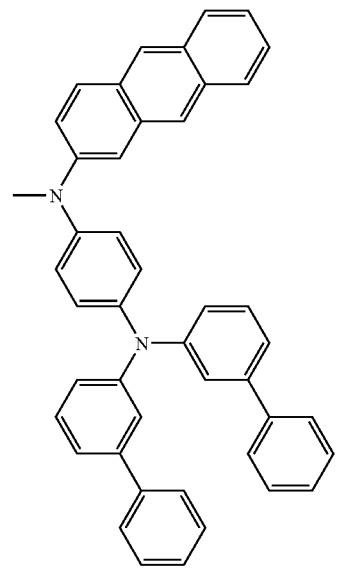
285
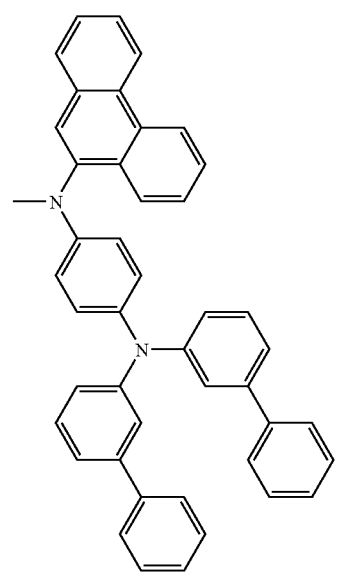
92
-continued
286
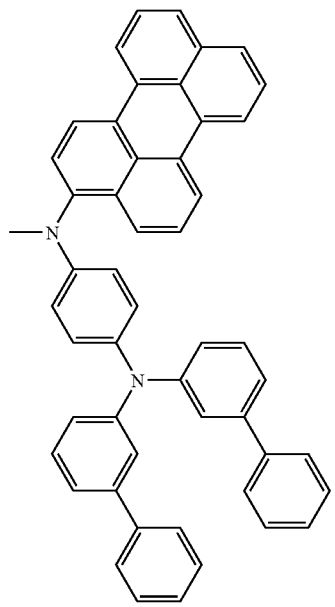
287
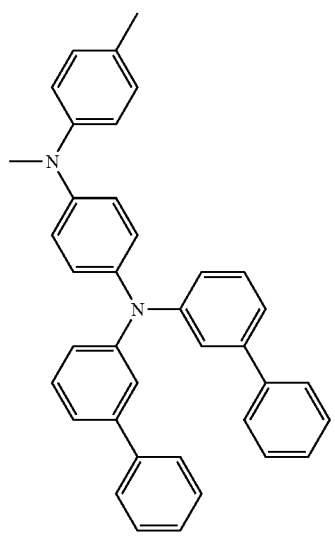
288
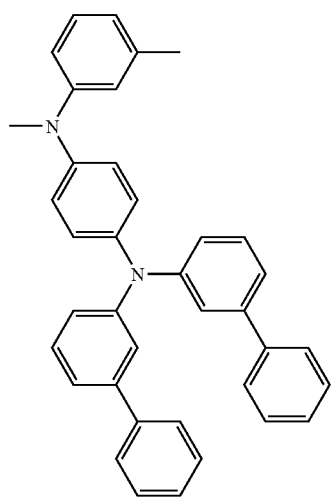

-continued

289

290

291

292

293

294

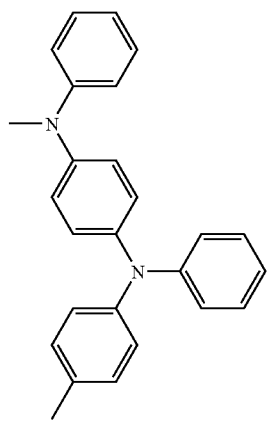
295
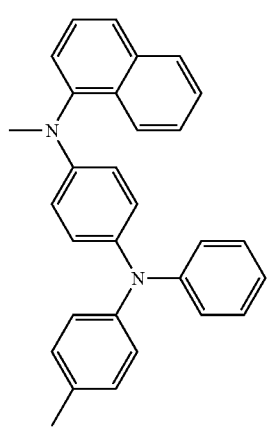
296
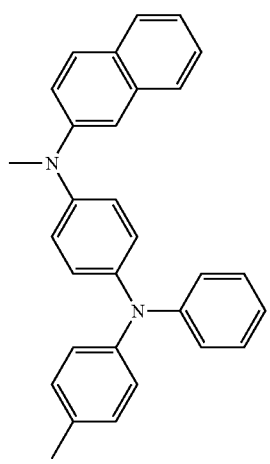
297
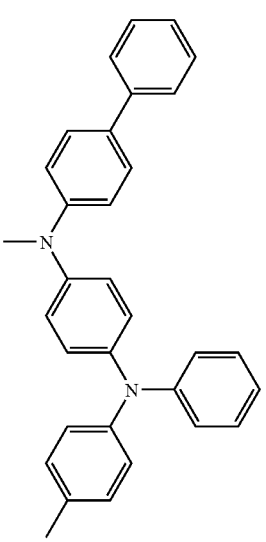
298
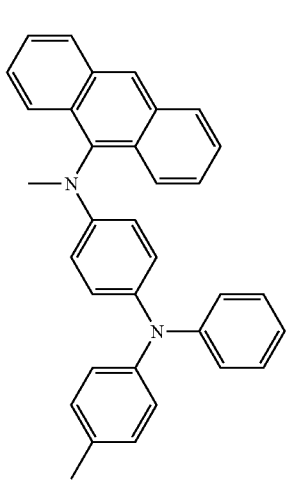
299
300

-continued
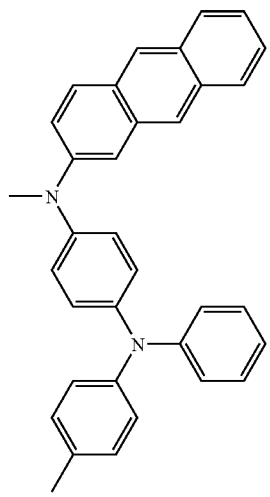
301
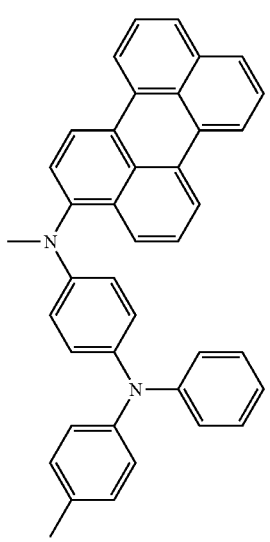
303
302
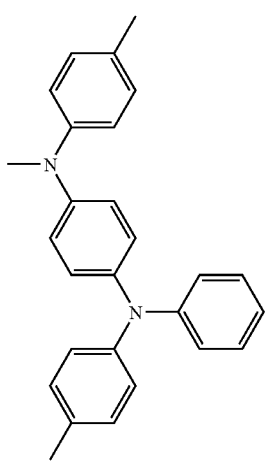
304
302
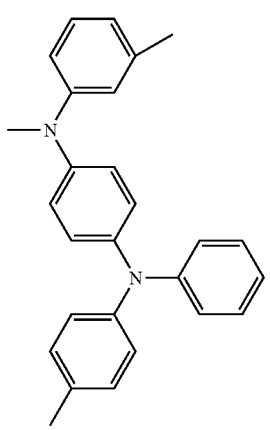
305

-continued
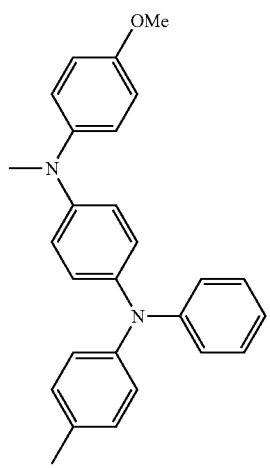
306
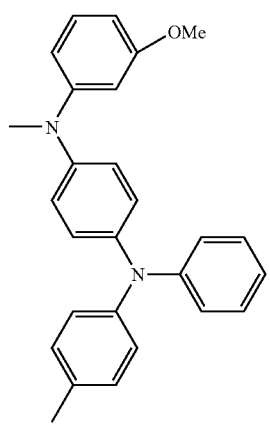
307
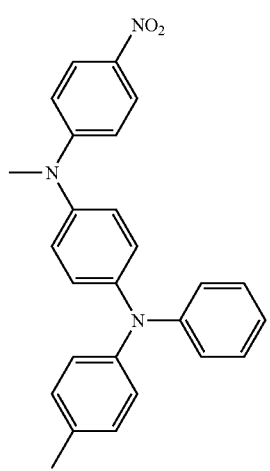
308
-continued
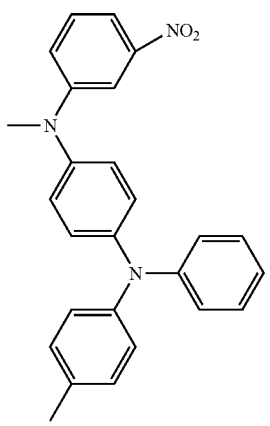
309
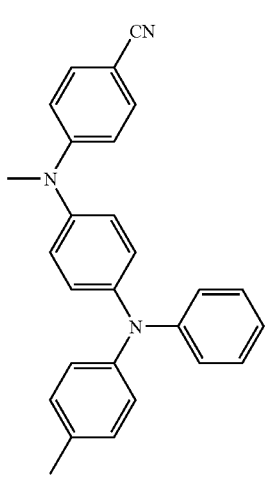
310
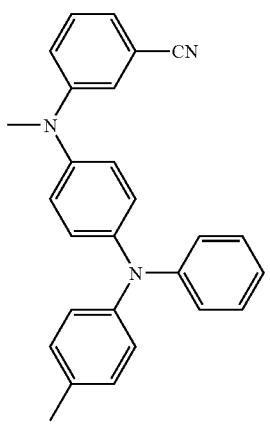
311

312
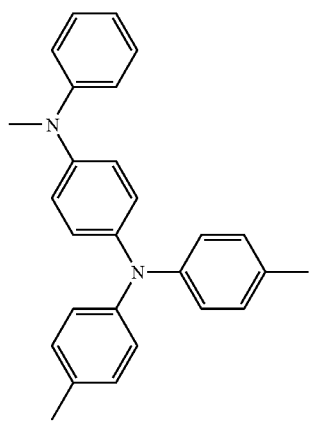
313
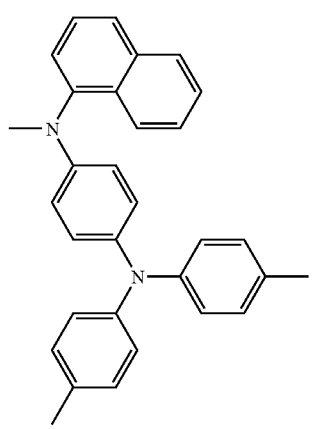
314
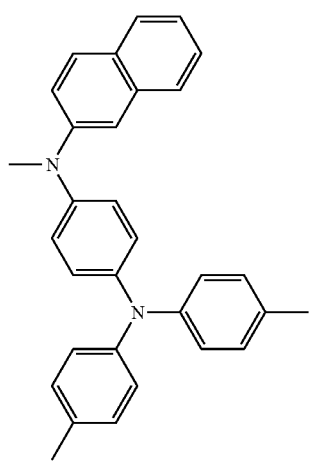
315
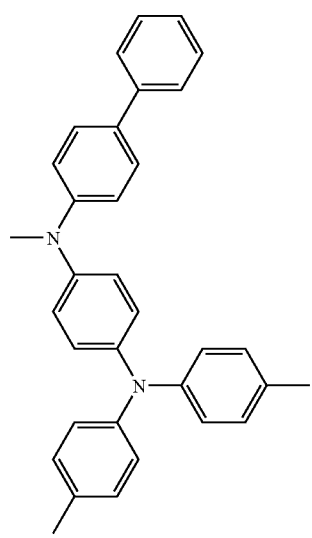
316
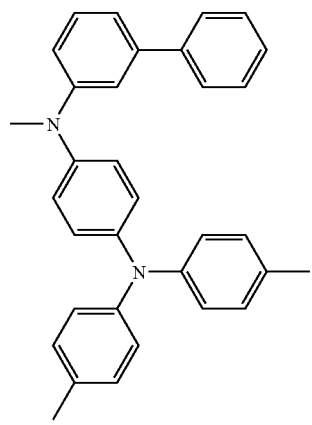
317
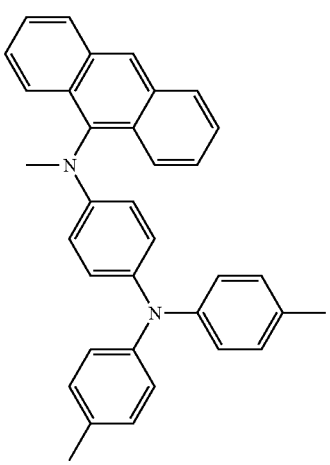

-continued
318
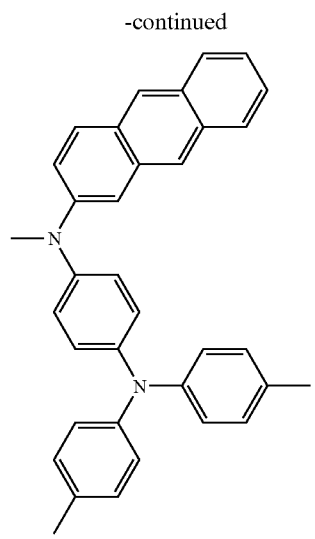
319
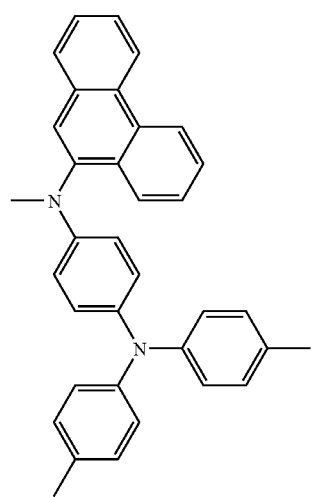
320
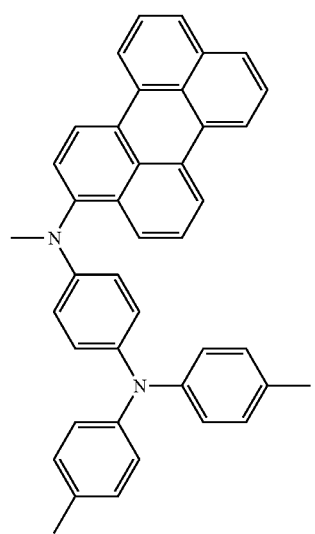
-continued
321
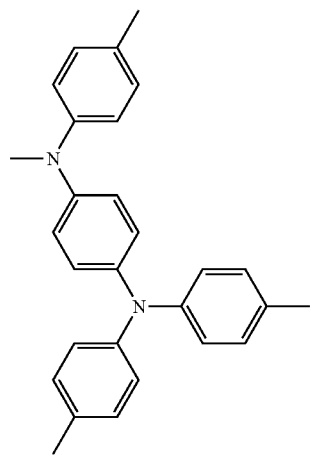
322
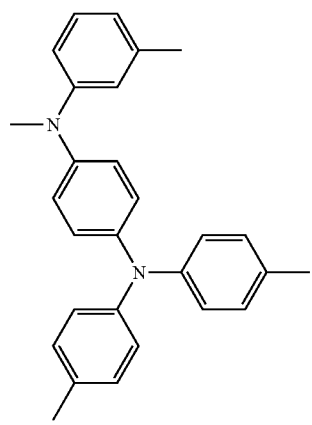
323
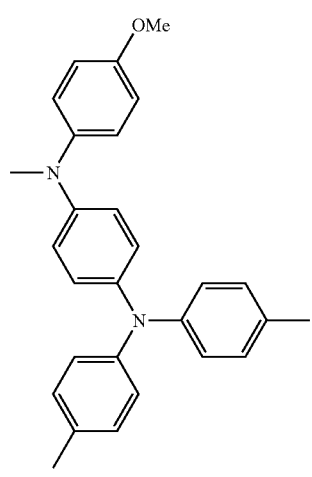

-continued
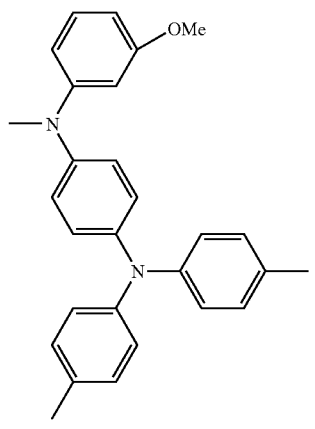
324
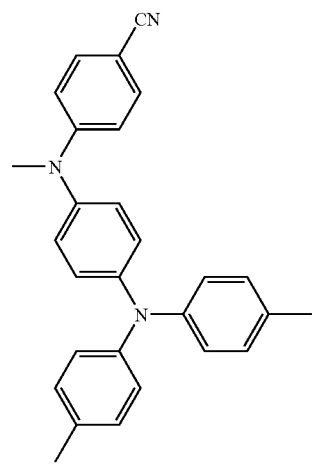
327
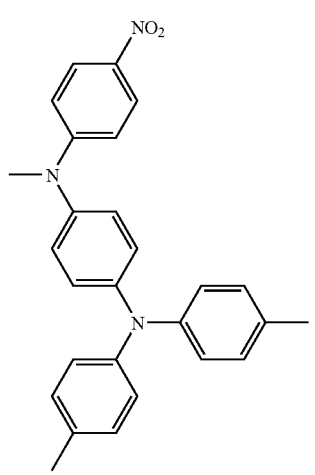
325
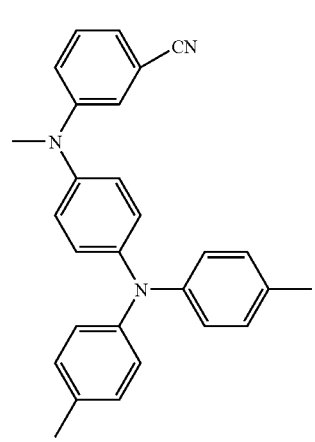
328
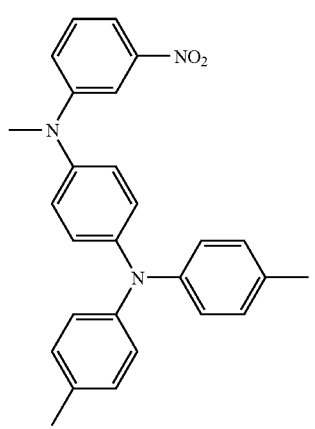
326
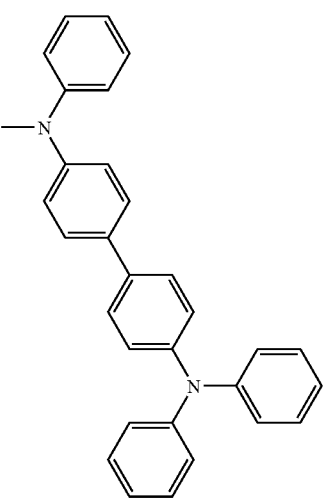
329

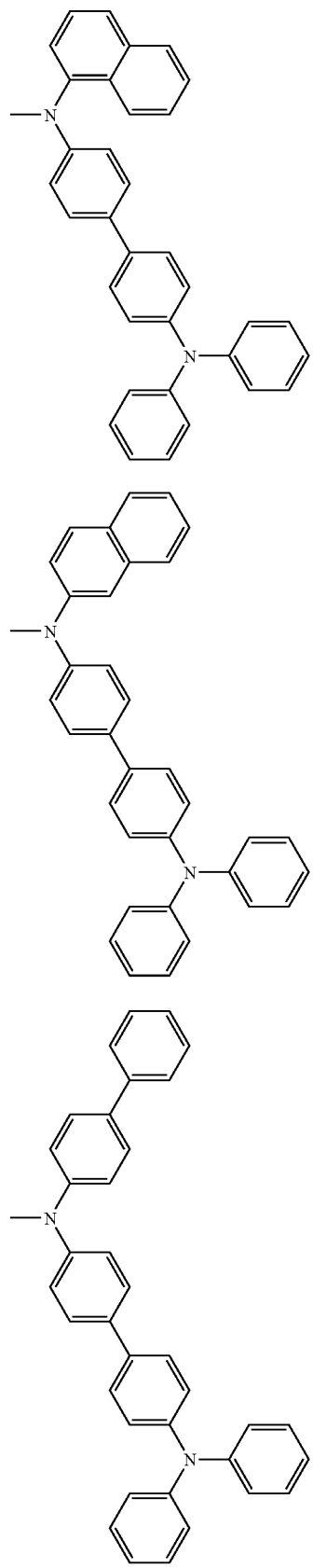
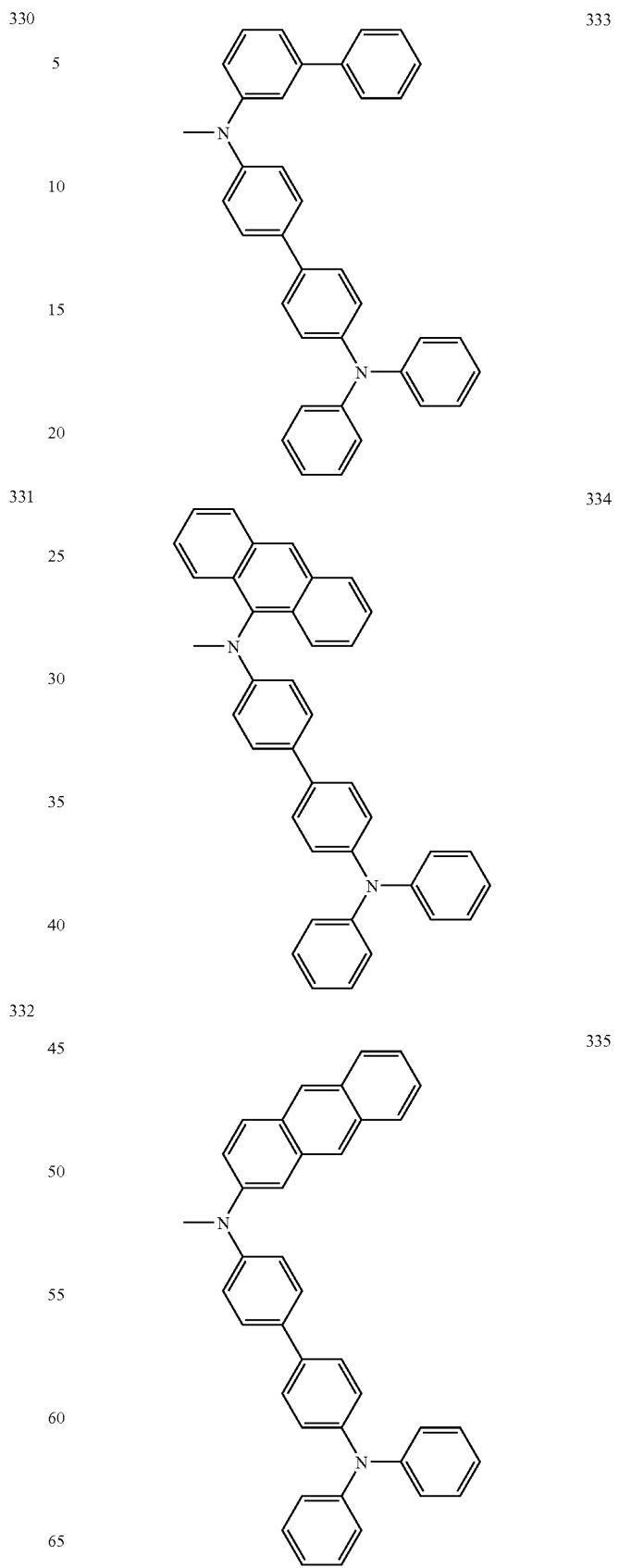

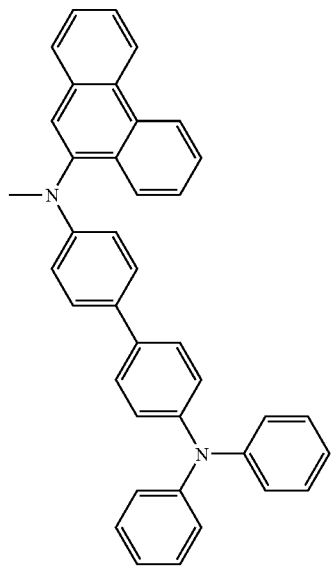 336
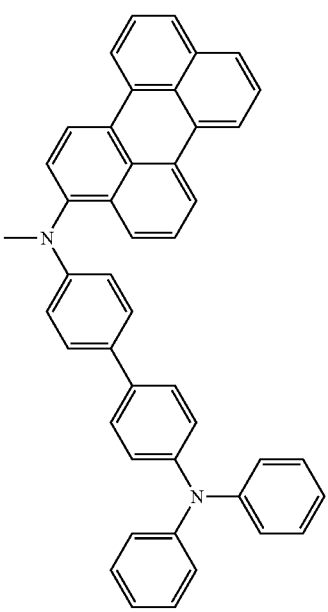 337
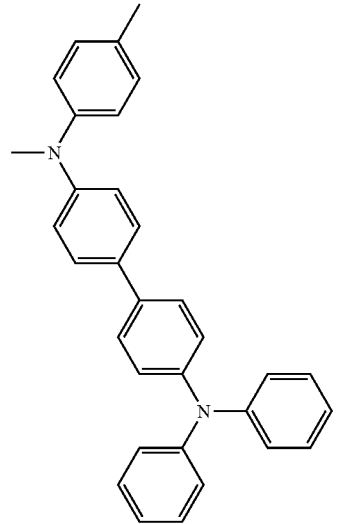 338
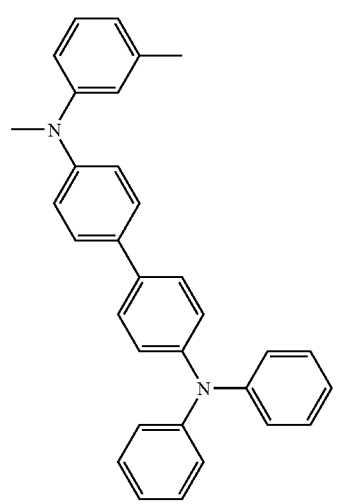 339
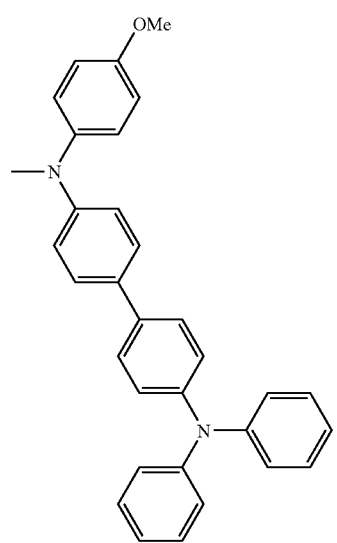 340

-continued
341
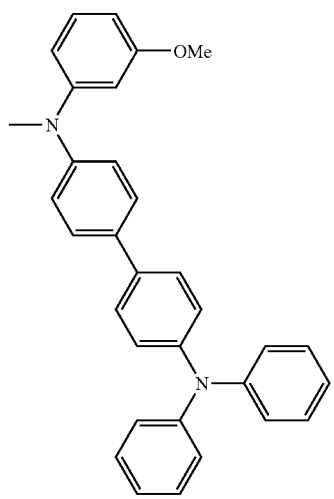
342
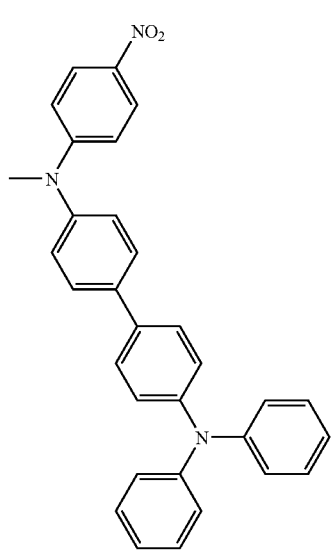
343
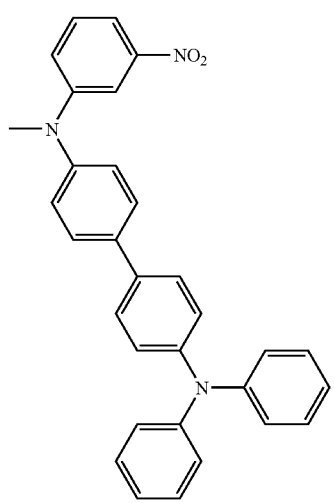
-continued
344
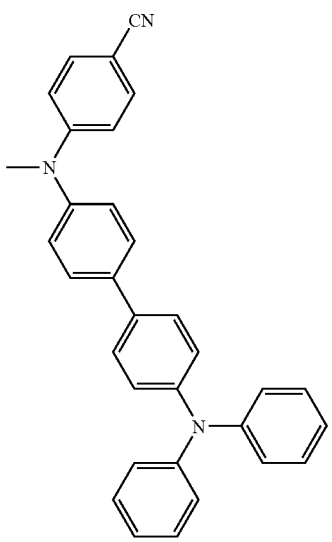
345
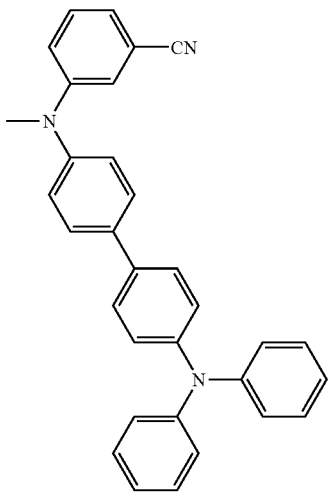

-continued
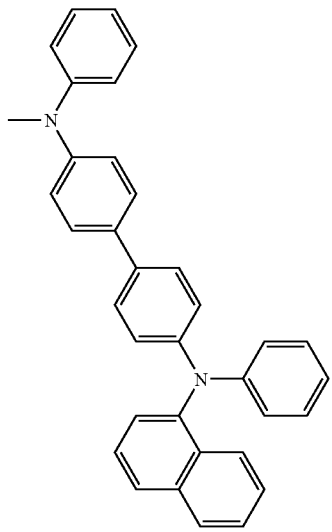
346
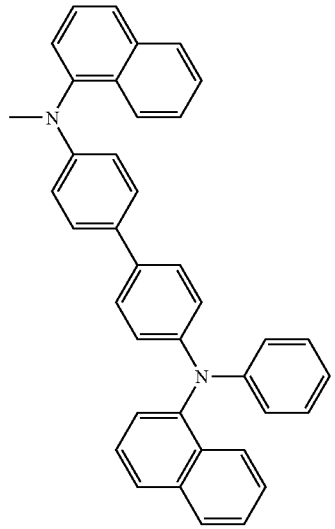
347
Illustrative, but non-limiting, examples of the compound of Formula 1 include compounds shown in the following Formulae.
[Formula 2]
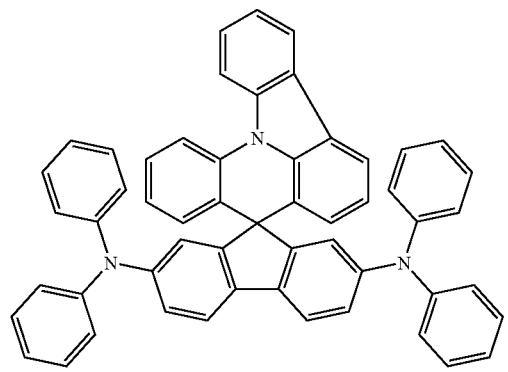
[Formula 3]
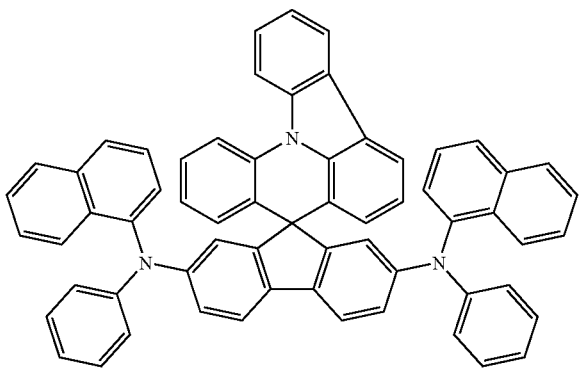
[Formula 4]
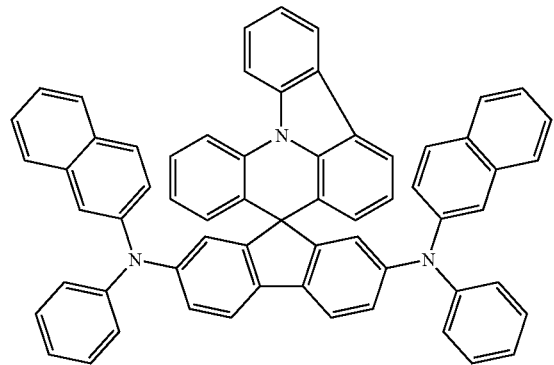
[Formula 5]
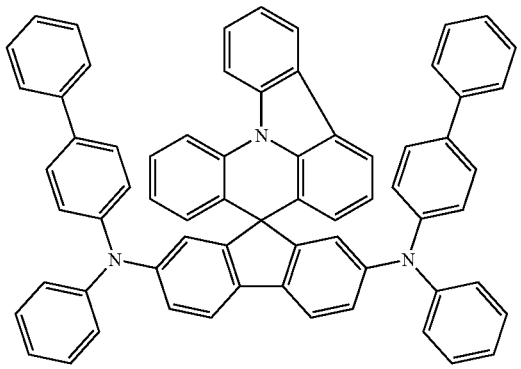

-continued
[Formula 6]
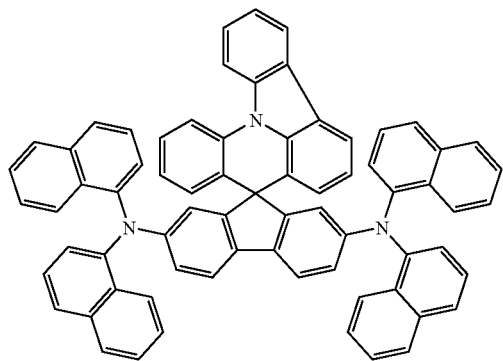
[Formula 7]
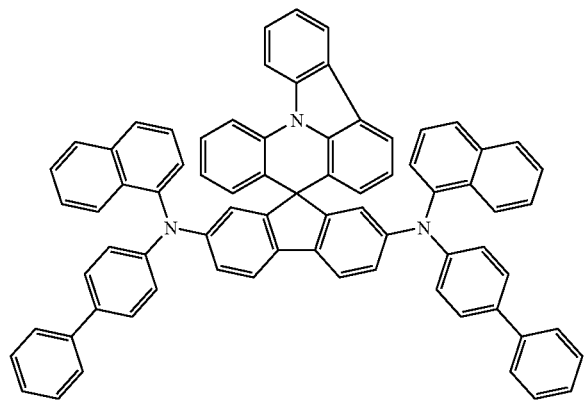
[Formula 8]
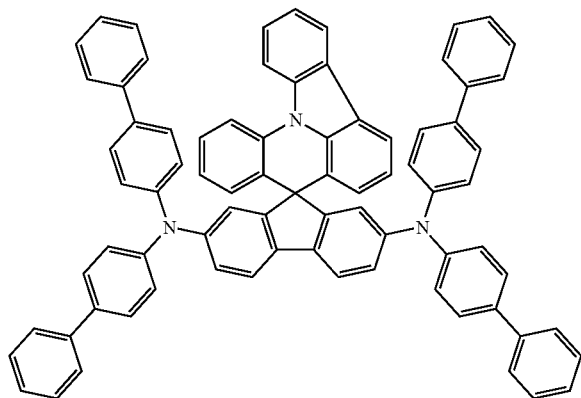
[Formula 9]
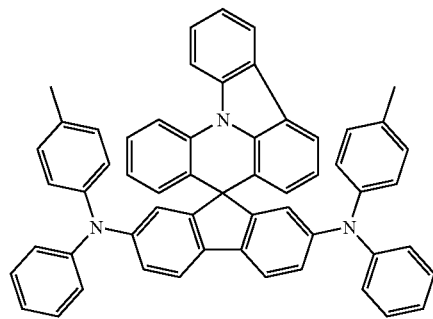
[Formula 10]
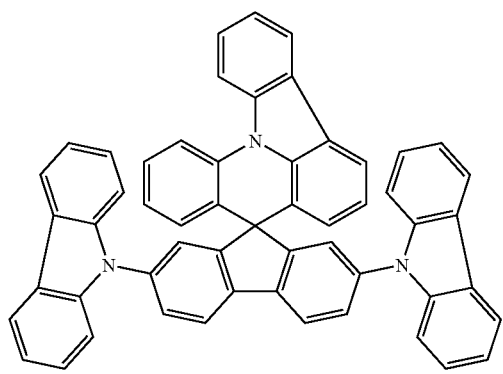
[Formula 11]
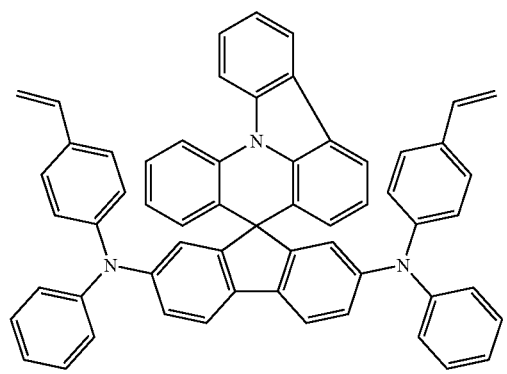

-continued
[Formula 12]
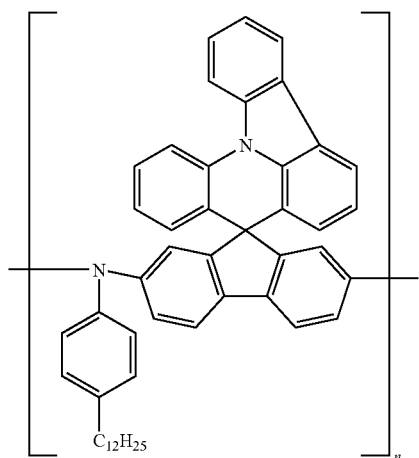
[Formula 13]
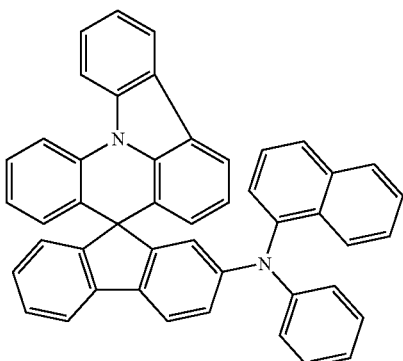
[Formula 14]
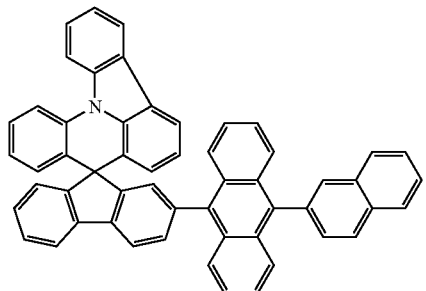
[Formula 15]
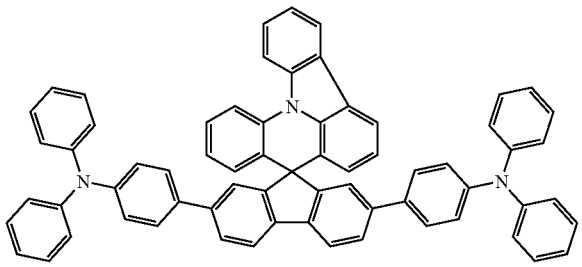
[Formula 16]
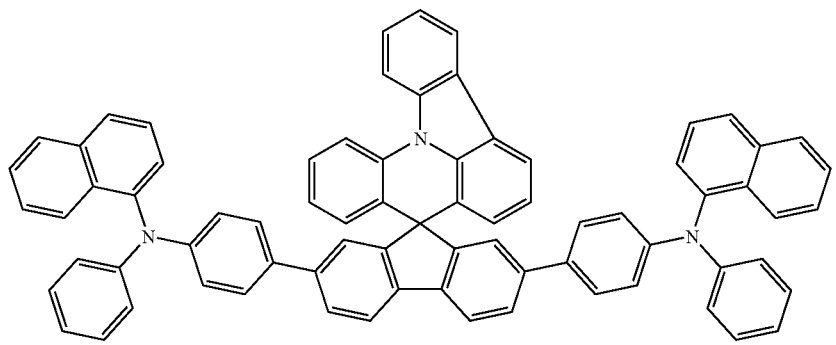
[Formula 17]
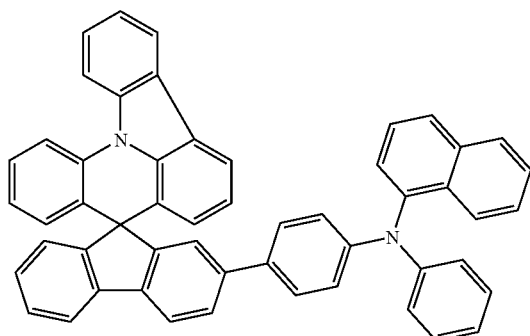

[Formula 18]
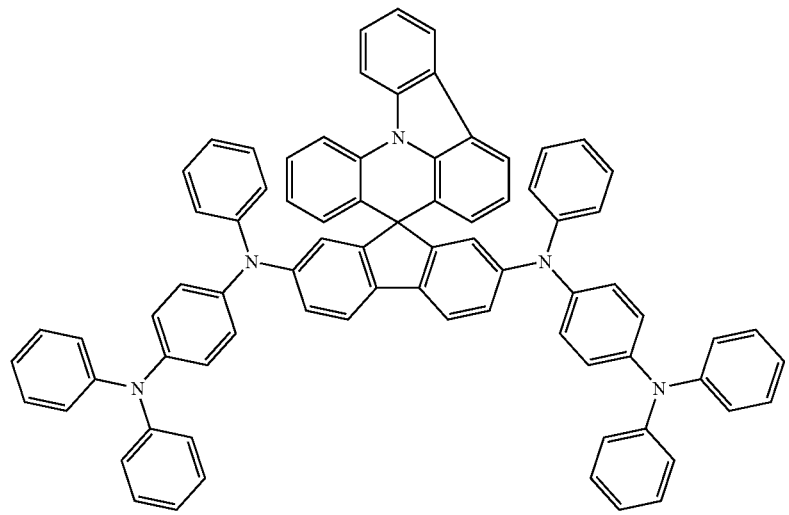
[Formula 9]
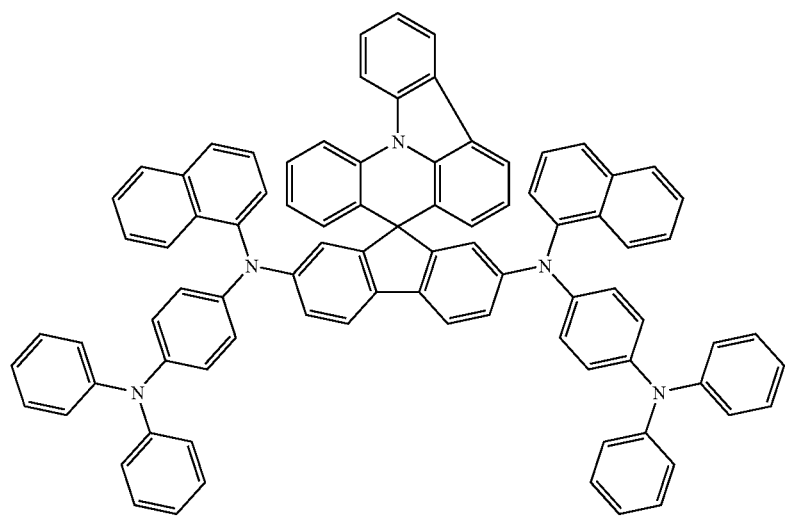
[Formula 20]
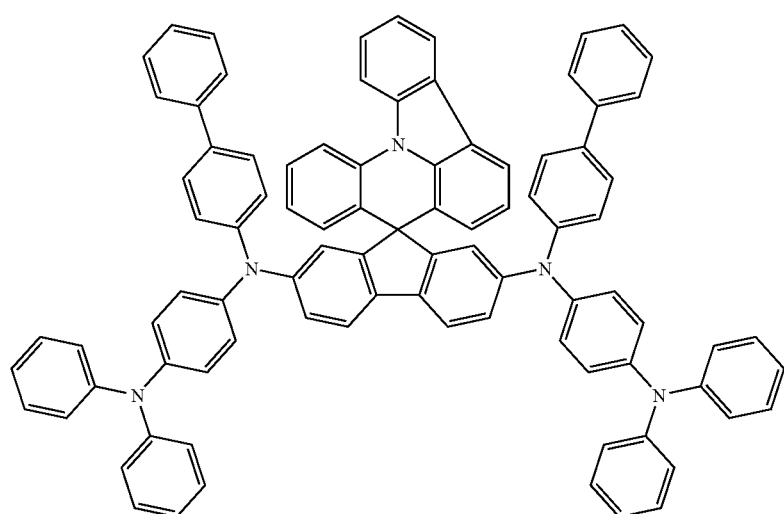

[Formula 21]
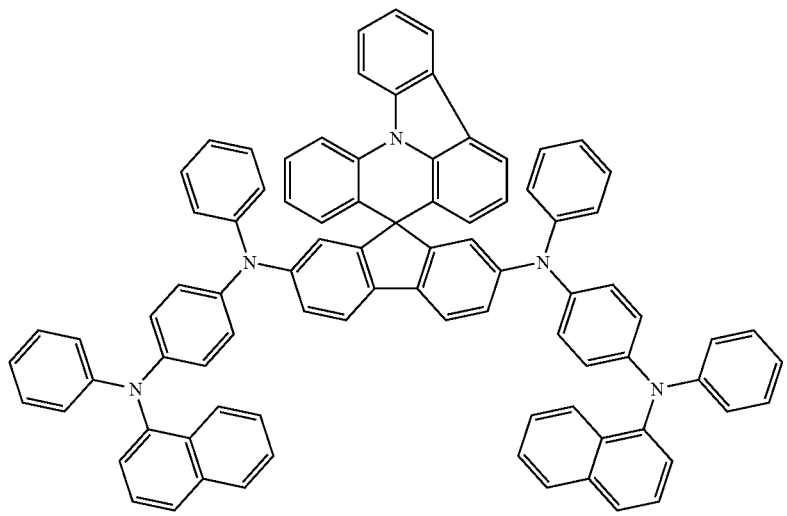
[Formula 22]
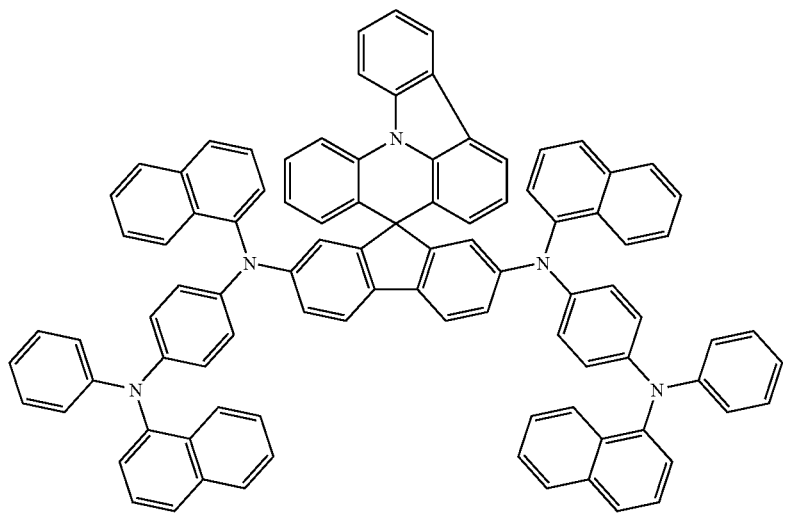
[Formula 23]
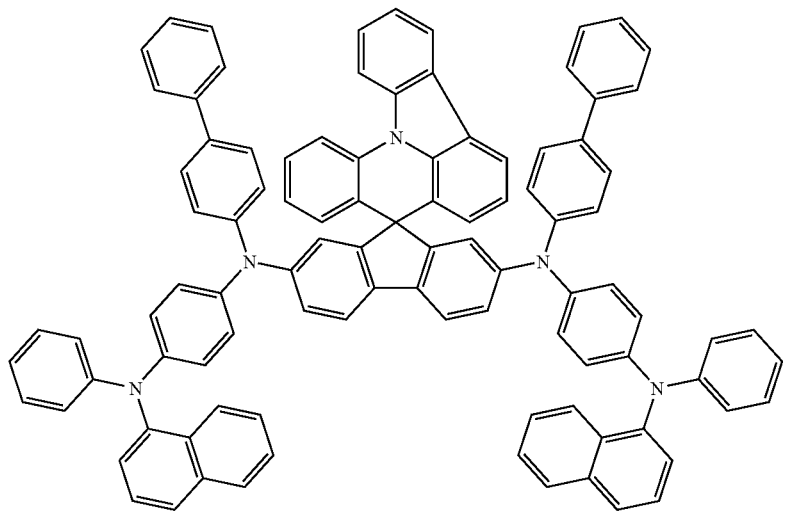

[Formula 24]
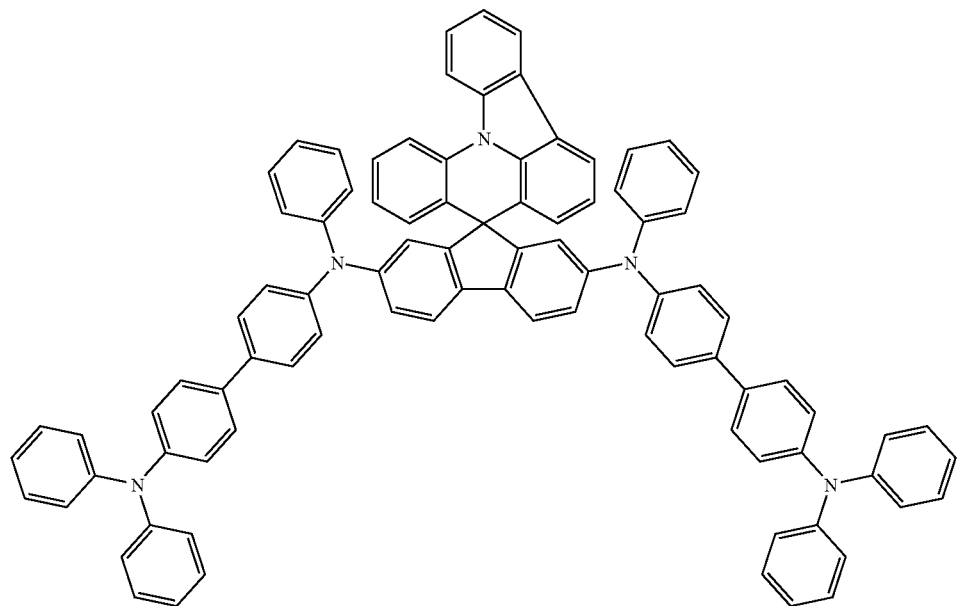
[Formula 25]
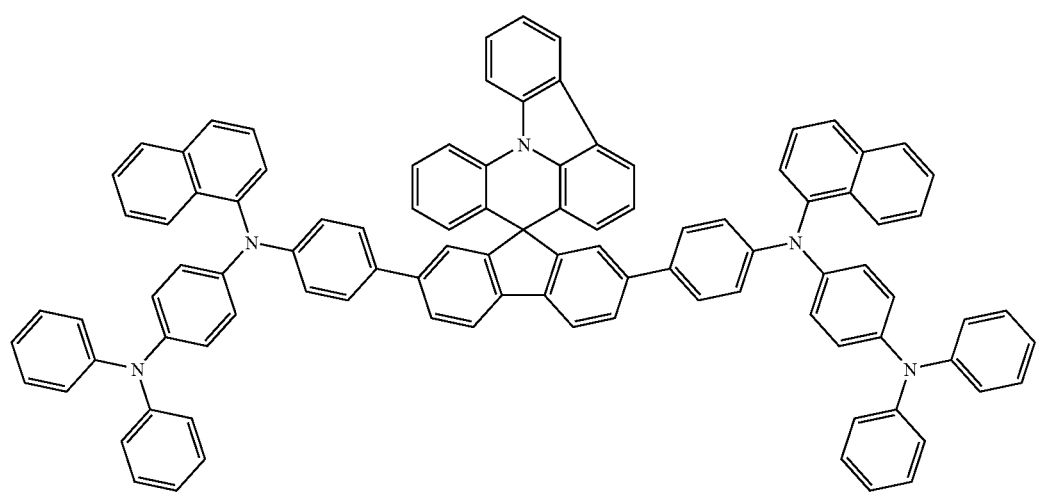

[Formula 26]
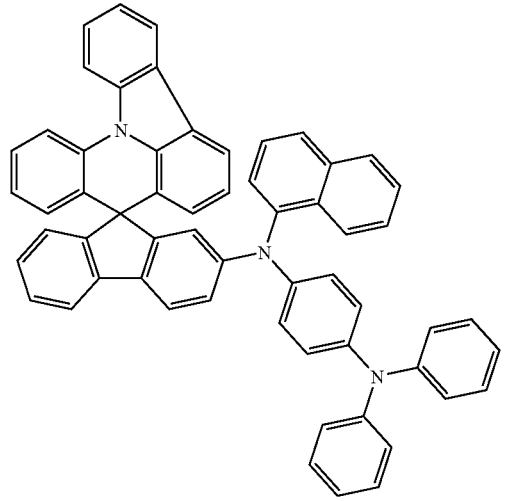
[Formula 27]
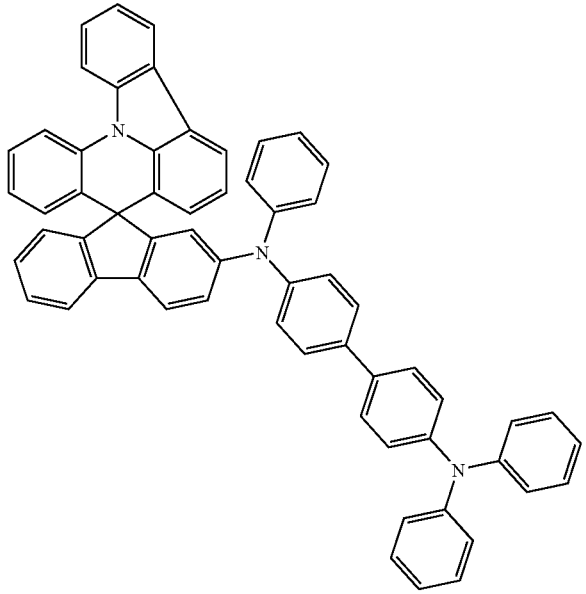
[Formula 28]
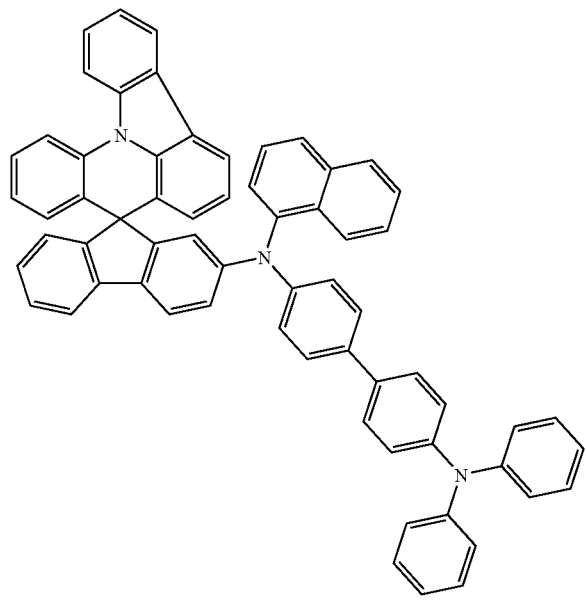
[Formula 29]
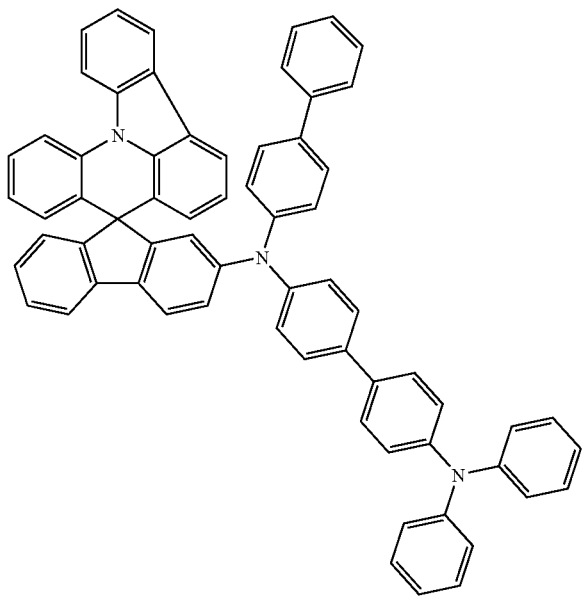

[Formula 30]
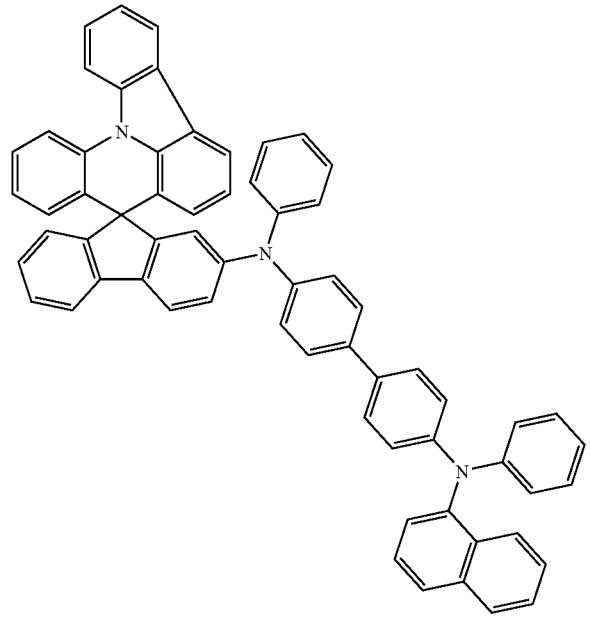
[Formula 31]
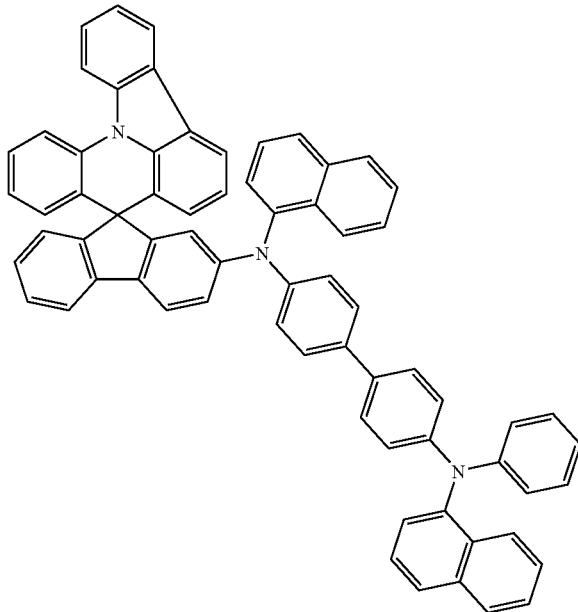
[Formula 32]
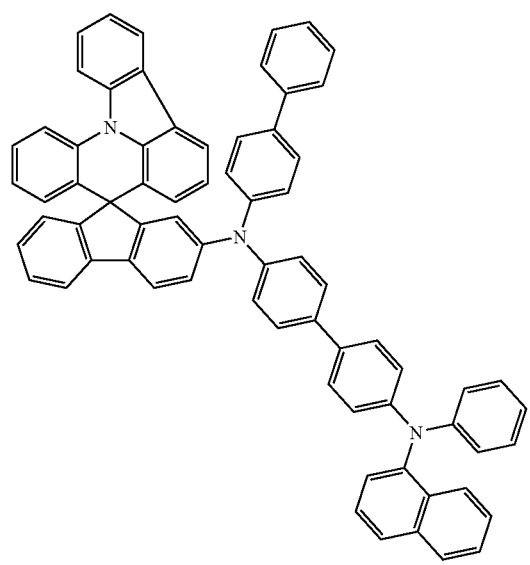
[Formula 33]
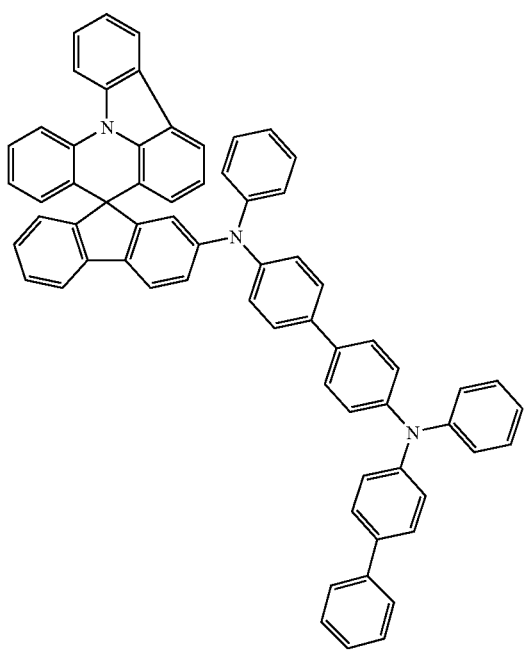

[Formula 34]
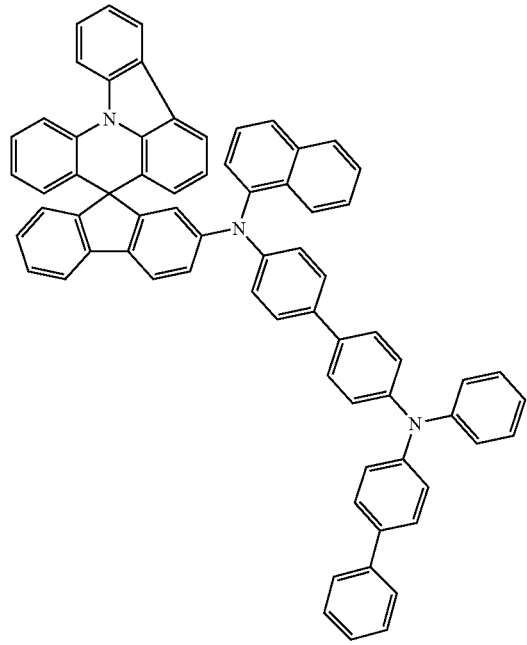
[Formula 35]
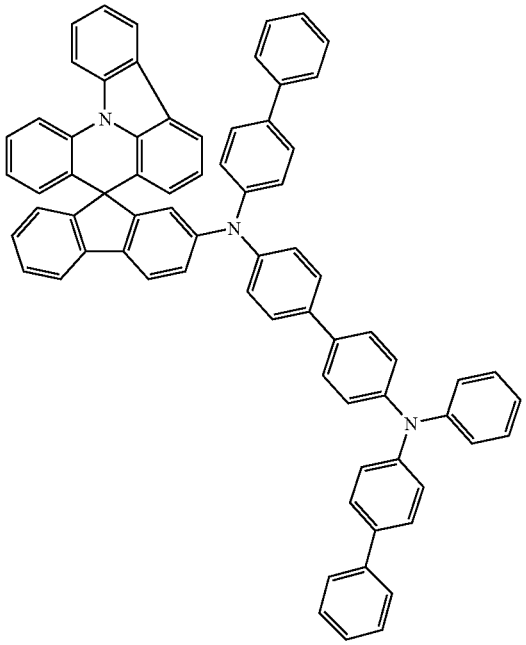
[Formula 36]
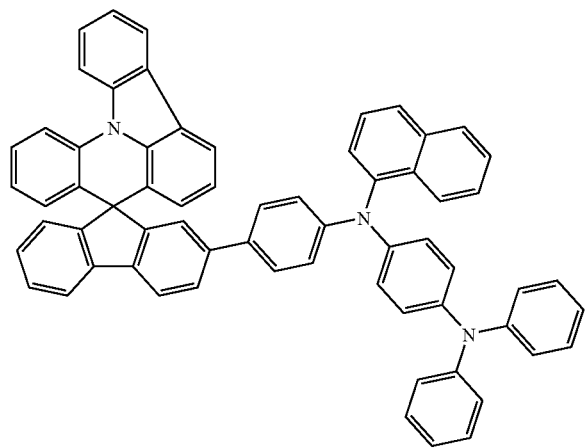
[Formula 37]
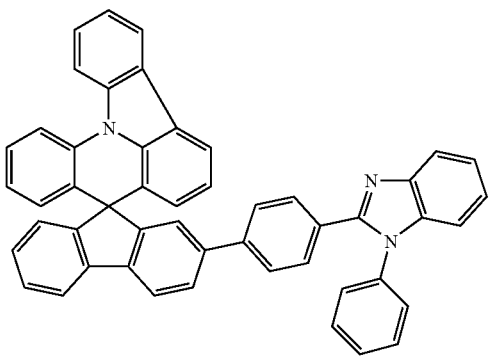

BRIEF DESCRIPTION OF THE DRAWINGS

FIG. 1 illustrates an organic light emitting device comprising a substrate 1, an anode 2, a light emitting layer 3, and a cathode 4; and FIG. 2 illustrates an organic light emitting device comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of an organic light emitting device according to the present invention.

Various substituent groups are introduced into a core structure shown in Formula 1, in detail, the core structure in which a fluorene group is bonded to a combination of an acridine group and a carbazolyl group to form a spiro structure, thereby the compound of Formula 1 has characteristics suitable for application to an organic material layer used in an organic light emitting device. This will be described in detail, below.

The steric core structure of the compound of Formula 1, for convenience of explanation, can be divided into two portions, A and B, as shown in the following Formula.

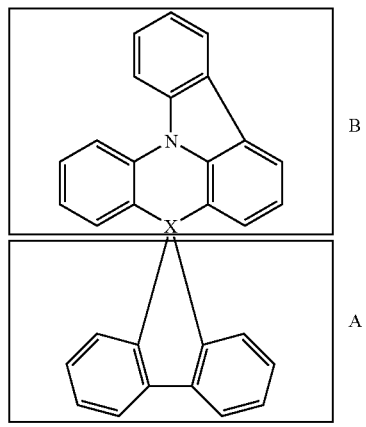

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to $R_1$ to $R_{19}$ positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into the $R_1$ to $R_{19}$ of the core structure.

Additionally, by introducing various substituent groups into the core structure, compounds having intrinsic characteristics of the substituent groups can be synthesized. For example, substituent groups, which are frequently applied to hole injection layer materials, hole transport layer materials, light emitting layer materials, and electron transport layer materials which are used during the production of the organic light emitting device, are introduced into the core structure so as to produce substances capable of satisfying requirements of each organic material layer. For example, since the core structure of the compound of Formula 1 includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are symmetrically or asymmetrically introduced into the core structure so as to precisely control the energy band gap, and interfacial characteristics with the organic materials is improved and thereby make it possible to apply the compound to various fields.

Additionally, the steric structure of the compound of Formula 1 suppresses the formation of excimers due to spiro bonding, and various substituent groups are introduced into the steric structure to control the three-dimensional structure of the organic material so as to minimize π-π interaction in the organic material, thereby formation of excimers is prevented.

With respect to the energy band gap and the energy level, for example, since the compound of Formula 2, in which arylamine is introduced into the hole transport material or the hole injection material of the structure of Formula 1, has HOMO of 5.37 eV, it has an energy level suitable for the hole injection layer or the hole transport layer. Meanwhile, the compound of Formula 2 has the band gap of 3.09 eV, which is still larger than that of NPB, typically used as the hole transport layer material, thus it has a LUMO value of about 2.28 eV, which is considered to be very high. If a compound having a high LUMO value is used as the hole transport layer, it increases the energy wall of LUMO of the material constituting the light emitting layer to prevent the movement of electrons from the light emitting layer to the hole transport layer. Accordingly, the above-mentioned compound improves the light emission efficiency of the organic light emitting device so that efficiency is higher than that of conventionally used NPB (HOMO 5.4 eV, LUMO 2.3 eV, and energy band gap 3.1 eV). In the present invention, the energy band gap is calculated by a typical method using a UV-VIS spectrum.

As well, the compound of Formula 1 has stable redox characteristics. Redox stability is estimated using a CV (cyclovoltammetry) method. For example, if oxidation voltage is repeatedly applied to the compound of Formula 2, oxidation repeatedly occurs at the same voltage and the current amount is constant. This means that the compound has excellent stability to oxidation.

Meanwhile, since the compound of Formula 1 has a high glass transition temperature (Tg), it has excellent thermal stability. For example, the glass transition temperature of the compound of Formula 2 is 131° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 2 has excellent solubility to a polar solvent, such as xylene, dichloroethane, or NMP, which is used during the production of the device, and forms a thin film very well through the process using a solution, thus the solution coating process may be applied to produce the device. Additionally, a light emitting wavelength of a thin film or a solid formed using the solution coating process is typically shifted to a longer wavelength due to interaction between molecules, in comparison with a light emitting wavelength in a solution state. Little shift in the wavelength occurs in the compound having the structure shown in Formula 1.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

In the organic light emitting device of the present invention, a compound, in which a thermosetting or photo-crosslinkable functional group is introduced into the compound of Formula 1, for example the compound of Formula 12, may be used instead of the compound of Formula 1. The former compound has the basic physical properties of the compound of Formula 1, and may be used to form a thin film using a solution coating process and then be cured so as to form an organic material layer during the production of the device.

The method of forming the organic material layer, which comprises introducing the curable functional group into the organic material during the production of the organic light emitting device, forming the organic thin film using the solution coating process, and curing the resulting film, is disclosed in U.S. Pat. No. 2003-0044518 and EP Pat. No. 1146574A2.

The above documents state that, if the organic material layer is formed through the above-mentioned method using a material having a thermosetting or photo-crosslinkable vinyl or acryl group so as to produce an organic light emitting device, it is possible to produce an organic light emitting device having a low voltage and high brightness as well as an organic light emitting device having a multilayered structure using the solution coating process. This operation mechanism may be applied to the compound of the present invention.

In the present invention, the thermosetting or photo-crosslinkable functional group may be a vinyl or acryl group.

The organic light emitting device of the present invention can be produced using known materials through a known process, modified only in that at least one layers of organic material layer(s) include the compound of the present invention, that is, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, and an electron injection layer as the organic material layers. However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

MODE FOR THE INVENTION

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, any one of the compounds of the following Formulae, a to e, may be used as a starting material.

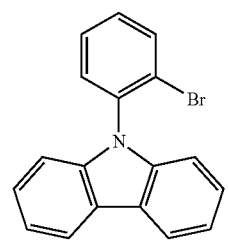

[Formula a]

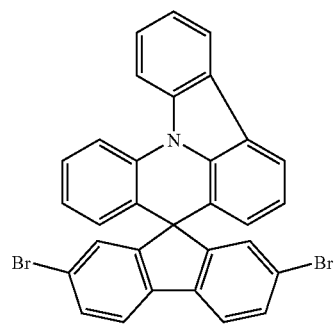

[Formula b]

-continued

[Formula c]

[Formula d]

[Formula e]

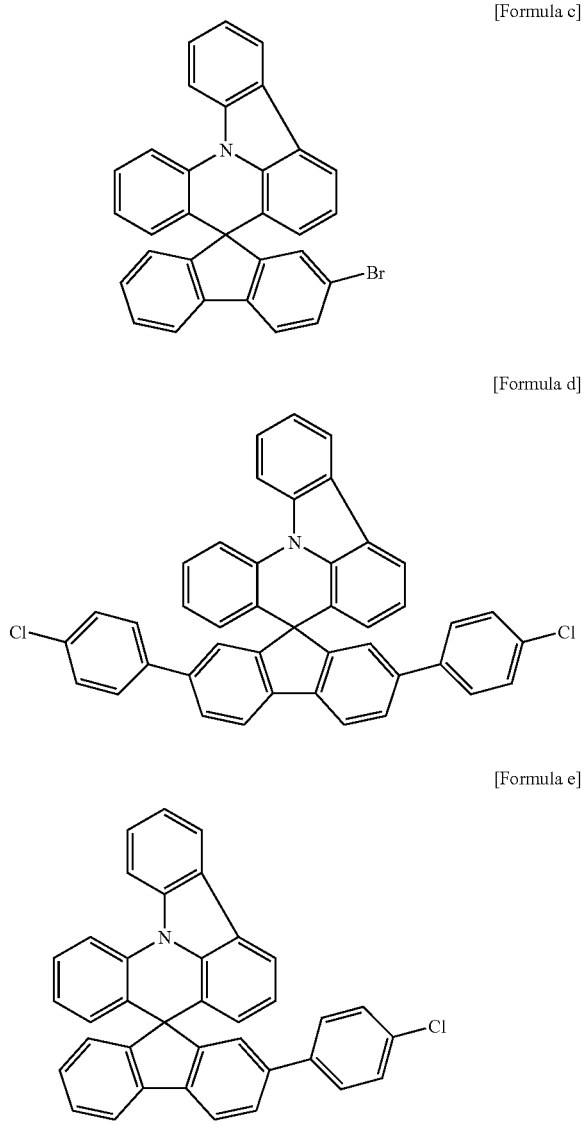

Preparation Example 1

Preparation of a Starting Material Represented by Formula a

Carbazole (1.672 g, 10 mmol), 1-bromo-2-iodobenzene (1.5 ml, 12 mmol), potassium carbonate ($K_2CO_3$, 2.7646 g, 20 mmol), copper iodide (CuI, 95 mg, 0.5 mmol), and 25 ml of xylene were refluxed in a nitrogen atmosphere. After cooling to normal temperature was conducted, a product was extracted with ethyl acetate, water was removed with anhydrous magnesium sulfate ($MgSO_4$), and the solvent was removed at a reduced pressure. The resulting product was passed through a silica gel column using a hexane solvent to produce a compound, the solvent was removed at a reduced pressure, and vacuum drying was conducted to produce the resulting white solid compound (800 mg, 25% yield). MS: $[M+H]^+=323$.

Preparation Example 2

Preparation of a Starting Material Represented by Formula b

The starting material represented by Formula a (6.96 g, 21.6 mmol) was dissolved in 300 ml of purified THF and cooled to −78° C., and n-BuLi (2.5 M in hexane, 8.64 ml, 21.6 mmol) was slowly dropped thereon. Stirring was conducted at the same temperature for 30 min, and 2,7-dibromo-9-fluorenone (6.08 g, 18.0 mmol) was added thereto. After Stirring was conducted at the same temperature for 40 min, the temperature was raised to normal temperature and stirring was carried out for an additional 3 hours. The reaction was completed in an ammonium chloride ($NH_4Cl$) aqueous solution, and extraction was conducted with ethyl ether. Water was removed from an organic material layer using anhydrous magnesium sulfate ($MgSO_4$), and an organic solvent was then removed therefrom. The produced solid was dispersed in ethanol, stirred for one day, filtered, and vacuum dried to produce 10.12 g of intermediate material (96.7% yield). The intermediate solid was dispersed in 10 ml of acetic acid, ten drops of concentrated sulfuric acid were added thereto, and reflux was conducted for 4 hours. The resulting solid was filtered, washed with ethanol, and vacuum dried to produce 9.49 g of compound of Formula b (96.8% yield). MS: $[M+H]+=563$.

Preparation Example 3

Preparation of a Starting Material Represented by Formula c 4.19 g of starting material represented by Formula a (13 mmol) were dissolved in 50 ml of purified THF, and 4.8 ml of n-BuLi (2.5 M in hexane, 12 mmol) were slowly dropped thereon at −78° C. Stirring was conducted at the same temperature for 45 min, and 2.59 g of 2-bromo-9-fluorenone (10.0 mmol) were added thereto. After stirring was conducted at the same temperature for 1 hour, the temperature was raised to normal temperature, stirring was carried out for an additional 2 hours, and the reaction was completed in a $NH_4Cl$ aqueous solution. An organic material was extracted with ethyl ether, water was removed therefrom, and an organic solvent was removed to produce yellow solid. The produced solid was dispersed in ethanol, stirred, filtered, and vacuum dried to produce 4.5 g of intermediate material. The intermediate solid was dispersed in 40 ml of acetic acid, 12 drops of concentrated sulfuric acid were added thereto, and reflux was conducted for 3 hours. After cooling to normal temperature, the resulting solid was filtered, washed with ethanol, and vacuum dried to create 3.98 g of product (82.2% yield). MS: $[M+H]^+=484$.

Preparation Example 4

Preparation of a Starting Material Represented by Formula d

The starting material represented by Formula b (10.0 g, 17.8 mmol) was completely dissolved in 200 ml of THF, 4-chloro-phenylboronic acid (8.30 g, 53.3 mmol), 2M potassium carbonate solution, tetrakis(triphenylphosphine)palladium(0) (0.62 g, 0.53 mmol), and 10 ml of ethanol were added thereto, and reflux was conducted for 24 hours. After the reaction was completed, cooling to normal temperature was conducted, and filtration was conducted. Washing was conducted with water and ethanol several times. Recrystallization was conducted with ethanol, and vacuum drying was conducted to produce a compound (9.5 g, 85% yield). MS: [M+H]$^+$=625.

Preparation Example 5

Preparation of a Starting Material Represented by Formula e

The starting material represented by Formula c (5.0 g, 10.32 mmol) was completely dissolved in 40 ml of THF, 4-chloro-phenylboronic acid (2.42 g, 15.48 mmol), 2M potassium carbonate solution, tetrakis(triphenylphosphine)palladium(0) (0.31 mmol, 0.36 g), and 10 ml of ethanol were added thereto, and reflux was conducted for 24 hours. After the reaction was completed, cooling to normal temperature was conducted, and filtration was conducted. Washing was conducted with water and ethanol several times. Recrystallization was conducted with ethanol, and vacuum drying was conducted to produce a compound (4.97 g, yield 93%). MS: [M+H]$^+$=515.

Example 1

Preparation of the Compound Represented by Formula 2

After the compound of Formula b (3.0 g, 5.3 mmol) was dispersed in 50 ml of xylene, diphenylamine (2.07 g, 12.2 mmol), sodium tert-butoxide (0.074 g, 0.370 mmol), tris(dibenzylideneacetone)dipalladium(0) (Pd (dba), 0.14 g, 0.25 mmol), and tri-t-butylphosphine (3.50 g, 36.7 mmol) were sequentially added thereto, and reflux was conducted at 120° C., for 2 hours. After cooling to normal temperature, water was added thereto, a layer separation process was conducted, and water and the solvent were removed from an organic layer. The resulting substance was dispersed in ethyl acetate, and stirred for one day. The solid was filtered and vacuum dried. The resulting solid was subjected to a column separation process using n-hexane/tetrahydrofuran (n-hexane/THF=4/1), and the product was dispersed in ethanol, boiled therein, stirred, and filtered to produce 1.7 g of compound of Formula 2 (43% yield). MS: [M+H]$^+$=740.

Example 2

Preparation of the Compound Represented by Formula 3

After the compound of Formula b (1.13 g, 2.00 mmol) was dispersed in 20 ml of xylene, N-phenyl-1-naphthylamine (0.965 g, 4.40 mmol), sodium tert-butoxide (0.433 g, 4.50 mmol), tris(dibenzylideneacetone)dipalladium(0) (Pd$_2$(dba)$_3$, 0.073 g, 0.080 mmol), and 50 wt % tri-t-butylphosphine (0.024 g, 0.120 mmol) were sequentially added thereto, and reflux was conducted at 120° C. for 1.5 hours. After cooling to normal temperature was conducted, water was added thereto, a layer separation process was conducted, and water and the solvent were removed from an organic layer. The resulting substance was dispersed in ethyl acetate, and stirred for one day. The solid was filtered and vacuum dried. The resulting solid was subjected to a column separation process using n-hexane/tetrahydrofuran (n-hexane/THF=4/1), and the product was dispersed in ethanol, boiled therein, stirred, and filtered to produce 0.680 g of compound of Formula 3 (40.5% yield). MS: [M+H]$^+$=841.

Example 3

Preparation of the Compound Represented by Formula 4

The compound of Formula b (2.5 g, 4.4 mmol) and N-phenyl-2-naphthylamine (2.2 g, 10 mmol) were dissolved in 50 ml of toluene, sodium-tert-butoxide (1.26 g, 13.2 mmol), tris(dibenzylidene acetone)dipalladium(0) (Pd$_2$(dba)$_3$, 0.08 g, 0.08 mmol), and 50 wt % tri-tert-butylphosphine (0.02 g, 0.13 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 4 (1.92 g, yield 52%). MS: [M+H]$^+$=839.

Example 4

Preparation of the Compound Represented by Formula 5

1) Synthesis of arylamine (N-phenyl-4-biphenylamine) to produce the compound represented by Formula 5: aniline (10 ml, 109.74 mmol) and 4-bromobiphenylamine (25.6 g, 109.7 mmol) were dissolved in 300 ml of toluene, and bis(dibenzylidene acetone)palladium(0) (Pd(dba), 1.26 g, 2.20 mmol), 50 wt % tri-tert-butylphosphine toluene solution (1.30 ml, 3.29 mmol), and sodium-tert-butoxide (21.09 g, 219.5 mmol) were added thereto. Reflux was conducted in a nitrogen atmosphere for 2 hours, and distilled water was added to the reaction solution to complete the reaction. The organic layer was extracted, and a column separation process was conducted using a developing solvent of n-hexane and tetrahydrofuran (n-hexane/THF=10/1), stirring was conducted using petroleum ether, and vacuum drying was conducted to produce arylamine (15 g, yield 56%). MS: [M+H]$^+$=246.

2) The compound of Formula b (2.5 g, 4.44 mmol) and N-phenyl-4-biphenylamine (2.72 g, 11.1 mmol) were dissolved in 30 ml of toluene, and bis(dibenzylidene acetone)palladium(0) (Pd(dba), 0.051 g, 0.09 mmol), 50 wt % tri-tert-butylphosphine toluene solution (0.05 ml, 0.13 mmol), and sodium-tert-butoxide (1.707 g, 17.76 mmol) were added thereto. After reflux was conducted in a nitrogen atmosphere for 2 hours, distilled water was added to the reaction solution to complete the reaction. The organic layer was extracted, and a column separation process was conducted using a developing solvent of n-hexane and tetrahydrofuran (n-hexane/THF=10/1), stirring was conducted using petroleum ether, and vacuum drying was conducted to produce the compound of Formula 5 (3.2 g, yield 80.8%). MS: [M+H]$^+$=893.

Example 5

Preparation of the Compound Represented by Formula 6

1) Synthesis of arylamine (1,1-dinaphthylamine) to produce the compound represented by Formula 6: 1-aminonaphthalene (10.0 g, 69.84 mmol) and 1-bromonaphthalene (7.47 ml, 53.7 mmol) were dissolved in 200 ml of toluene, and tris(dibenzylidene acetone)dipalladium(0) (Pd$_2$(dba)$_3$, 1.21 g, 2.10 mmol), 50 wt % tri-tert-butylphosphine (1.38 ml, 2.79 mmol), and sodium-tert-butoxide (16.78 g, 174.6 mmol)

were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce arylamine (5.26 g, yield 28%). MS: [M+H]$^+$=270.

2) The compound of Formula b (5.0 g, 8.88 mmol) and 1,1-dinaphthylamine (5.26 g, 19.5 mmol) were dissolved in 50 ml of toluene, and bis(dibenzylidene acetone)palladium(0) (Pd(dba), 0.204 g, 0.36 mmol), 50 wt % tri-tert-butylphosphine toluene solution (0.31 ml, 0.62 mmol), and sodium-tert-butoxide (4.694 g, 48.84 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=9/1), stirring was conducted using petroleum ether, and vacuum drying was conducted to produce the compound of Formula 6 (3.29 g, yield 39.4%). MS: [M+H]$^+$=941.

Example 6

Preparation of the Compound Represented by Formula 7

1) Synthesis of arylamine (1,4-naphthylbiphenylamine) to produce the compound represented by Formula 7: 1-aminonaphthalene (7.4 g, 51.48 mmol) and 4-bromobiphenyl (12 g, 51.48 mmol) were dissolved in 200 ml of toluene, and bis(dibenzylidene acetone)palladium(0) (Pd(dba)$_2$, 0.89 g, 1.54 mmol), 50 wt % tri-tert-butylphosphine (0.60 ml, 1.54 mmol), and sodium-tert-butoxide (9.90 g, 103.0 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce arylamine (6.3 g, yield 42%). MS: [M+H]$^+$=295.

2) The compound of Formula b (3 g, 5.33 mmol) and 1,4-naphthylbiphenylamine (3.62 g, 12.25 mmol) were dissolved in 80 ml of toluene, and bis(dibenzylidene acetone)palladium(0) (Pd(dba)$_2$, 0.06 g, 0.11 mmol), 50 wt % tri-tert-butylphosphine toluene solution (0.06 ml, 0.16 mmol), and sodium-tert-butoxide (1.54 g, 16.0 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=9/1), stirring was conducted using petroleum ether, and vacuum drying was conducted to produce the compound of Formula 7 (3.2 g, yield 61%). MS: [M+H]$^+$=992.

Example 7

Preparation of the Compound Represented by Formula 8

1) Synthesis of arylamine (4,4-dibiphenylamine) to produce the compound represented by Formula 8: 4-aminobiphenyl (30.5 g, 180.17 mmol) and 4-bromobiphenyl (40 g, 171.59 mmol) were dissolved in 500 ml of toluene, and bis(dibenzylidene acetone)palladium(0) (Pd(dba)$_2$, 2.07 g, 3.60 mmol), 50 wt % tri-tert-butylphosphine (2.2 ml, 5.41 mmol), and sodium-tert-butoxide (51.94 g, 540.5 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce 4,4-dibiphenylamine (32 g, yield 58%). MS: [M+H]$^+$=321.

2) The compound of Formula b (5.4 g, 0.62 mmol) and 4,4-dibiphenylamine (6.80 g, 2.12 mmol) were dissolved in 200 ml of toluene, and bis(dibenzylidene acetone)palladium(0) (Pd(dba)$_2$, 0.243 g, 0.423 mmol), 50 wt % tri-tert-butylphosphine toluene solution (0.260 ml, 0.635 mmol), and sodium-tert-butoxide (6.10 g, 63.5 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=9/1), stirring was conducted using petroleum ether, and vacuum drying was conducted to produce the compound of Formula 8 (6.3 g, yield 63%). MS: [M+H]$^+$=1044.

Example 8

Preparation of the Compound Represented by Formula 9

The compound of Formula b (2.5 g, 4.4 mmol) and 4-methyldiphenylamine (2.0 g, 10 mmol) were dissolved in 50 ml of xylene, sodium-tert-butoxide (1.26 g, 13.2 mmol), tris(dibenzylidene acetone)dipalladium(0) (Pd$_2$(dba)$_3$, 0.08 g, 0.08 mmol), and 50 wt % tri-tert-butylphosphine (0.02 g, 0.13 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 9 (1.8 g, yield 52%). MS: [M+H]$^+$=768.

Example 9

Preparation of the Compound Represented by Formula 10

The compound of Formula b (845 mg, 1.5 mmol), carbazole (602 mg, 2.4 eq), bis(dibenzylidene acetone)palladium(0) (Pd(dba)$_2$, 27 mg, 0.02 eq), tri-tert-butylphosphine (9 mg, 0.03 eq), sodium-tert-butoxide (432 mg, 3 eq), and 15 ml of xylene were refluxed for one day. After cooling, extraction was conducted using water and ethyl acetate, water was removed with MgSO$_4$, and a column separation process was conducted using n-hexane and tetrahydrofuran (n-hexane/THF=4/1). The resulting substance was solidified with ethanol, filtered, and vacuum dried to produce the compound of Formula 10 (995 mg, yield 90%). MS: [M+H]$^+$=736.

Example 10

Preparation of the compound represented by Formula 11

1) The compound of Formula b (2.25 g, 4 mmol) and aniline (0.8 ml, 8.8 mmol) were dissolved in 40 ml of xylene, and tri-tert-butylphosphine (0.05 g, 0.24 mmol) and tris(dibenzylidene acetone)dipalladium(0) (Pd$_2$(dba)$_2$, 0.15 g, 0.16 mmol) were sequentially added thereto. After reflux was conducted for 6 hours, cooling to normal temperature was conducted, and water was added thereto. The organic layer was separated, and a column separation process was conducted using n-hexane and tetrahydrofuran (n-hexane/THF=4/1) to produce 1.23 g of a light brown solid. MS: [M+H]$^+$=588.

2) 0.59 g of the above compound (1 mol); 4-bromostyrene (0.28 ml, 2.1 mmol), sodium-tert-butoxide (0.21 g, 2.2 mmol), tri-tert-butylphosphine (0.012 g, 0.06 mmol), and tris(dibenzylidene acetone)dipalladium(0) (Pd$_2$(dba)$_3$, 0.037 g, 0.04 mmol) were added to xylene, and reflux was conducted for 3 hours. After cooling to normal temperature, water was added thereto, the organic layer was extracted, and a column separation process was conducted using n-hexane and tetrahydrofuran (n-hexane/THF=4/1) to produce the compound of Formula 11 (0.2 g). MS: [M+H]$^+$=792.

Example 11

Preparation of the Compound Represented by Formula 12

The compound of Formula b (1.12 g, 2.0 mmol) and 4-dodecylaniline (0.53 g, 2.0 mmol) were dissolved in distilled toluene (30 ml), sodium-tert-butoxide (0.58 g, 6.0 mmol), tris(dibenzylidene acetone)dipalladium(0) (Pd$_2$(dba)$_3$, 0.046 g, 0.05 mmol), and tri-tert-butylphosphine (0.06 g, 0.3 mmol) were added thereto, and stirring was conducted in a nitrogen atmosphere at 100° C. After 36 hours, ammonia water was added to the reaction solution to complete the reaction, and the organic layer was extracted. The extracted organic layer was concentrated in tetrahydrofuran (THF) and reprecipitated in ethanol. The resulting yellow solid was filtered to separate it, and additional reprecipitation was repeated twice. The filtered yellow solid was dissolved in tetrahydrofuran (THF), and then adsorbed onto a silica gel to achieve column separation. n-hexane and tetrahydrofuran (n-hexane/THF=4/1) were used as a developing solvent to remove developed impurities, and a product mixture was developed with tetrahydrofuran (THF) and thus separated. The separated product mixture was poured on a celite layer (Celite 545) to be filtered, and the filtered solution was concentrated with tetrahydrofuran (THF). The concentrated product was reprecipitated in ethanol, filtered, and vacuum dried to produce a yellow polymer mixture of Formula 12 (0.89 g, yield 54%).

MALDI-MS: [M+H]$^+$=3318, 3980, 4644, 5309, 5971, 6634, 7302.

GPC (polystyrene standard)

Mn Mw Mp Mz PDI 10222 19.685 22343 31802 1.9

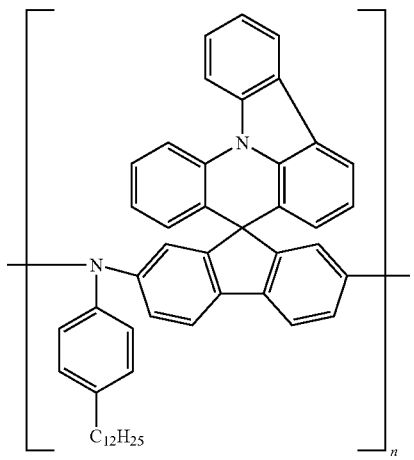

Example 12

Preparation of the Compound Represented by Formula 13

The compound of Formula c (3.0 g, 6.19 mmol) and N-phenyl-1-naphthylamine (1.5 g, 6.81 mmol) were dissolved in 50 ml of toluene, sodium-tert-butoxide (0.89 g, 9.3 mmol), bis(dibenzylidene acetone)palladium(0) (Pd(dba)$_2$, 0.07 g, 0.124 mmol), and 50 wt % ti-tert-butylphosphine (0.09 ml, 0.186 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 13 (2.0 g, yield 52%). MS: [M+H]$^+$=622.

Example 13

Preparation of the Compound Represented by Formula 14

2.42 g of compound of Formula c (5 mmol) were dissolved in 30 ml of purified THF, and 2.2 ml of n-BuLi (2.5 M in hexane, 5.5 mmol) were slowly dropped thereon. Stirring was conducted at the same temperature for 1 hour, and 0.68 ml of trimethyl borate (6 mmol) were added thereto. After stirring was conducted at the same temperature for 1 hour, the temperature was raised to normal temperature, stirring was carried out for an additional 2 hours, the reaction was completed in 2N HCl, and extraction was conducted with ethyl ether. After the solvent was removed, petroleum ether was added to the solid, and stirring was conducted for one day. The resulting solid was filtered and vacuum dried to create 1.75 g of product (77.9% yield).

After 25 ml of purified DMF were bubbled using N$_2$ gas for one day to desirably remove oxygen, 0.96 g of 9-bromo-10-(2-naphthyl)anthracene (2.5 mmol), 1.685 g of boronic acid compound (3.75 mmol), 0.85 g of K$_3$PO$_4$ (4.0 mmol), and 0.29 g of Pd(PPh$_3$)$_4$ (0.25 mmol) were added thereto, and stirring was conducted at 80° C. for one day. After cooling to normal temperature was conducted, filtration was conducted, and the solid washed with DMF. The filtrate was collected, the solvent was removed, acetone was added to the solid, and stirring was conducted. The resulting solid was filtered, dried, and subjected to a column separation process using n-hexane and tetrahydrofuran (n-hexane/THF=4/1) to produce 1.5 g of the compound of Formula 14 (84.8% yield). MS: [M+H]= 708.

Example 14

Preparation of the Compound Represented by Formula 15

The compound of Formula d (5.08 g, 8.11 mmol) and diphenylamine (3.02 g, 17.8 mmol) were dissolved in 100 ml of toluene, sodium-tert-butoxide (5.15 g, 53.6 mmol), bis (dibenzylidene acetone)palladium(0) (Pd(dba)$_2$, 0.21 g, 0.36 mmol), and tri-tert-butylphosphine (0.11 ml, 0.54 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 15 (4.30 g, yield 54.6%). MS: [M+H]$^+$= 891.

Example 15

Preparation of the Compound Represented by Formula 16

The compound of Formula d (5.0 g, 10.32 mmol) and N-phenyl-1-naphthylamine (3.85 g, 17.56 mmol) were dissolved in 50 ml of toluene, sodium-tert-butoxide (2.3 g, 23.94 mmol), bis(dibenzylidene acetone)palladium(0) (Pd(dba)$_2$, 0.09 g, 0.16 mmol), and tri-tert-butylphosphine (0.12 ml, 0.24 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 16 (4.8 g, yield 61%). MS: [M+H]$^+$= 991.

Example 16

Preparation of the Compound Represented by Formula 17

The compound of Formula e (5.0 g, 9.69 mmol) and N-phenyl-1-naphthylamine (2.3 g, 10.5 mmol) were dissolved in 50 ml of toluene, sodium-tert-butoxide (3.02 g, 31.5 mmol), bis(dibenzylidene acetone)palladium(0) (Pd(dba), 0.217 g, 0.121 mmol), and 50 wt % tri-tert-butylphosphine (0.13 ml, 0.315 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce a compound (4.2 g, yield 62%). MS: [M+H]$^+$=698.

Example 17

Preparation of the Compound Represented by Formula 18

1) Synthesis of arylamine (4-(N-phenyl-N-phenylamino) phenyl-1-phenylamine) to produce the compound represented by Formula 18: 13.5 g of 4-bromophenyl-N-phenyl-N-phenylamine (41.6 mmol) and 3.98 ml of aniline (43.7 mmol) were dissolved in 120 ml of toluene, 10.00 g of sodium-tert-butoxide (104.1 mmol), 0.48 g of bis(dibenzylidene acetone)palladium(0) (0.83 mmol), and 0.58 ml of 50 wt % tri-tert-butylphosphine toluene solution (1.25 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (9.6 g, yield 69%). MS: [M+H]$^+$=336.

2) 3.0 g of compound of Formula b (5.3 mmol) and 4.12 g of 4-(N-phenyl-N-phenylamino)phenyl-1-phenylamine (12.3 mmol) were dissolved in 80 ml of toluene, 1.54 g of sodium-tert-butoxide (16.0 mmol), 0.06 g of bis(dibenzylidene acetone)palladium(0) (0.11 mmol), and 0.06 ml of 50 wt % tri-tert-butylphosphine toluene solution (0.16 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 18 (2.7 g, yield 47%). MS: [M+H]$^+$=1074.

Example 18

Preparation of the Compound Represented by Formula 19

1) Synthesis of arylamine (4-(N-phenyl-N-phenylamino) phenyl-1-naphthylamine) to produce the compound represented by Formula 19: 15.0 g of 4-bromophenyl-N-phenyl-N-phenylamine (46.3 mmol) and 7.29 g of 1-naphthylamine (50.9 mmol) were dissolved in 200 ml of toluene, 13.34 g of sodium-tert-butoxide (138.8 mmol), 0.53 g of bis(dibenzylidene acetone)palladium(0) (0.93 mmol), and 0.56 ml of 50 wt % tri-tert-butylphosphine toluene solution (1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (13 g, yield 73%). MS: [M+H]$^+$=386.

2) 5.00 g of compound of Formula b (8.88 mmol) and 7.90 g of 4-(N-phenyl-N-phenylamino)phenyl-1-naphthylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 19 (5.2 g, yield 50%). MS: $[M+H]^+$=1174.

Example 19

Preparation of the Compound Represented by Formula 20

1) Synthesis of arylamine (4-(N-phenyl-N-phenylamino) phenyl-1-biphenylamine) to produce the compound represented by Formula 20: 17.4 g of 4-bromophenyl-N-phenyl-N-phenylamine (53.7 mmol) and 9.99 g of 4-aminobiphenyl (59.0 mmol) were dissolved in 250 ml of toluene, 17.02 g of sodium-tert-butoxide (177.1 mmol), 0.68 g of bis(dibenzylidene acetone)palladium(0) (1.2 mmol), and 0.72 ml of 50 wt % tri-tert-butylphosphine toluene solution (1.8 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (16 g, yield 73%). MS: $[M+H]^+$=412.

2) 4.7 g of compound of Formula b (8.3 mmol) and 7.9 g of 4-(N-phenyl-N-phenylamino)phenyl-1-biphenylamine (19.2 mmol) were dissolved in 150 ml of toluene, 5.53 g of sodium-tert-butoxide (57.5 mmol), 0.22 g of bis(dibenzylidene acetone)palladium(0) (0.38 mmol), and 0.23 ml of 50 wt % tri-tert-butylphosphine toluene solution (0.58 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 20 (4.9 g, yield 48%). MS: $[M+H]^+$=1225.

Example 20

Preparation of the Compound Represented by Formula 21

1) Synthesis of arylamine (4-(N-phenyl-N-naphthylamino)phenyl-1-phenylamine) to produce the compound represented by Formula 21: 7.00 g of 4-bromophenyl-N-phenyl-N-naphthylamine (18.7 mmol) and 2.56 ml of aniline (28.1 mmol) were dissolved in 100 ml of toluene, 5.40 g of sodium-tert-butoxide (56.1 mmol), 0.22 g of bis(dibenzylidene acetone)palladium(0) (0.37 mmol), and 0.28 ml of 50 wt % tri-tert-butylphosphine toluene solution (0.37 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (5.1 g, yield 70%). MS: $[M+H]^+$=386.

2) 2.5 g of compound of Formula b (4.4 mmol) and 3.86 g of 4-(N-phenyl-N-naphthylamino)phenyl-1-phenylamine (10.0 mmol) were dissolved in 50 ml of toluene, 1.26 g of sodium-tert-butoxide (13.2 mmol), 0.08 g of tris(dibenzylidene acetone)dipalladium(0) (0.08 mmol), and 0.04 ml of 50 wt % tri-tert-butylphosphine toluene solution (0.13 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 21 (2.5 g, yield 49%). MS: $[M+H]^+$=1173.

Example 21

Preparation of the Compound Represented by Formula 22

1) Synthesis of arylamine (4-(N-phenyl-N-naphthylamino)phenyl-1-naphthylamine) to produce the compound represented by Formula 22: 14.0 g of 4-bromophenyl-N-phenyl-N-naphthylamine (37.4 mmol) and 6.43 g of 1-naphthylamine (44.9 mmol) were dissolved in 200 ml of toluene, and 0.645 g of bis(dibenzylidene acetone)palladium(0) (1.12 mmol), 0.74 ml of 50 wt % tri-tert-butylphosphine toluene solution (1.5 mmol), and 8.99 g of sodium-tert-butoxide (93.5 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran at a ratio of 10:1, stirring was conducted using petroleum ether, and vacuum drying was conducted to produce an arylamine connection group (8.53 g, yield 52.2%). MS: $[M+H]^+$=437.

2) 5.00 g of compound of Formula b (8.88 mmol) and 8.53 g of 4-(N-phenyl-N-naphthylamino)phenyl-1-naphthylamine (19.5 mmol) were dissolved in 50 ml of toluene, and 0.204 g of bis(dibenzylidene acetone)palladium(0) (0.360 mmol), 0.31 ml of 50 wt % tri-tert-butylphosphine toluene solution (0.62 mmol), and 4.69 g of sodium-tert-butoxide (48.8 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran at a ratio of 8:1, stirring was conducted using petroleum ether, and vacuum drying was conducted to produce the compound of Formula 22 (5.60 g, yield 49.5%). MS: $[M+H]^+$=1227.

Example 22

Preparation of the Compound Represented by Formula 2-23

Synthesis of arylamine (4-(N-phenyl-N-naphthylamino) phenyl-1-biphenylamine) to produce the compound represented by Formula 2-23: 14.0 g of 4-bromophenyl-N-phenyl-N-naphthylamine (37.4 mmol) and 6.96 g of 4-aminobiphenyl (41.2 mmol) were dissolved in 200 ml of toluene, and 0.47 g of bis(dibenzylidene acetone)palladium (0) (0.82 mmol), 0.50 ml of 50 wt % tri-tert-butylphosphine toluene solution (1.2 mmol), and 11.86 g of sodium-tert-butoxide (123.4 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran at a ratio of 10:1, stirring was conducted using petroleum ether, and vacuum drying was conducted to produce an arylamine connection group (7.5 g, yield 43%). MS: [M+H]$^+$=462.

2) 3.3 g of compound of Formula b (5.8 mmol) and 5.90 g of 4-(N-phenyl-N-naphthylamino)phenyl-1-biphenylamine (12.8 mmol) were dissolved in 70 ml of toluene, and 0.15 g of bis(dibenzylidene acetone)palladium(0) (0.26 mmol), 0.16 ml of 50 wt % tri-tert-butylphosphine toluene solution (0.38 mmol), and 3.68 g of sodium-tert-butoxide (38.3 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran at a ratio of 8:1, stirring was conducted using petroleum ether, and vacuum drying was conducted to produce the compound of Formula 23 (3.9 g, yield 51%). MS: [M+H]$^+$=1227.

Example 23

Preparation of the Compound Represented by Formula 24

1) Synthesis of arylamine (4-(N,N-diphenylamino)-biphenyl-aniline) to produce the compound represented by Formula 24: 4.00 g of 4-chlorobiphenyl-N,N-diphenylamine (11.2 mmol) and 1.13 ml of aniline (12.4 mmol) were dissolved in 100 ml of toluene, and 0.129 g of bis(dibenzylidene acetone)palladium(0) (0.225 mmol), 0.17 ml of 50 wt % tri-tert-butylphosphine toluene solution (0.34 mmol), and 2.70 g of sodium-tert-butoxide (28.1 mmol) were added thereto. After reflux was conducted in a nitrogen atmosphere for 5 hours, distilled water was added to the reaction solution to complete the reaction. The organic layer was extracted, a column separation process was conducted using a developing solvent of n-hexane and tetrahydrofuran at a ratio of 10:1, stirring was conducted using petroleum ether, and vacuum drying was conducted to produce an arylamine connection group as an amine derivative (3.77 g, yield 81.3%). MS: [M+H]$^+$=413.

2) 2.30 g of compound of Formula b (4.08 mmol) and 3.70 g of 4-(N,N-diphenylamino)-biphenyl-aniline (8.97 mmol) were dissolved in 30 ml of toluene, and 0.094 g of bis(dibenzylidene acetone)palladium(0) (0.16 mmol), 0.14 ml of 50 wt % tri-tert-butylphosphine toluene solution (0.29 mmol), and 2.16 g of sodium-tert-butoxide (22.4 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran at a ratio of 8:1, stirring was conducted using petroleum ether, and vacuum drying was conducted to produce the compound of Formula 24 (2.7 g, yield 54%). MS: [M+H]$^+$=1227.

Example 24

Preparation of the Compound Represented by Formula 25

1) Synthesis of arylamine (4-(N-phenyl-N-phenylamino)phenyl-1-naphthylamine) to produce the compound represented by Formula 25: Synthesis was conducted through the same procedure as in synthesis of the arylamine connection group of Formula 19.

2) 5.00 g of compound of Formula d (7.98 mmol) and 7.09 g of 4-(N-phenyl-N-phenylamino)phenyl-1-naphthylamine (18.4 mmol) were dissolved in 120 ml of toluene, 5.29 g of sodium-tert-butoxide (55.0 mmol), 0.21 g of bis(dibenzylidene acetone)palladium(0) (0.37 mmol), and 0.22 ml of 50 wt % tri-tert-butylphosphine toluene solution (0.55 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 25 (5.6 g, yield 53%). MS: [M+H]$^+$=1174.

Example 25

Preparation of the compound represented by Formula 26

1) Synthesis of arylamine (4-(N-phenyl-N-phenylamino)phenyl-1-naphthylamine) to produce the compound represented by Formula 26: 15.0 g of 4-bromophenyl-N-phenyl-N-phenylamine (46.3 mmol) and 7.29 g of 1-naphthylamine (50.9 mmol) were dissolved in 200 ml of toluene, 13.34 g of sodium-tert-butoxide (138.8 mmol), 0.53 g of bis(dibenzylidene acetone)palladium(0) (0.93 mmol), and 0.56 ml of 50 wt % tri-tert-butylphosphine toluene solution (1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (13 g, yield 73%). MS: [M+H]$^+$=386.

2) 5.00 g of compound of Formula c (10.3 mmol) and 4.78 g of 4-(N-phenyl-N-phenylamino)phenyl-1-naphthylamine (12.4 mmol) were dissolved in 50 ml of toluene, 5.89 g of sodium-tert-butoxide (61.3 mmol), 0.12 g of bis(dibenzylidene acetone)palladium(0) (0.21 mmol), and 0.15 ml of 50 wt % tri-tert-butylphosphine toluene solution (0.31 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 26 (4.3 g, yield 53%). MS: [M+H]$^+$=789.

Example 26

Preparation of the Compound Represented by Formula 27

1) Synthesis of arylamine (4-(N,N-diphenylamino)-biphenyl-N'-phenylamine) to produce the compound represented by Formula 27: 4.00 g of 4-chlorobiphenyl-N,N-diphenylamine (11.2 mmol) and 1.13 ml of aniline (12.4 mmol) were dissolved in 100 ml of toluene, 2.70 g of sodium-tert-butoxide (28.1 mmol), 0.13 g of bis(dibenzylidene acetone)palladium (0) (0.23 mmol), and 0.17 ml of 50 wt % tri-tert-butylphosphine toluene solution (0.34 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 81%). MS: [M+H]$^+$=413.

2) 3.62 g of compound of Formula c (7.47 mmol) and 3.4 g of 4-(N,N-diphenylamino)-biphenyl-N'-phenylamine (8.2 mmol) were dissolved in 40 ml of toluene, 1.94 g of sodium-tert-butoxide (22.4 mmol), 0.09 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 27 (3.5 g, yield 53%). MS: [M+H]$^+$=817.

Example 27

Preparation of the Compound Represented by Formula 28

1) Synthesis of arylamine (4-(N,N-diphenylamino)-biphenyl-N'-naphthylamine) to produce the compound represented by Formula 28: 8.80 g of 4-chlorobiphenyl-N,N-diphenylamine (24.7 mmol) and 5.31 g of 1-naphthylamine (37.1 mmol) were dissolved in 200 ml of toluene, 5.94 g of sodium-tert-butoxide (61.8 mmol), 0.43 g of bis(dibenzylidene acetone)palladium(0) (0.74 mmol), and 0.61 ml of 50 wt % tri-tert-butylphosphine toluene solution (1.24 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (7.0 g, yield 61%). MS: [M+H]$^+$=413.

2) 3.62 g of compound of Formula c (7.47 mmol) and 3.8 g of 4-(N,N-diphenylamino)-biphenyl-N'-naphthylamine (8.2 mmol) were dissolved in 40 ml of toluene, 1.94 g of sodium-tert-butoxide (22.4 mmol), 0.09 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 28 (3.5 g, yield 54%). MS: [M+H]$^+$=867.

Example 28

Preparation of the Compound Represented by Formula 29

1) Synthesis of arylamine (4-(N,N-diphenylamino)-biphenyl-N'-biphenylamine) to produce the compound represented by Formula 29: 8.80 g of 4-chlorobiphenyl-N,N-diphenylamine (24.7 mmol) and 6.28 g of 4-aminobiphenyl (37.1 mmol) were dissolved in 200 ml of toluene, 5.94 g of sodium-tert-butoxide (61.8 mmol), 0.43 g of bis(dibenzylidene acetone)palladium(0) (0.74 mmol), and 0.61 ml of 50 wt % tri-tert-butylphosphine toluene solution (1.24 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (7.0 g, yield 58%). MS: [M+H]$^+$=489.

2) 3.62 g of compound of Formula c (7.47 mmol) and 4.0 g of 4-(N,N-diphenylamino)-biphenyl-N'-biphenylamine (8.2 mmol) were dissolved in 40 ml of toluene, 1.94 g of sodium-tert-butoxide (22.4 mmol), 0.09 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 29 (3.5 g, yield 53%). MS: [M+H]$^+$=893.

Example 29

Preparation of the Compound Represented by Formula 30

1) Synthesis of arylamine (4-(N-phenyl-N-naphthylamino)-biphenyl-N'-phenylamine) to produce the compound represented by Formula 30: 4.08 g of 4-chlorobiphenyl-N-phenyl-N-naphthylamine (10.1 mmol) and 1.38 ml of aniline (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 82%). MS: [M+H]$^+$=463.

2) 3.13 g of compound of Formula c (6.47 mmol) and 3.3 g of 4-(N-phenyl-N-naphthylamino)-biphenyl-N'-phenylamine (7.1 mmol) were dissolved in 40 ml of toluene, 1.94 g of sodium-tert-butoxide (22.4 mmol), 0.08 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 30 (2.5 g, yield 45%). MS: [M+H]$^+$=867.

Example 30

Preparation of the Compound Represented by Formula 31

1) Synthesis of arylamine (4-(N-phenyl-N-naphthylamino)-biphenyl-N'-naphthylamine) to produce the compound represented by Formula 31: 4.08 g of 4-chlorobiphenyl-N-phenyl-N-naphthylamine (10.1 mmol) and 2.16 g of 1-naphthylamine (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 74%). MS: $[M+H]^+=513$.

2) 3.62 g of compound of Formula c (7.47 mmol) and 3.8 g of 4-(N-phenyl-N-naphthylamino)-biphenyl-N'-naphthylamine (7.4 mmol) were dissolved in 40 ml of toluene, 1.94 g of sodium-tert-butoxide (22.4 mmol), 0.089 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 31 (3.0 g, yield 44%). MS: $[M+H]^+=91.7$.

Example 31

Preparation of the Compound Represented by Formula 32

1) Synthesis of arylamine (4-(N-phenyl-N-naphthylamino)-biphenyl-N'-biphenylamine) to produce the compound represented by Formula 32: 4.08 g of 4-chlorobiphenyl-N-phenyl-N-naphthylamine (10.1 mmol) and 2.55 g of 4-aminobiphenyl (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours.

Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 70%). MS: $[M+H]^+=539$.

2) 3.13 g of compound of Formula c (6.47 mmol) and 3.8 g of 4-(N-phenyl-N-naphthylamino)-biphenyl-N'-biphenylamine (7.1 mmol) were dissolved in 40 ml of toluene, 1.94 g of sodium-tert-butoxide (22.4 mmol), 0.081 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 32 (2.5 g, yield 41%). MS: $[M+H]^+=943$.

Example 32

Preparation of the Compound Represented by Formula 33

1) Synthesis of arylamine (4-(N-phenyl-N-biphenylamino)-biphenyl-N'-phenylamine) to produce the compound represented by Formula 33: 4.86 g of 4-chlorobiphenyl-N-phenyl-N-biphenylamine (11.2 mmol) and 1.13 ml of aniline (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 69%). MS: $[M+H]^+=489$.

2) After 3.13 g of the compound of Formula c (6.47 mmol) and 3.5 g of 4-(N-phenyl-N-biphenylamino)-biphenyl-N'-phenylamine (7.1 mmol) were dissolved in 40 ml of toluene, 1.94 g of sodium-tert-butoxide (22.4 mmol), 0.081 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 33 (2.6 g, yield 45%). MS: $[M+H]^+=893$.

Example 33

Preparation of the Compound Represented by Formula 34

1) Synthesis of arylamine (4-(N-phenyl-N-biphenylamino)-biphenyl-N'-naphthylamine) to produce the compound represented by Formula 34: 4.86 g of 4-chlorobiphenyl-N-phenyl-N-biphenylamine (11.2 mmol) and 1.78 ml of 1-naphthylamine (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (4.0 g, yield 69%). MS: $[M+H]^+=539$.

2) After 3.13 g of the compound of Formula c (6.47 mmol) and 3.8 g of 4-(N-phenyl-N-biphenylamino)-biphenyl-N'- naphthylamine (7.1 mmol) were dissolved in 40 ml of toluene, 1.94 g of sodium-tert-butoxide (22.4 mmol), 0.081 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 34 (3.1 g, yield 51%). MS: $[M+H]^+=943$.

Example 34

Preparation of the Compound Represented by Formula 35

1) Synthesis of arylamine (4-(N-phenyl-N-biphenylamino)-biphenyl-N'-biphenylamine) to produce the compound represented by Formula 35: 4.86 g of 4-chlorobiphenyl-N-phenyl-N-biphenylamine (11.2 mmol) and 2.09 ml of 4-aminobiphenyl (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.6 g, yield 56%). MS: $[M+H]^+=565$.

2) After 2.92 g of the compound of Formula c (6.02 mmol) and 3.57 g of 4-(N-phenyl-N-biphenylamino)-biphenyl-N'-biphenylamine (6.32 mmol) were dissolved in 40 ml of toluene, 1.94 g of sodium-tert-butoxide (22.4 mmol), 0.073 g of bis(dibenzylidene acetone)palladium(0) (0.13 mmol), and 0.10 ml of 50 wt % tri-tert-butylphosphine toluene solution (0.19 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 8:1, stirring was conducted using petroleum ether, and vacuum drying was conducted to produce the compound of Formula 35 (2.5 g, yield 43%). MS: $[M+H]^+=969$.

Example 35

Preparation of the Compound Represented by Formula 36

1) Synthesis of arylamine (4-(N-phenyl-N-phenylamino) phenyl-1-naphthylamine) to produce the compound represented by Formula 36: Synthesis was conducted through the same procedure as in synthesis of the arylamine connection group of Formula 2-2.

2) 4.97 g of compound of Formula e (9.63 mmol) and 5.58 g of 4-(N-phenyl-N-phenylamino)phenyl-1-naphthylamine (12.4 mmol) were dissolved in 50 ml of toluene, 1.85 g of sodium-tert-butoxide (19.3 mmol), 0.11 g of bis(dibenzylidene acetone)palladium(0) (0.19 mmol), and 0.14 ml of 50 wt % tri-tert-butylphosphine toluene solution (0.29 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 36 (4.5 g, yield 54%). MS: $[M+H]^+=865$.

Example 36

Preparation of the Compound Represented by Formula 37

1) The compound of Formula c (3.50 g, 7.23 mmol) was completely dissolved in 40 ml of THF, 4-formyl-phenylboronic acid (1.63 g, 10.8 mmol), 2M potassium carbonate solution, tetrakis(triphenylphosphine)palladium(0) (0.25 g, 0.22 mmol), and 5 ml of ethanol were added thereto, and reflux was conducted for 24 hours. After the reaction was completed, cooling to normal temperature was conducted, filtration was conducted, and washing was conducted with water and ethanol several times. Recrys-tallization was conducted with ethanol, and vacuum drying was conducted to produce 4.97 g of a compound (93% yield).

2) The compound (4.16 g, 8.16 mmol) produced in 1) and N-phenyl-o-phenylenediamine (1.58 g, 8.57 mmol) were stirred in DMAC and refluxed for 24 hours. After the reaction was completed, DMAC was concentrated, water and ethanol were added thereto, stirring was conducted, and filtration was conducted. A column separation process was conducted using a solvent of n-hexane and tetrahydrofuran (n-hexane/THF=20/1), recrystallization was conducted with ethanol, and vacuum drying was conducted to produce the compound of Formula 37 (3.5 g, 64% yield). MS: $[M+H]^+=673$.

Example 37

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. Furthermore, the substrate was dry washed using oxygen plasma for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

[HAT]

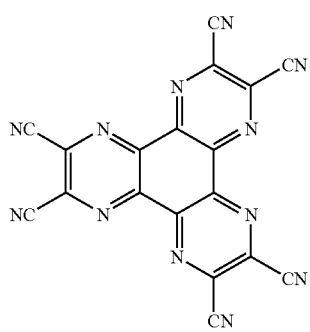

The compound of Formula 2 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

Electron transport layer material

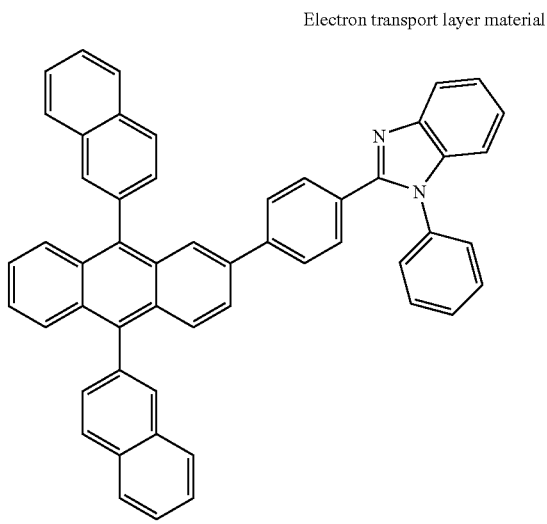

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3\times10^{-7}$.

The resulting device had an electric field of 4.63 V at a forward current density of 100 mA/cm$^2$, and a spectrum having a light efficiency of 1.89 lm/W. The operation and light emission of the device at the above-mentioned actuating voltage mean that the compound of Formula 2, which formed the layer between the hole injection layer and the light emitting layer, functions to transport holes.

Example 38

Production of an Organic Light Emitting Device

HAT was depositied on an ITO substrate, which was prepared through the same procedure as in example 37, to a thickness of 80 Å to form a thin film. The thin film can improve characteristics of an interface of the substrate and a hole injection layer. Subsequently, a compound of Formula 2 was deposited on the thin film to a thickness of 800 Å to form the hole injection layer.

NPB was deposited on the hole injection layer to a thickness of 300 Å to form a hole transport layer, Alq3 was deposited thereon to a thickness of 300 Å to form a light emitting layer. An electron transport layer and a cathode were formed on the light emitting layer through the same procedure as example 37.

In the present example, deposition speeds of an organic material and the cathode were the same as those of example 37.

The resulting device had an electric field of 5.76 V at a forward current density of 100 mA/cm$^2$, and a spectrum having a light efficiency of 1.93 lm/W. The operation and light emission of the device at the above-mentioned actuating voltage mean that the compound of Formula 2, that formed the layer between the thin film on the substrate and the hole transport layer, functions to inject holes.

Example 39

Production of an Organic Light Emitting Device

A glass substrate (corning 7059 glass), on which IZO (indium zinc oxide) was applied to a thickness of 1500 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using argon plasma under a pressure of 14 mtorr at 80 W for 5 min, and then transported to a vacuum evaporator.

The hole injection material, which was used in example 37, was vacuum deposited by heating on the IZO transport electrode, which was prepared through the above-mentioned procedure, to a thickness of 500 Å to form a hole injection layer.

NPB was vacuum deposited on the hole injection layer to a thickness of 400 Å to form a hole transport layer.

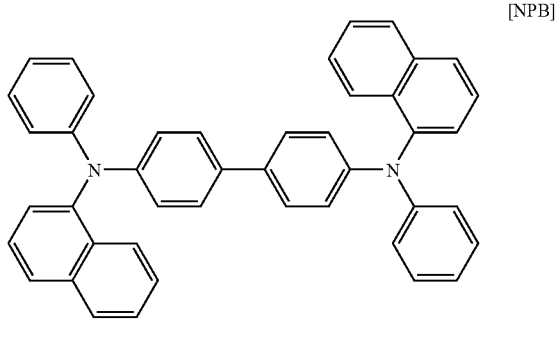

[NPB]

Both of the compound of Formula 2-66 (200 Å) and Ir(ppy)₃ were vacuum deposited (8% concentration) to form a light emitting layer.

BCP (60 Å) was vacuum deposited on the light emitting layer to form a hole blocking layer. The electron injection layer 400 Å, which was used in example 37, was deposited on BCP to form an electron injection layer.

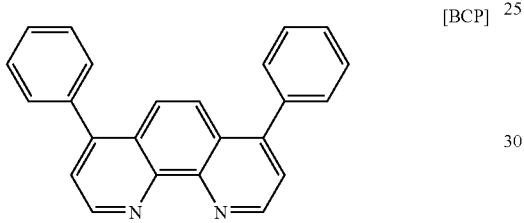

[BCP]

Lithium fluoride (LiF) having a thickness of 15 Å and aluminum having a thickness of 1500 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3 \times 10^{-7}$.

The resulting device had an electric field of 6.78 V at a forward current density of 100 mA/cm², and a spectrum having a light efficiency of 8.86 lm/W. High brightness in the present invention means that the compound of Formula 2-66 acts nicely as a host material of a phosphorescent device.

Example 40

Production of an Organic Light Emitting Device

The compound of Formula 37 was used to produce a device instead of the compound that was used as an electron transport layer in example 38. The resulting device had an electric field of 7.40 V at a forward current density of 100 mA/cm², and a spectrum having a light efficiency of 1.81 lm/W.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:

1. A compound represented by Formula 1:

[Formula 1]

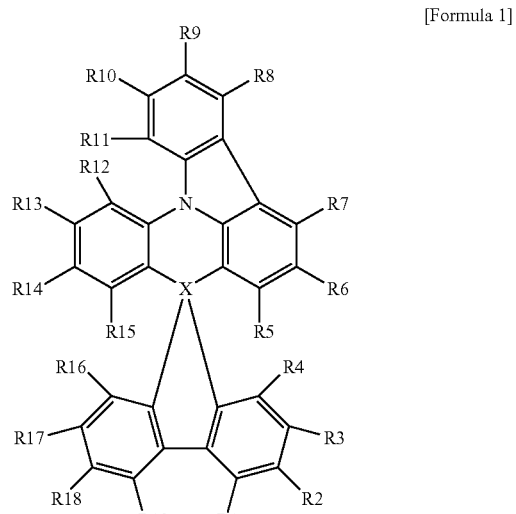

wherein X is C or Si;

$R_1$ to $R_{19}$ are each independently selected from the group consisting of hydrogen; an alkyl group, which is substituted or unsubstituted with at least one substituent group selected from the group consisting of a halogen group, an alkyl group, an alkenyl group, an alkoxy group, a substituted or un-substituted alyl amine group, a substituted or unsubstituted alyl group, a substituted or unsubstituted arylalkyl group, a substituted or unsubstituted arylalkenyl group, a substituted or unsubstituted heterocyclic group, a nitrile group, and an acetylene group; an alkoxy group, which is substituted or un-substituted with at least one substituent group selected from the group consisting of a halogen group, an alkyl group, an alkenyl group, an alkoxy group, a substituted or unsubstituted arylamine group, and a substituted or unsubstituted aryl group; an alkenyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an aryl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or un-substituted arylalkyl group, a substituted or unsubstituted arylalkenyl group, a substituted or unsubstituted heterocyclic group, a nitrile group, and an acetylene group; an arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or un-substituted arylalkyl group, a substituted or unsubstituted arylalkenyl group, a substituted or unsubstituted heterocyclic group, a nitrile group, and an acetylene group; a hetero arylamine group, which is substituted or unsubstituted with at least one substituent group selected from the group consisting of a halogen group, an alkyl group, an alkenyl group, an alkoxy group, a substituted or un-substituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; a heterocyclic group, which is substituted or un-substituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or un-substituted arylalkenyl group, a substituted or unsubstituted heterocyclic group, a nitrile group, and an acetylene group and which includes O, N, or S as a heteroatom; an amino group, which is substituted with at least one substituent group selected from the group consisting of an alkyl group, an alkenyl group, a substituted or unsubstituted aryl group, a substituted or unsubstituted arylalkyl group, and a substituted or unsubstituted arylalkenyl group; a nitrile group; a nitro group; a halogen group; an amide group; and an ester group, and $R_1$ to $R_{19}$ may form aliphatic or hetero condensation rings along with adjacent groups; and $R_{11}$ and $R_{12}$ may be directly connected to each other, or may form a condensation ring along with a group selected from the group consisting of O, S, NR, PR, C=O, CRR', C=CRR', and SiRR', wherein R and R' are each independently selected from the group consisting of hydrogen, oxygen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or un-substituted heterocyclic group, a nitrile group, an amide group, and an ester group, and may form a condensation ring to form a spiro compound.

2. The compound as set forth in claim 1, wherein $R_{11}$ and $R_{12}$ are directly connected to each other, or form a condensation ring along with a group selected from the group consisting of O, S, NR, PR, C=, CRR', C=CRR', and SiRR' (R and R' being as defined in claim 1).

3. The compound as set forth in claim 1, wherein the aryl group of $R_1$ to $R_{19}$ is selected from the group consisting of a phenyl group, a biphenyl group, a terphenyl group, a stilbene group, a naphthyl group, an anthracenyl group, a phenanthrene group, a pyrenyl group, and a perylenyl group.

4. The compound as set forth in claim 1, wherein the arylamine group or the hetero arylamine group of $R_1$ to $R_{19}$ is selected from the group consisting of a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

5. The compound as set forth in claim 1, wherein the heterocyclic group of $R_1$ to $R_{19}$ is selected from the group consisting of a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

6. The compound as set forth in claim 1, wherein the compound of Formula 1 is any one of following compounds:

[Formula 2]

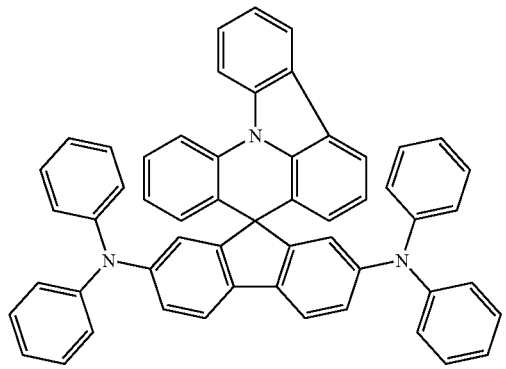

[Formula 3]

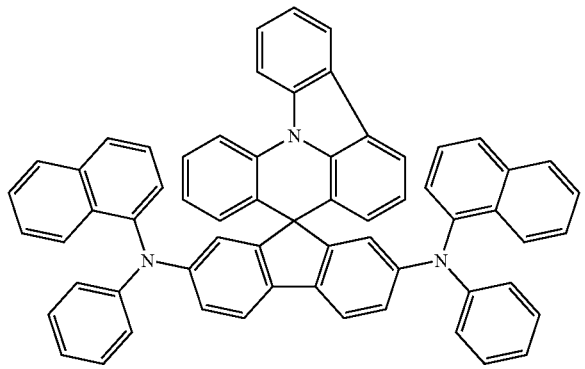

[Formula 4]

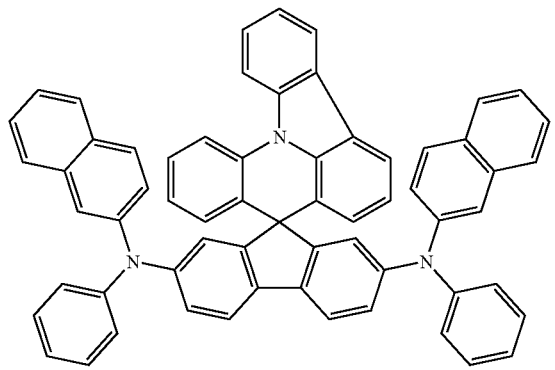

[Formula 5]

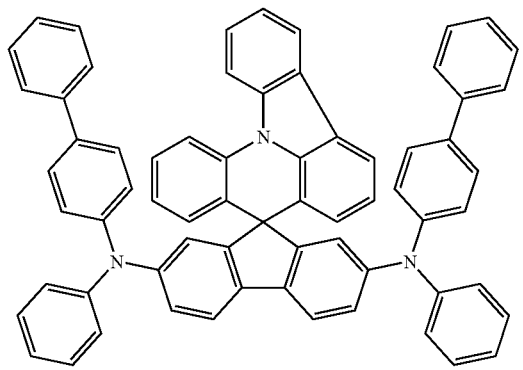

-continued
[Formula 6]
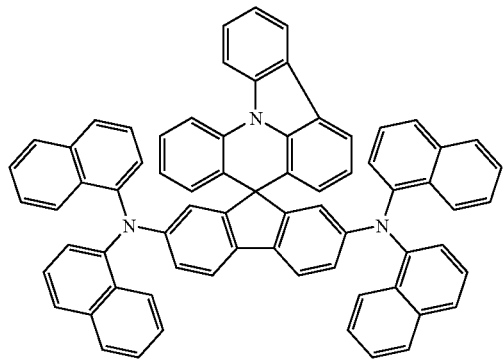
[Formula 7]
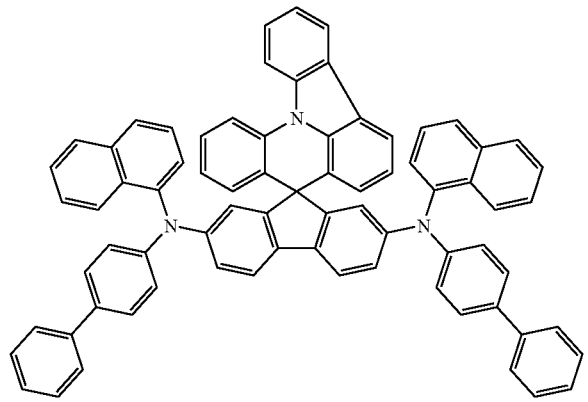
[Formula 8]
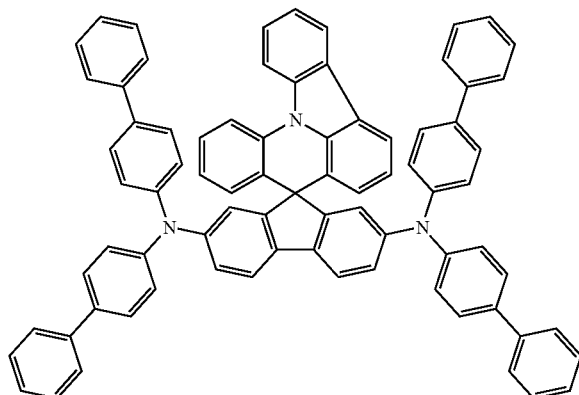
[Formula 9]
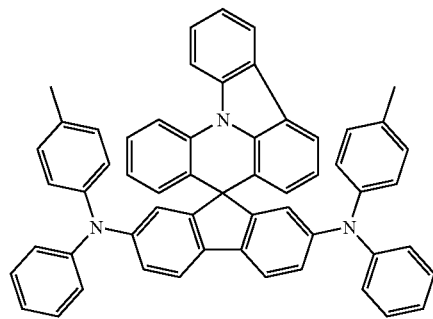
[Formula 10]
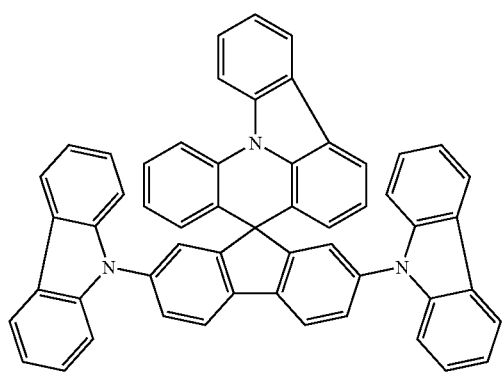
[Formula 11]
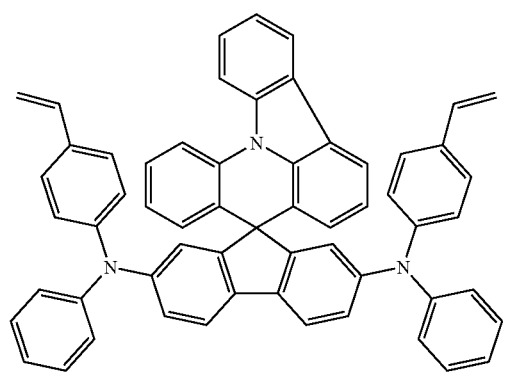

-continued
[Formula 12]
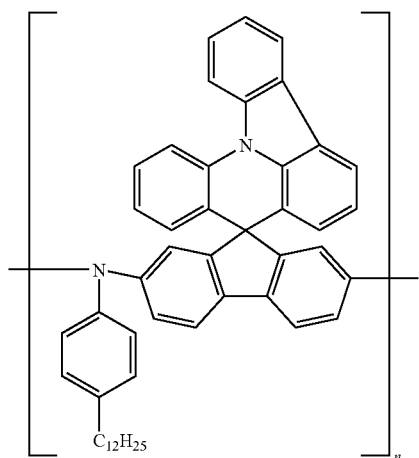
[Formula 13]
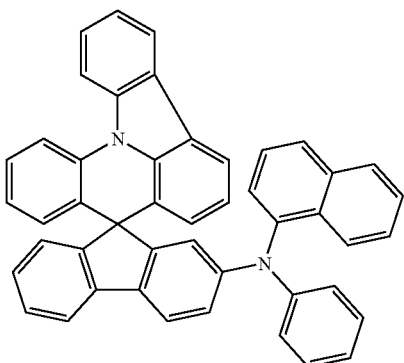
[Formula 14]
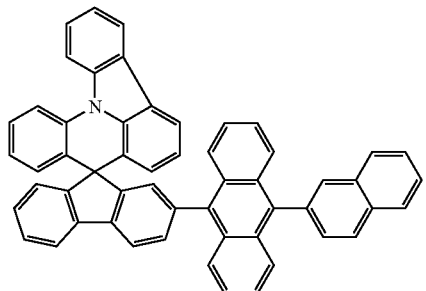
[Formula 15]
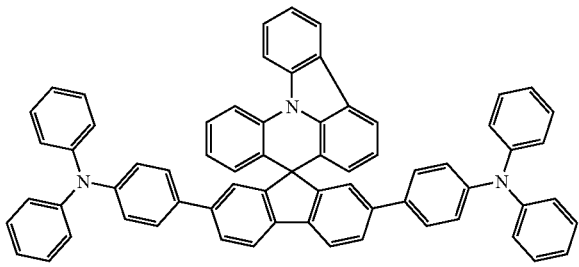
[Formula 16]
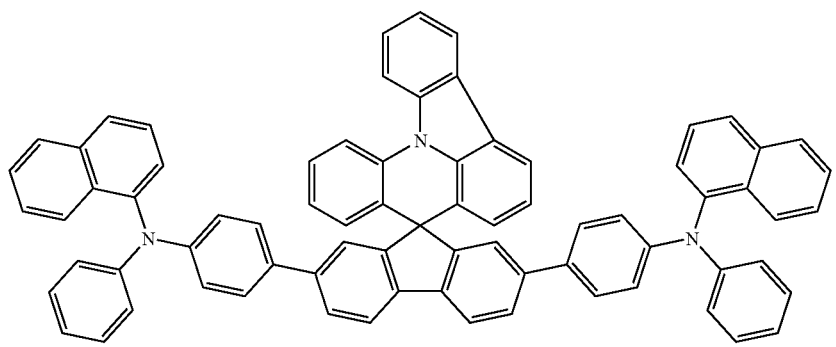
[Formula 17]
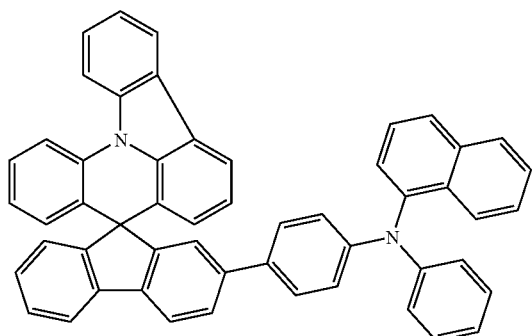

-continued
[Formula 18]
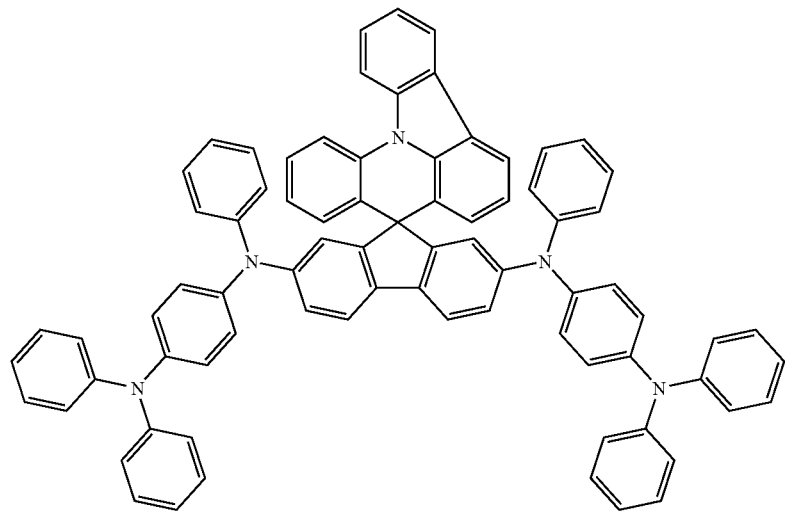
[Formula 9]
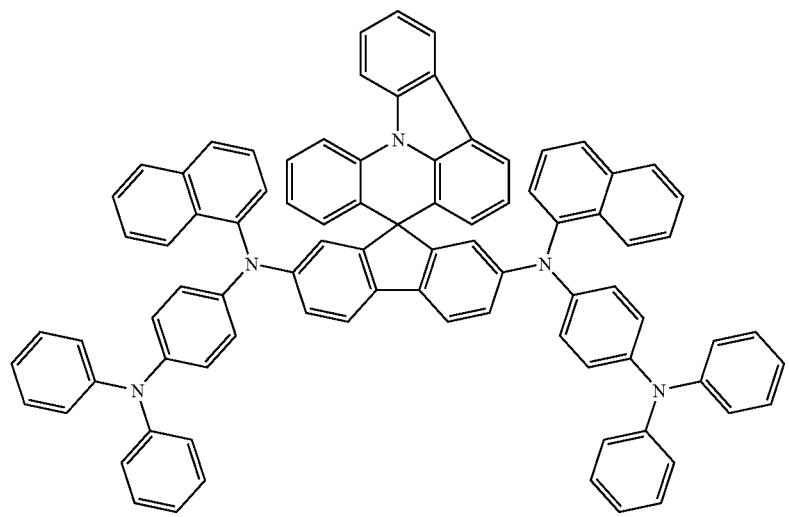
[Formula 20]
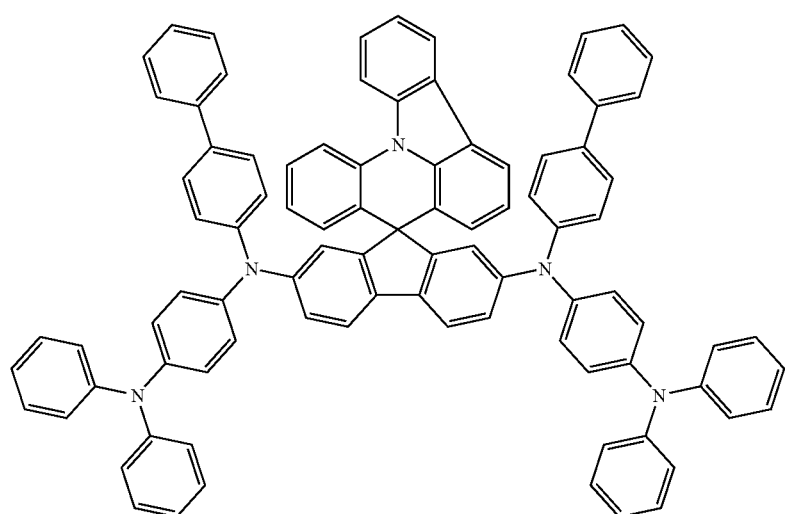

-continued
[Formula 21]
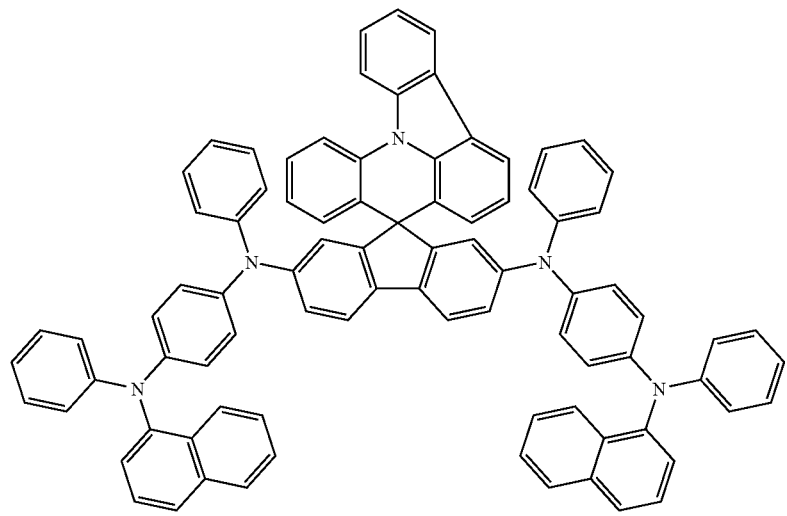
[Formula 22]
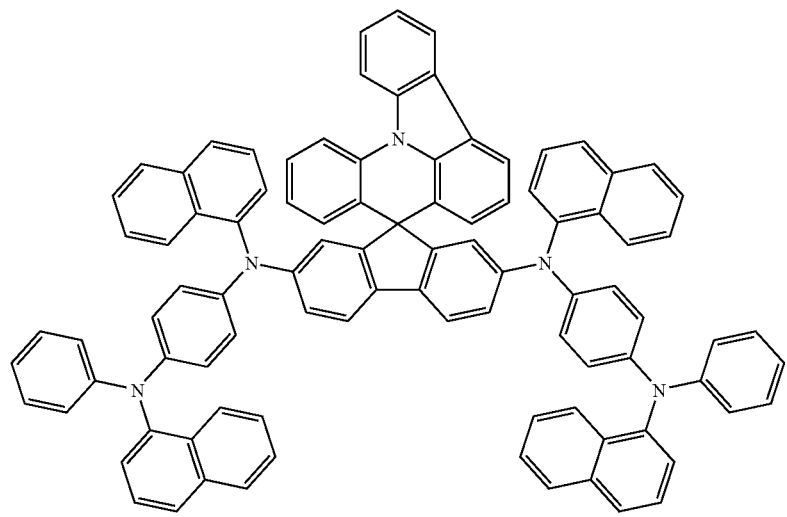
[Formula 23]
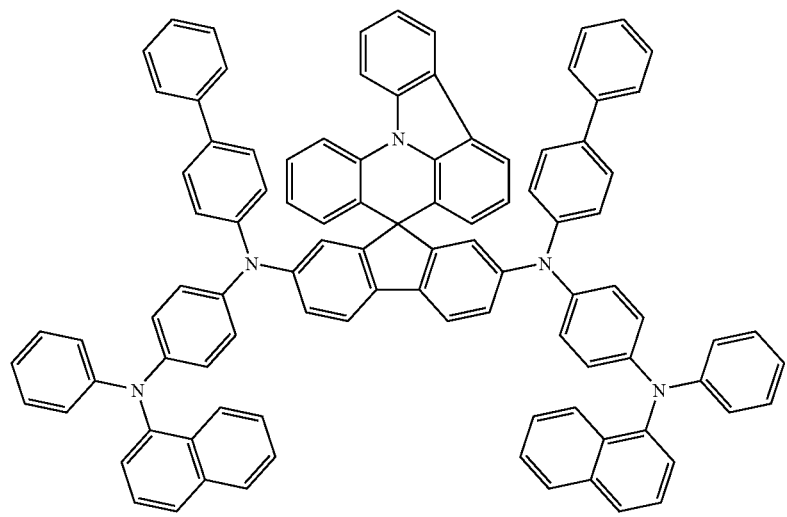

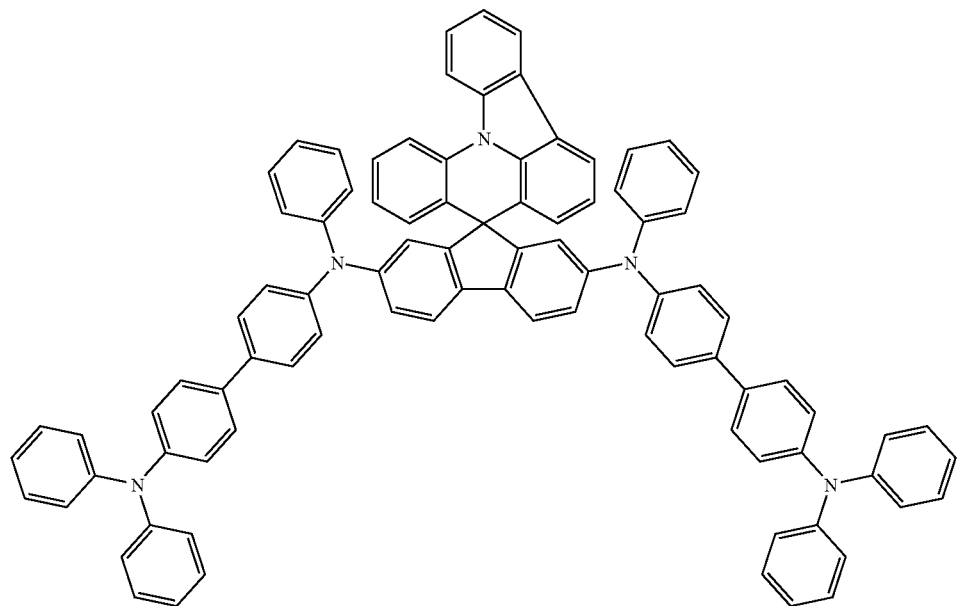
[Formula 24]
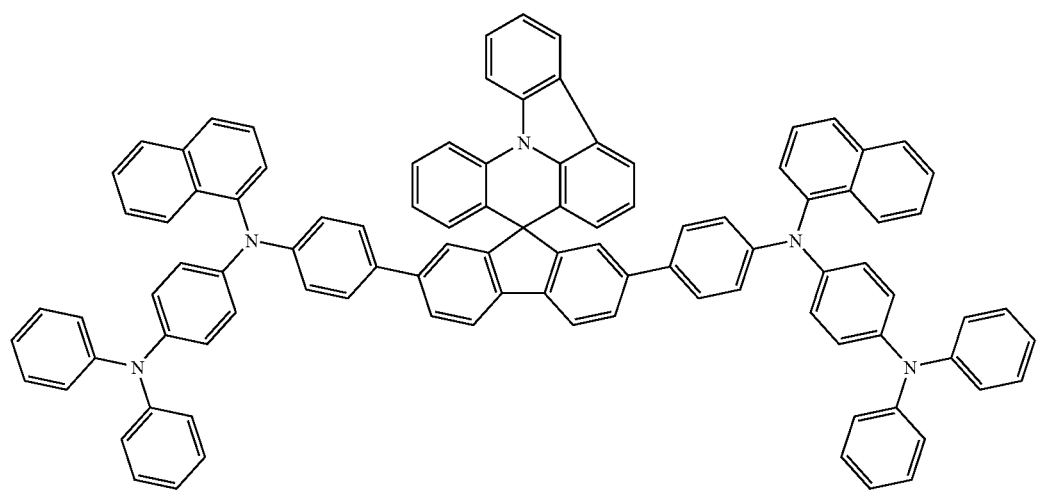
[Formula 25]

[Formula 26]
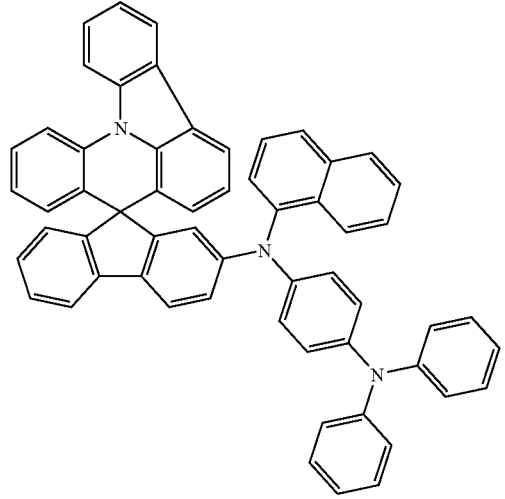
[Formula 27]
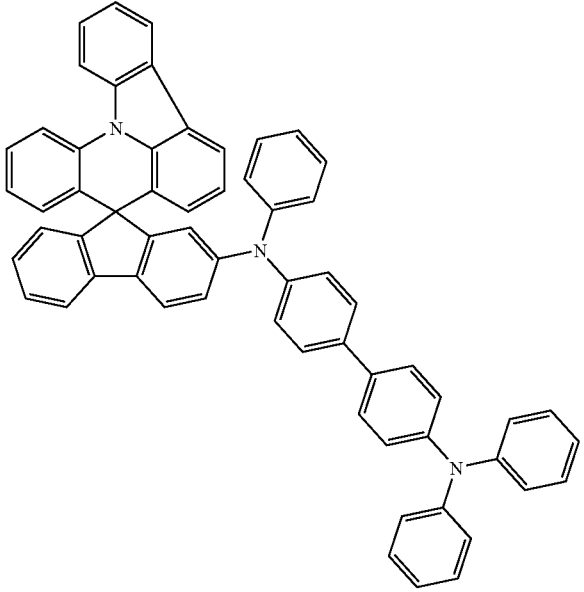
[Formula 28]
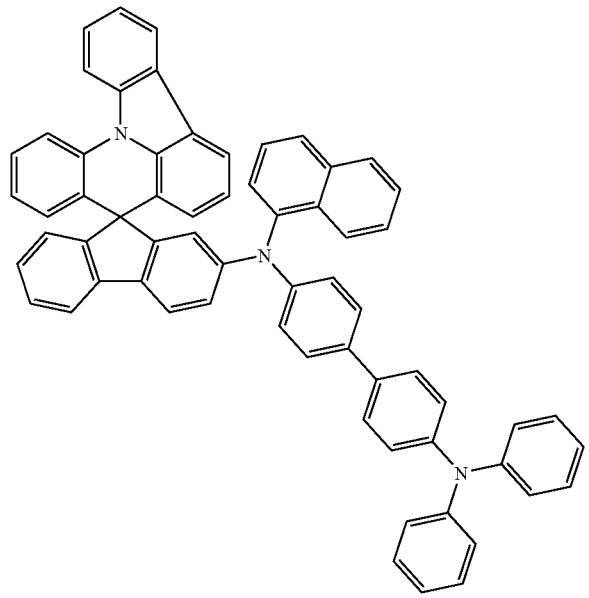
[Formula 29]
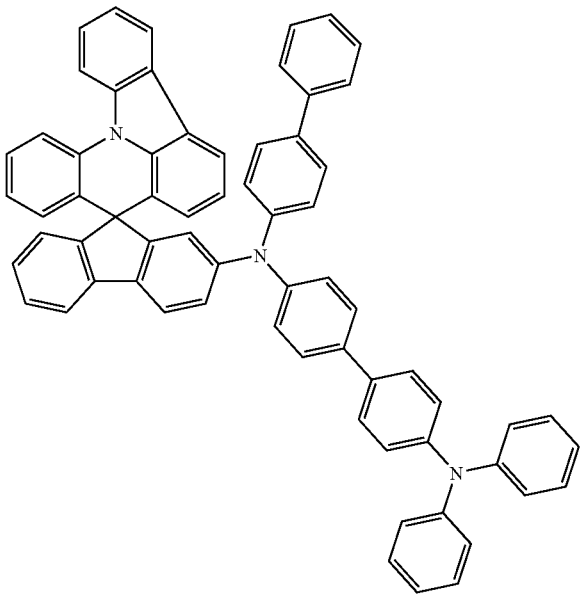

-continued
[Formula 30]
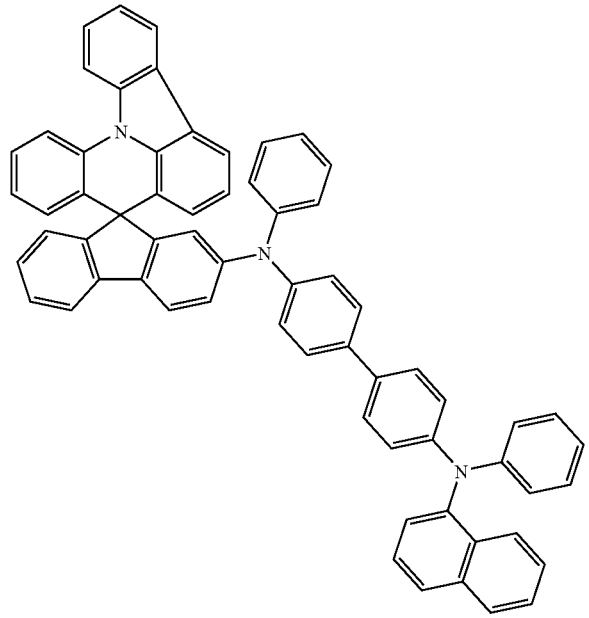
[Formula 31]
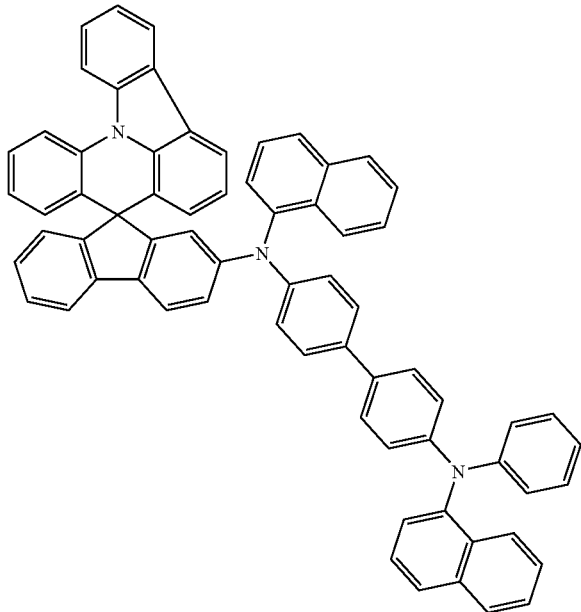
[Formula 32]
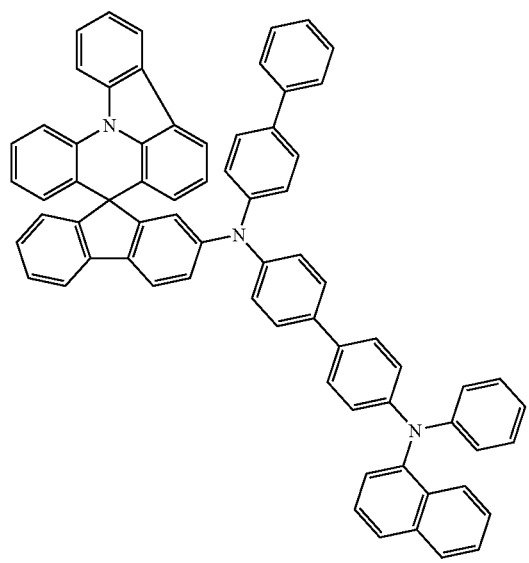
[Formula 33]
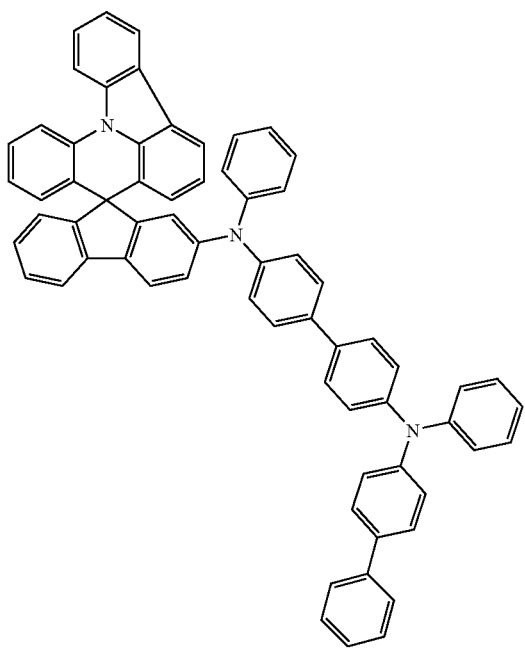

-continued

[Formula 34]

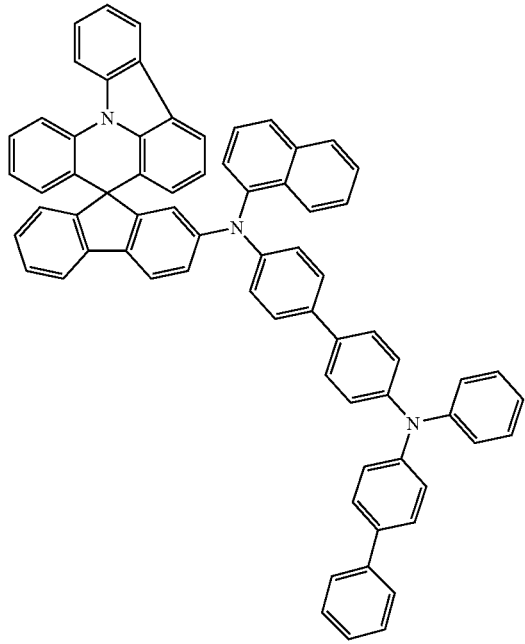

[Formula 35]

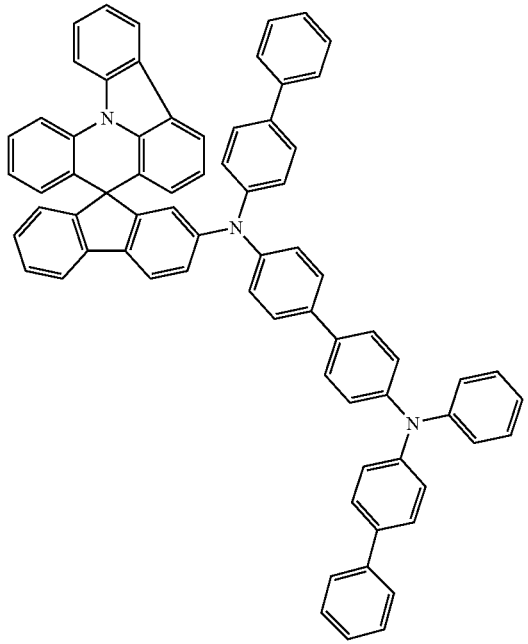

[Formula 36]

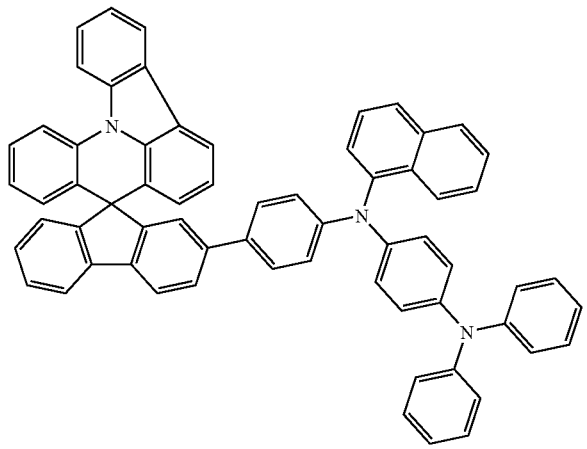

[Formula 37]

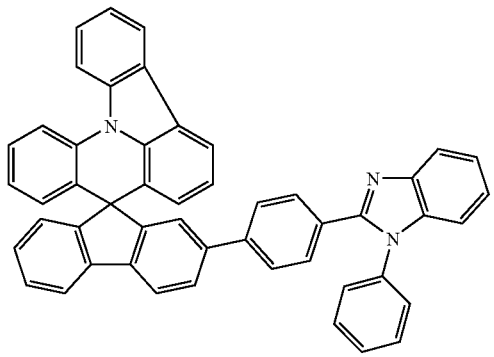

7. An organic light emitting device, comprising:
a first electrode;
organic material layer(s) comprising a light emitting layer, wherein at least one layer of the organic material layer(s) includes the compound of Formula 1 according to claim 1; and
a second electrode;
wherein the first electrode, the organic material layer(s), and the second electrode form layered structure.

8. The organic light emitting device as set forth in claim 7, wherein the organic material layer(s) comprise a hole transport layer, and the hole transport layer includes the compound of Formula 1.

9. The organic light emitting device as set forth in claim 7, wherein the organic material layer(s) comprise a hole injection layer, and the hole injection layer includes the compound of Formula 1.

10. The organic light emitting device as set forth in claim 7, wherein the organic material layer(s) comprise a layer which both injects and transports holes and which includes the compound of Formula 1.

11. The organic light emitting device as set forth in claim 7, wherein the organic material layer(s) comprise a hole injection layer and a hole transport layer, and said hole injection layer and said hole transport layer include the compound of Formula 1.

12. The organic light emitting device as set forth in claim 7, wherein the light emitting layer includes the compound of Formula 1.

13. The organic light emitting device as set forth in claim 7, comprising a polymer or a copolymer of the compound of Formula 1.

* * * * *